(12) United States Patent
Hammock et al.

(10) Patent No.: US 12,357,598 B2
(45) Date of Patent: Jul. 15, 2025

(54) TREATMENT OF NEURODEVELOPMENTAL DISORDERS

(71) Applicants: THE REGENTS OF THE UNIVERSITY OF CALIFORNIA, Oakland, CA (US); CHIBA UNIVERSITY, Chiba (JP)

(72) Inventors: Bruce D. Hammock, Davis, CA (US); Sung Hee Hwang, Woodland, CA (US); Jun Yang, Davis, CA (US); Kenji Hashimoto, Chiba (JP)

(73) Assignees: THE REGENTS OF THE UNIVERSITY OF CALIFORNIA, Oakland, CA (US); CHIBA UNIVERSITY, Chiba (JP)

( * ) Notice: Subject to any disclaimer, the term of this patent is extended or adjusted under 35 U.S.C. 154(b) by 917 days.

(21) Appl. No.: 17/416,192

(22) PCT Filed: Dec. 20, 2019

(86) PCT No.: PCT/US2019/067979
§ 371 (c)(1),
(2) Date: Jun. 18, 2021

(87) PCT Pub. No.: WO2020/132522
PCT Pub. Date: Jun. 25, 2020

(65) Prior Publication Data
US 2023/0301949 A1 Sep. 28, 2023

Related U.S. Application Data

(60) Provisional application No. 62/783,963, filed on Dec. 21, 2018.

(51) Int. Cl.
| | | |
|---|---|---|
| *A61K 31/191* | (2006.01) | |
| *A61K 31/197* | (2006.01) | |
| *A61K 31/221* | (2006.01) | |
| *A61P 25/18* | (2006.01) | |
| *A61P 25/28* | (2006.01) | |

(52) U.S. Cl.
CPC .......... *A61K 31/191* (2013.01); *A61K 31/197* (2013.01); *A61K 31/221* (2013.01); *A61P 25/18* (2018.01); *A61P 25/28* (2018.01)

(58) Field of Classification Search
CPC .. A61K 31/191; A61K 31/197; A61K 31/221; A61P 25/18; A61P 25/28
See application file for complete search history.

(56) References Cited

FOREIGN PATENT DOCUMENTS

WO    WO-2017120012 A1 *   7/2017   .......... A61K 31/135

OTHER PUBLICATIONS

Zayed (The Diamond Rehab Thailand), 2024 (Year: 2024).*
Heath, Oct. 2015 (Year: 2015).*
Verywellmind, (https://www.verywellmind.com/neurodevelopmental-disorders-definition-symptoms-traits-causes-treatment-5221231, 2022) (Year: 2022).*
Mayo Clinic—Autism (Year: 2018).*
Argou-Cardozo et al., Clostridium Bacteria and Autism Spectrum Conditions: A Systematic Review and Hypothetical Contribution of Environmental Glyphosate Levels, Medical Sciences, 2018, vol. 6, No. 29, 11 pages.
Atone et al., Prostaglandins and Other Lipid Mediators Cytochrome P450 derived epoxidized fatty acids as a therapeutic tool against neuroinflammatory diseases, Prostaglandins Other Lipid Mediat., Apr. 2020, 147:106385.
Baio et al., Prevalence of Autism Spectrum Disorder Among Children Aged 8 Years—Autism and Developmental Disabilities Monitoring Network, 11 Sites, United States, MMWR Surveillance Summaries, Apr. 27, 2018, vol. 67, No. 6, pp. 1-23.
Balan et al., Contribution of induced pluripotent stem cell technologies to the understanding of cellular phenotypes in schizophrenia, Neurobiology of Disease, 2019, vol. 131, 104162.
Balan et al., Exon resequencing of H3K9 methyltransferase complex genes, EHMT1, EHTM2 and WIZ, in Japanese autism subjects, Molecular Autism, 2014, 5:49.
Balan et al., Contribution of induced pluripotent stem cell technologies to the understanding of cellular phenotypes in schizophrenia, Neurobiology of Disease, 2019, vol. 131, 104162, 18 pages.
Bettaieb et al., Soluble Epoxide Hydrolase Deficiency or Inhibition Attenuates Diet-Induced Endoplasmic Reticulum Stress in Liver and Adipose Tissue, The Journal of Biological Chemistry, May 17, 2013, vol. 288, No. 20, pp. 14189-14199.
Boulanger-Bertolus et al., Increasing Role of Maternal Immune Activation in Neurodevelopmental Disorders, Frontiers in Behavioral Neuroscience, Oct. 5, 2018, vol. 12, No. 230, 6 pages.
Bradberry et al., Glyphosate Poisoning, Toxicol Rev, 2004, vol. 23, No. 3, pp. 159-167.

(Continued)

*Primary Examiner* — Umamaheswari Ramachandran
(74) *Attorney, Agent, or Firm* — Mintz Levin Cohn Ferris Glovsky and Popeo, P.C.

(57) ABSTRACT

Provided herein are methods of preventing, reducing, ameliorating, mitigating, inhibiting, treating and/or reversing a neurodevelopmental disorder related to prenatal maternal immune activation in an individual in need thereof comprising administering to said individual an agent that increases the level of epoxy-fatty acids wherein said individual experienced maternal immune activation one or more times during gestation. Also provided herein are methods of preventing, reducing, ameliorating, mitigating, inhibiting treating and/or reversing schizophrenia or autism spectrum disorder an individual comprising administering to said individual an agent that increases the level of epoxy-fatty acids.

13 Claims, 28 Drawing Sheets
Specification includes a Sequence Listing.

(56) References Cited

OTHER PUBLICATIONS

Brown et al., (2004) Serologic Evidence of Prenatal Influenza in the Etiology of Schizophrenia, Arch Gen Psychiatry, Aug. 2004, vol. 61, pp. 774-780.
Brown et al., (2010) Prenatal Infection and Schizophrenia: A Review of Epidemiologic and Translational Studies, Am J Psychiatry, Mar. 2010, 167(3):261-280.
Brown et al., Elevated Maternal C-Reactive Protein and Autism in a National Birth Cohort, Mol Psychiatry, Feb. 2014, 19(2):259-264.
Brown et al., Maternal immune activation and neuropsychiatric illness: A translational research perspective, Am J Psychiatry, Nov. 1, 2018, 175(11): 1073-1083.
Campbell, William B., New role for epoxyeicosatrienoic acids as anti-inflammatory mediators, TiPS, Apr. 2000, vol. 21, pp. 125-127.
Canetta et al., Elevated Maternal C-Reactive Protein and Increased Risk of Schizophrenia in a National Birth Cohort, Am J Psychiatry, Sep. 1, 2014, vol. 171, No. 9, pp. 960-968.
Careaga et al., Maternal immune activation and autism spectrum disorder: From rodents to nonhuman and human primates, Biol Psychiatry, Mar. 1, 2017, 81(5):391-401.
Cryan et al., The Micribiota-Gut-Brain Axis, Physiol Rev, Aug. 28, 2019, 99:1877-1945.
Cryan et al., The Micribiota-Gut-Brain Axis, Physiol Rev, Aug. 28, 2019, 99:1946-2013.
Elvevåg et al., Cognitive Impairment in Schizophrenia is the Core of the Disorder. Critical Reviews™ in Neurobiology, 2000, vol. 14, No. 1, pp. 1-21.
Estes et al., Maternal immune activation: implication for neuropsychiatric disorders, Science, Aug. 19, 2016, 353(6301):772-777.
Fatemi et al., The Neurodevelopmental Hypothesis of Schizophrenia, Revisited, Schizophrenia Bulletin, Feb. 17, 2009, vol. 35, No. 3, pp. 528-548.
Fujita et al., Supplementation with D-serine prevents the onset of cognitive deficits in adult offspring after maternal immune activation, Scientific Reports, Nov. 17, 2016, 6:37261.
Fusar-Poli et al., Cognitive functioning in prodromal psychosis: A Meta-analysis, Arch Gen Psychiatry, 2012, 69:562-571.
Guidotti et al., (2000) Decrease in Reelin and Glutamic Acid Decarboxylase$_{67}$ (GAD$_{67}$) Expression in Schizophrenia and Bipolar Disorder: A Postmortem Brain Study, Arch Gen Psychiatry, 2000, 57:1061-1069.
Gumusoglu et al., Maternal Inflammation and Neurodevelopmental Programming: A Review of Preclinical Outcomes and Implications for Translational Psychiatry, Biological Psychiatry, Jan. 15, 2019, (in the press 2018), 85:107-121.
Gur et al., Neurocognitive Growth Charting in Psychosis Spectrum Youths, JAMA Psychiatry, Feb. 5, 2014, 71:366-374.
Hallmayer et al., Genetic Heritability and Shared Environmental Factors Among Twin Pairs With Autism, Arch Gen Psychiatry, Nov. 2011, 68:1095-1102.
Han et al., Intake of 7,8-Dihydroxyflavone During Juvenile and Adolescent Stages Prevents Onset of Psychosis in Adult Offspring After Immune Activation, Scientific Reports, Nov. 8, 2016, 6:36087.
Han et al., Intake of 7,8-dihydroxyflavone from pregnancy to weaning prevents cognitive deficits in adult offspring after maternal immune activation, Eur Arch Psychiatry Clin Neurosci, 2017, 267:479-483.
Hansen et al., Explaining the Increase in the Prevalence of Autism Spectrum Disorders: The Proportion Attributable to Changes in Reporting Practices, JAMA Pediatr., Nov. 3, 2014, 169:56-62.
Hantsoo et al., Inflammation: A Proposed Intermediary Between Maternal Stress and Offspring Neuropsychiatric Risk, Biol Psychiatry, Jan. 15, 2019, vol. 85, No. 2, pp. 97-106.
Hashimoto et al., Phencyclidine-induced cognitive deficits in mice are improved by subsequent subchronic administration of clozapine, but not haloperidol, European Journal of Pharmacology, 2005, 519:114-117.
Hashimoto, Kenji, Soluble epoxide hydrolase: a new therapeutic target for depression, Expert Opinion on Therapeutic Targets, 2016, 20:1149-1151.
Hashimoto, Kenji, Role of Soluble Epoxide Hydrolase in Metabolism of PUFAs in Psychiatric and Neurological Disorders, Frontiers in Pharmacology, Jan. 30, 2019, vol. 10, Article 36.
Hashimoto, Kenji, Recent Advances in the Early Intervention in Schizophrenia: Future Direction from Preclinical Findings, Current Psychiatry Reports, 2019, 21:75.
Hashimoto, Kenji, Understanding the link between maternal infections and neurodevelopmental disorders in offspring; The role of abnormalities in metabolism of polyunsaturated fatty acids, Brain, Behavior, and Immunity, 2019 (available online Aug. 4, 2019), vol. 81, pp. 4-5.
Herrmann et al., The Shikimate Pathway, Annu. Rev. Plant. Physiol. Plant. Mol. Biol., 1999, 50:473-503.
Imaizumi et al., Controlling the Regional Identity of hPSC-Derived Neurons to Uncover Neuronal Subtype Specificity of Neurological Disease Phenotypes, Stem Cell Reports, Dec. 8, 2015, 5:1010-1022.
Imig et al., Soluble Epoxide Hydrolase as a Therapeutic Target for Cardiovascular Diseases, Nat Rev Drug Discov, Oct. 2009, 8:794-805.
Inceoglu et al., Endoplasmic reticulum stress in the peripheral nervous system is a significant driver of neuropathic pain, Proc Natl Acad Sci USA, Jul. 21, 2015, vol. 112, No. 29, pp. 9082-9087.
Inceoglu et al., Modulation of mitochondrial dysfunction and endoplasmic reticulum stress are key mechanisms for the wide-ranging actions of epoxy fatty acids and soluble epoxide hydrolase inhibitors, Prostaglandins Other Lipid Mediat., Nov. 2017, 133:68-78.
International Search Report and Written Opinion for International Application No. PCT/US2019/067979, mailed Apr. 14, 2020, 11 pages.
Jiang et al., Maternal infection during pregnancy and risk of autism spectrum disorders: A systematic review and meta-analysis, Brain, Behavior, and Immunity, 2016, 58:165-172.
Jonas et al., The 22q11.2 Deletion Syndrome as a Window into Complex Neuropsychiatric Disorders Over the Lifespan, Biol Psychiatry, Mar. 1, 2014, 75(5):351-360.
Kentner et al., Maternal immune activation: reporting guidelines to improve the rigor, reproducibility, and transparency of the model, Neuropsychopharmacology, 2019, (published online Aug. 21, 2018).
Kier et al., Review of genotoxicity studies of glyphosate and glyphosate-based formulations. Critical Reviews in toxicology, 2013, 43:4, pp. 283-315.
Kim et al., Environmental risk factors and biomarkers for autism spectrum disorder: an umbrella review of the evidence, Lancet Psychiatry, 219, 6:590-600.
Kimoto et al., Lower Expression of Glutamic Acid Decarboxylase 67 in the Prefrontal Cortex in Schizophrenia: Contribution of Altered Regulation by Zif268, Am J Psychiatry, Sep. 2014, 171(9):969-978.
Lai et al., Autism, Lancet, 2014, published online Sep. 26, 2013, 383:896-910.
Lewis et al., Cortical Parvalbumin Interneurons and Cognitive Dysfunction in Schizophrenia, Trends Neurosci, Jan. 2012, 35(1):57-67.
Liu et al., Altered composition and function of intestinal microbiota in autism spectrum disorders: a systematic review, Translational Psychiatry, 2019, 9:43.
Lodge et al., A Loss of Parvalbumin-Containing Interneurons Is Associated with Diminished Oscillatory Activity in an Animal Model of Schizophrenia, The Journal of Neuroscience, Feb. 25, 2009, vol. 29, No. 8, pp. 2344-2354.
López-Vicario et al., Inhibition of soluble epoxide hydrolase modulates inflammation and autophagy in obese adipose tissue and liver: role for omega-3 epoxides, Proc Natl Acad Sci USA, Jan. 13, 2015, vol. 112, No. 2, pp. 536-541.
Lord et al., Autism spectrum disorder, Lancet, Aug. 11, 2018, 392(10146): 508-520.
Ma et al., Effects of AS2586114, a soluble epoxide hydrolase inhibitor, on hyperlocomotion and prepulse inhibition deficits in mice after administration of phencyclidine, Pharmacology, Biochemistry and Behavior, 2013, 110:98-103.

(56) References Cited

OTHER PUBLICATIONS

Ma et al., Key role of soluble epoxide hydrolase in the neurodevelopmental disorders of offspring after maternal immune activation, Proc Natl Acad Sci USA, Apr. 2, 2019, vol. 116, No. 14, pp. 7083-7088.
Matsumoto et al., Functional Neurons Generated from T Cell-Derived Induced Pluripotent Stem Cells for Neurological Disease Modeling, Stem Cell Reports, 2016, vol. 6, pp. 422-435.
Matsuura et al., Dietary glucoraphanin prevents the onset of psychosis in the adult offspring after maternal immune activation, Scientific Reports, Feb. 1, 2018, 8:2158.
Maeda et al., The Shikimate Pathway and Aromatic Amino Acid Biosynthesis in Plants, Annu Rev Plant Biol, 2012, 63:73-105.
Meyer, Urs, Prenatal Poly (I:C) exposure and other developmental immune activation models in rodent systems, Biol Psychiatry, 2014, 75:307-315.
Morisseau et al., Epoxide Hydrolases: Mechanisms, Inhibitor Designs, and Biological Roles, Annu. Rev. Pharmacol. Toxicol., 2005, 45:311-333.
Morisseau et al., Impact of Soluble Epoxide Hydrolase and Epoxyeicosanoids on Human Health, Annu Rev Pharmacol Toxicol, 2013 53:37-58.
Ostermann et al., Oral treatment of rodents with soluble epoxide hydrolase inhibitor 1-trifluoromethoxyphenyl-3-(1-propionylpiperidin-4-yl)urea (TPPU): bioavailability, resulting drug levels and modulation of oxylipin pattern, Prostaglandins Other Lipid Mediat. Sep. 2015, 121(0 0), pp. 131-137.
Ozawa et al., Immune Activation During Pregnancy in Mice Leads to Dopaminergic Hyperfunction and Cognitive Impairment in the Offspring: A Neurodevelopmental Animal Model of Schizophrenia, Biol Psychiatry, 2006, 59:546-554.
Patterson, PH, Immune involvement in schizophrenia and autism: Etiology, pathology and animal models, Behaviour Brain Research, 2009, 204:313-321.
Ren et al., Gene deficiency and pharmacological inhibition of soluble epoxide hydrolase confers resilience to repeated social defeat stress, Proc Natl Acad Sci USA, published online Mar. 14, 2016, 113:E1944-E1952.
Ren et al., Soluble epoxide hydrolase plays a key role in the pathogenesis of Parkinson's disease, Proc Natl Acad Sci USA, 2018, vol. 115, No. 25, E5815-E5823.
Rose et al., 1-Aryl-3-(1-acylpiperidin-4-yl)urea Inhibitors of Human and Murine Soluble Epoxide Hydrolase: Structure-Activity Relationships, Pharmacokinetics, and Reduction of Inflammatory Pain, J Med Chem., Oct. 14, 2020, 53(19):7067-7075.
Rueda-Ruzafa et al., Gut microbiota and neurological effects of glyphosate, Neurotoxicology, 2019, 75:1-8.
Sagiv et al., Prenatal Organophosphate Pesticide Exposure and Traits Related to Autism Spectrum Disorders in a Population Living in Proximity to Agriculture, Environmental Health Perspectives, 2018, 126:047012-1-047012-9.
Samsel et al., Glyphosate, pathways to modern diseases II: Celiac sprue and gluten intolerance, Interdiscip Toxicol, 2013, vol. 6, No. 4, pp. 159-184.
Samsel et al., Glyphosate's suppression of cytochrome P450 enzymes and amino acid biosynthesis by the gut microbiome: pathways to modern diseases, Entropy, 2013, 15:1416-1463.
Samsel et al., Glyphosate, pathways to modern diseases III: Manganese, neurological diseases, and associated pathologies. Surgical Neurology International, 2015, 6:45.
Schneider et al., Psychiatric Disorders from Childhood to Adulthood in 22q11.2 Deletion Syndrome: Results from the International Consortium on Brain and Behavior in 22q11.2 Deletion Syndrome, Am J Psychiatry, Jun. 2014, 171(6):627-639.
Sealey et al., Environmental factors in the development of autism spectrum disorders, Environmental International, 2016, 88:288-298.
Seneff et al., Aluminum and Glyphosate Can Synergistically Induce Pineal Gland Pathology: Connection to Gut Dysbiosis and Neurological Disease, Agricultural Sciences, 2015, vol. 6, pp. 42-70.

Sherwin et al., Microbiota and the social brain, Science, Nov. 1, 2019, 366, eaar2016.
Shimmura et al., Alteration of Plasma Glutamate and Glutamine Levels in Children with High-Functioning Autism, PLoS One, 2011, 6(10):e25340.
Shinohe et al., Increased serum levels of glutamate in adult patients with autism, Progress in Neuropsychopharmacology & Biological Psychiatry,2006, 30:1472-1477.
Shirai et al., Dietary Intake of Sulforaphane-Rich Broccoli Sprout Extracts Adulthood, PLoS One, Jun. 24, 2015, 10(6):e0127244.
St Clair et al., Rates of Adult Schizophrenia Following Prenatal Exposure to the Chinese Famine of 1959-1961, JAMA, 2005, 294:557-562.
Seubert et al., Role of epoxyeicosatrienoic acids in protecting the myocardium following ischemia/reperfusion injury, Prostaglandins Other Lipid Mediat., Jan. 2007, 82(1-4):50-59.
Susser et al., Prenatal famine and adult mental illness: interpreting concordant and discordant results from the Dutch and Chinese Famines, Social Science & Medicine, 2013, 97:325-330.
Susser et al., Schizophrenia After Prenatal Exposure to the Dutch Hunger Winter of 1944-1945, Arch Gen Psychiatry, Dec. 1992, 49:983-988.
Swanson et al., Genetically engineered crops, glyphosate and the deterioration of health in the United States of America, Journal of Organic Systems, 2014, 9(2).
Swardfager et al., Metabolic/inflammatory/vascular comorbidity in psychiatric disorders; soluble epoxide hydrolase (sEH) as a possible new target, Neurosci Biobehav Rev., Apr. 2018, 87:56-66.
Takahashi et al., Induction of Pluripotent Stem Cells from Adult Human Fibroblasts by Defined Factors, Cell, Nov. 30, 2007, 131:861-872.
Tomova et al., Gastrointestinal microbiota in children with autism in Slovakia, Physiology & Behavior, 2015, 138:179-187.
Toyoshima et al., Analysis of induced pluripotent stem cells carrying 22q11.2 deletion, Translational Psychiatry, 2016, 6:e934.
Von Ehrenstein et al., Prenatal and Infant Exposure to Ambient Pesticides and Autism Spectrum Disorder in Children: Population Based Case-Control Study, BMJ, 2019, 364:l962.
Vuong et al., Emerging roles for the gut microbiome in autism spectrum disorder, Biol Psychiatry, Mar. 1, 2017, 81:411-423.
Wagner et al., The Role of Long Chain Fatty Acids and Their Epoxide Metabolites in Nociceptive Signaling, Prostaglandins Other Lipid Mediat., Oct. 2014, 0:2-12.
Wagner et al., Soluble Epoxide Hydrolase as a Therapeutic Target for Pain, Inflammatory and Neurodegenerative Diseases, Pharmacol Ther., Dec. 2017, 180:62-76.
Wang et al., Elevated Fecal Short Chain Fatty Acid and Ammonia Concentrations in Children with Autism Spectrum Disorder, Dig Dis Sci, 2012, 57:2096-2102.
Wang et al., Alterations in Gut Glutamate Metabolism Associated with Changes in Gut Microbiota Composition in Children with Autism Spectrum Disorder, mSystems, Jan./Feb. 2019, vol. 4, Issue 1, e00321-18.
Wang et al., Lipidomic profiling reveals soluble epoxide hydrolase as a therapeutic target of obesity-induced colonic inflammation, Proc Natl Acad Sci USA, May 15, 2018, vol. 115, No. 20, pp. 5283-5288.
Williams et al., Safety Evaluation and Risk Assessment of the Herbicide Roundup and Its Active Ingredient, Glyphosate, for Humans, Regulatory Toxicology and Pharmacology, 2000, 31:117-165.
Xu et al., Association Between Gut Microbiota and Autism Spectrum Disorder: A Systematic Review and Meta-Analysis, Frontiers in Psychiatry, Jul. 2019, vol. 10, Article 473.
Yang et al., Quantitative Profiling Method for Oxylipin Metabolome by Liquid Chromatography Electrospray Ionization Tandem Mass Spectrometry, Anal Chem, Oct. 1, 2018, 81(19): 8085-8093.
Yang et al., Loss of parvalbumin-immunoreactivity in mouse brain regions after repeated intermittent administration of esketamine, but not R-ketamine, Psychiatry Research, 2016, 239:281-283.
Zerbo et al., Association Between Influenza Infection and Vaccination During Pregnancy and Risk of Autism Spectrum Disorder, JAMA Pediatrics, 2017, 171:e163609.

(56) References Cited

OTHER PUBLICATIONS

Zerbo et al., Maternal mid-pregnancy C-reactive protein and risk of autism spectrum disorders: the early markers for autism study, Transl Psychiatry, 2016, 6:e783.

Zheng et al., Blood Glutamate Levels in Autism Spectrum Disorder: A Systematic Review and Meta-Analysis, PLoS One, Jul. 8, 2016, 11:e0158688.

Zuckerman et al., Immune Activation During Pregnancy in Rats Leads to a PostPubertal Emergence of Disrupted Latent Inhibition, Dopaminergic Hyperfunction, and Altered Limbic Morphology in the Offspring: A Novel Neurodevelopmental Model of Schizophrenia, Neuropsychopharmacology, 2003, 28:1778-1789.

* cited by examiner

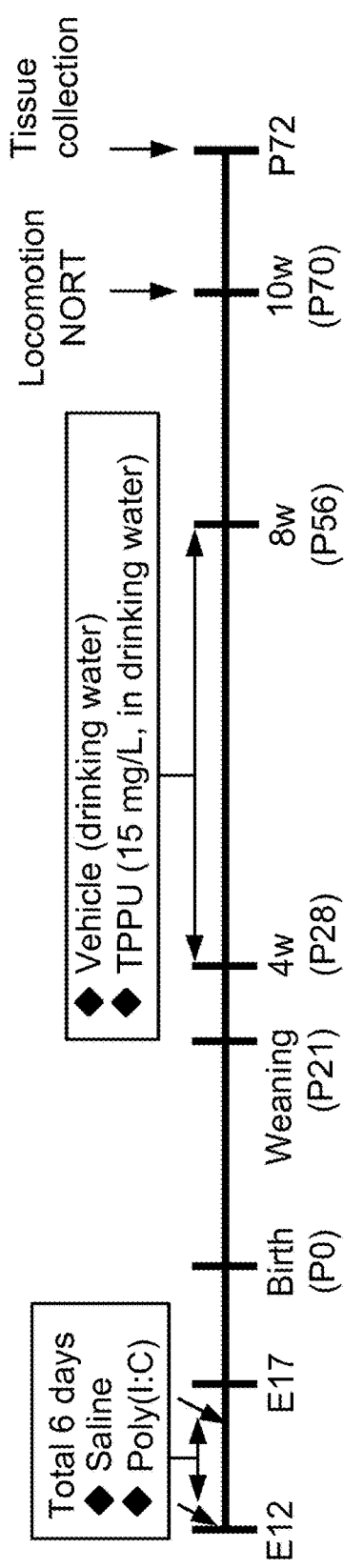
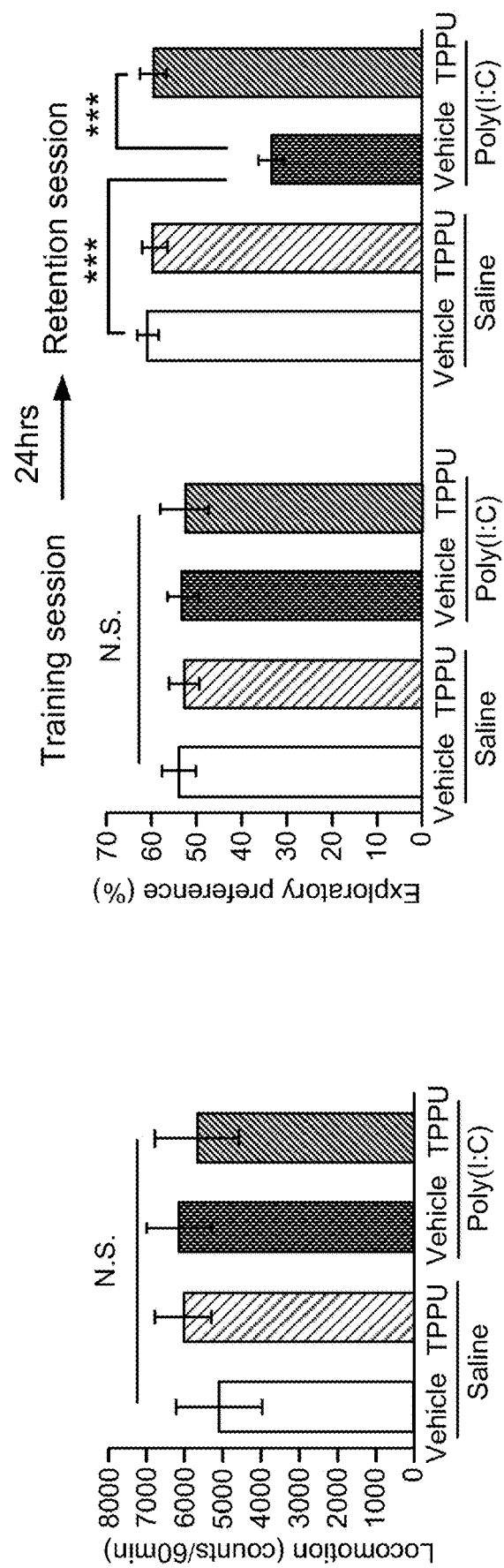
FIG. 4A
FIG. 4B
FIG. 4C

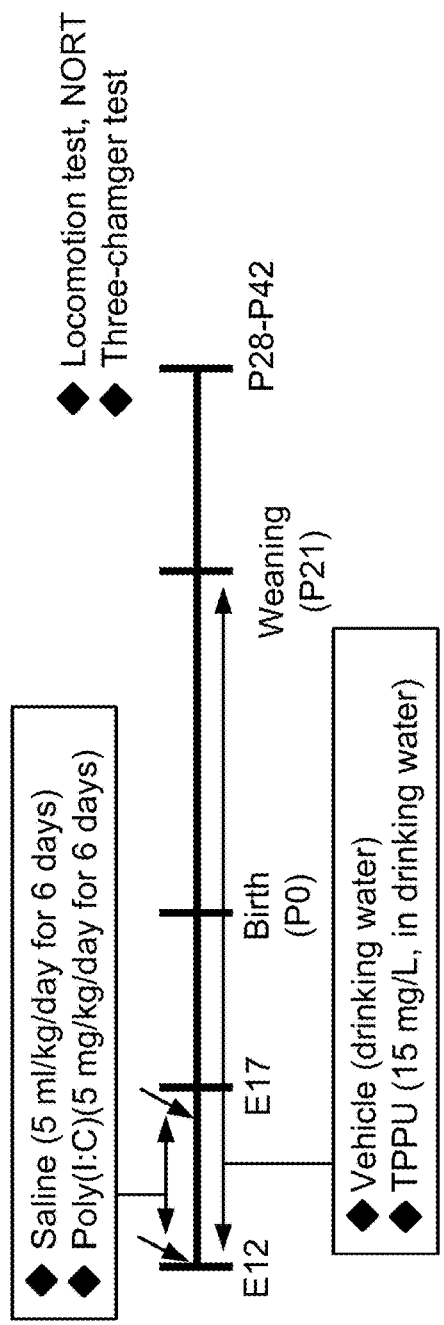
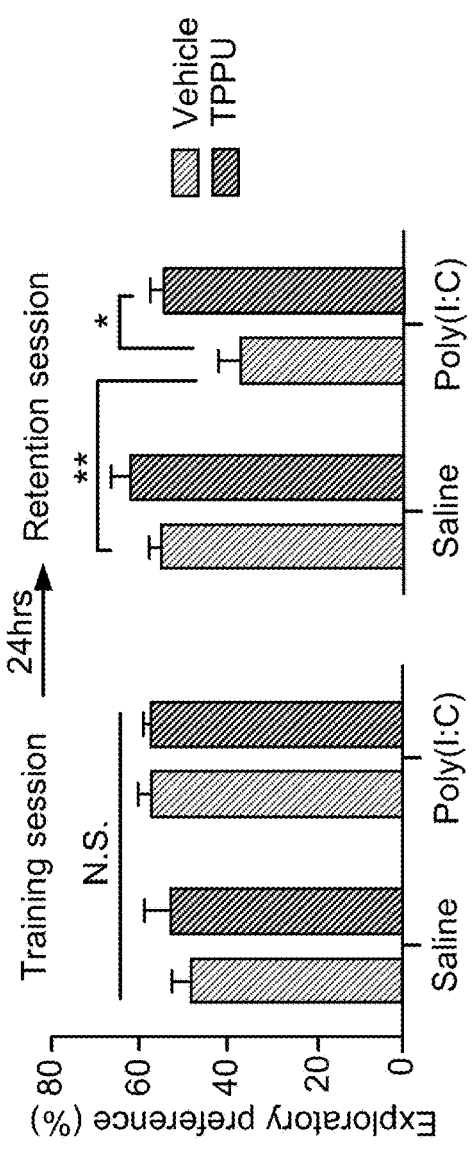
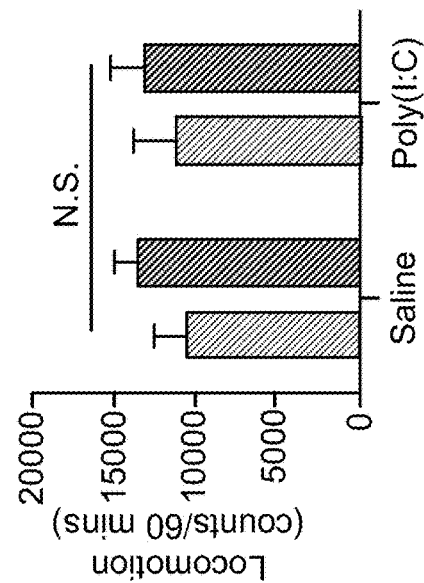
FIG. 6A
FIG. 6B
FIG. 6C

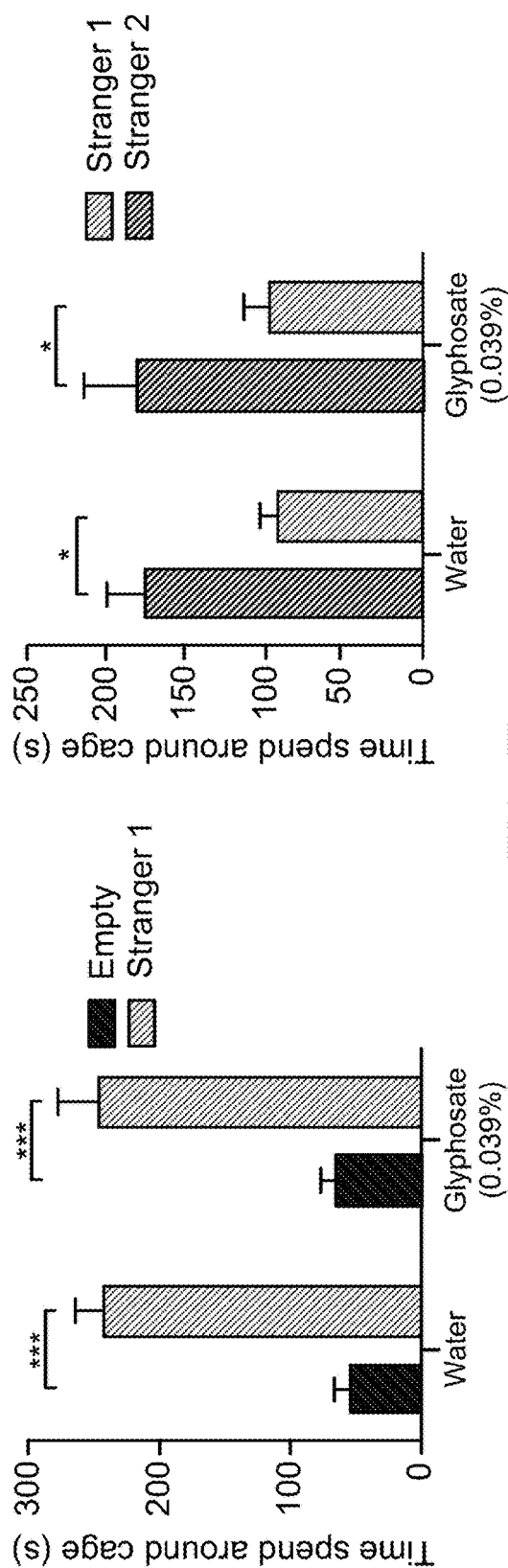
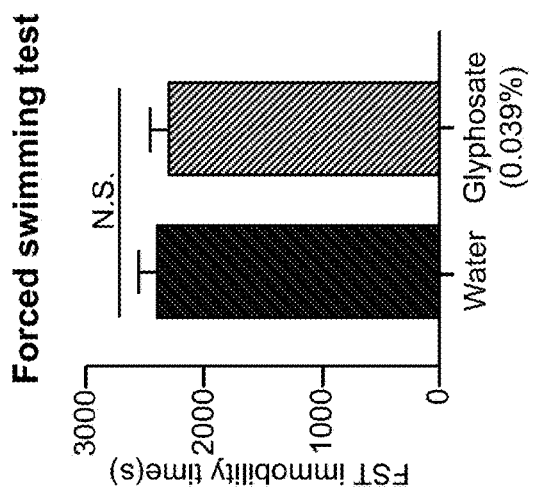
FIG. 7D
FIG. 7E

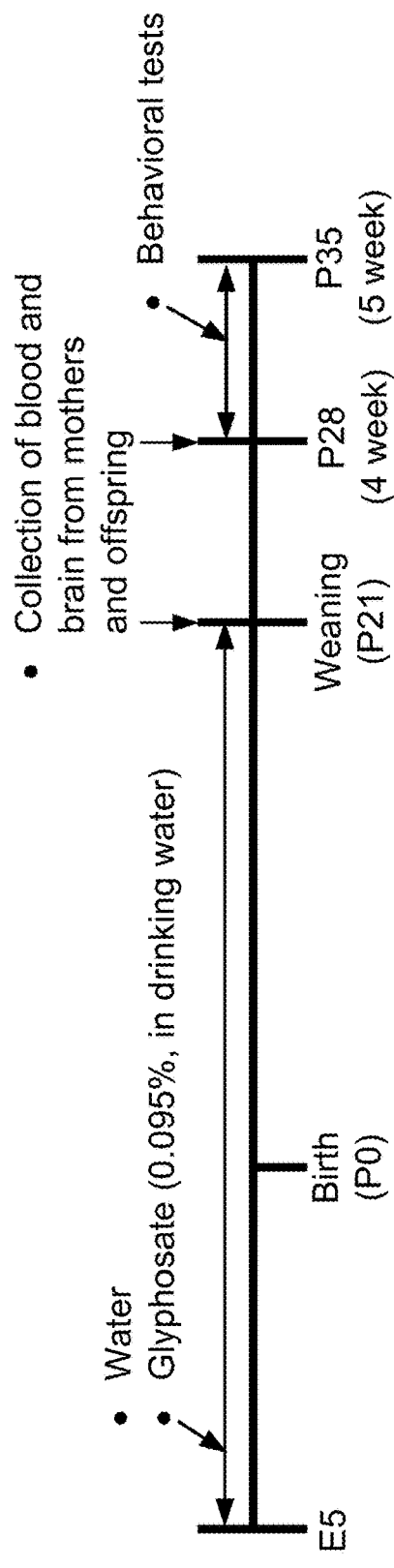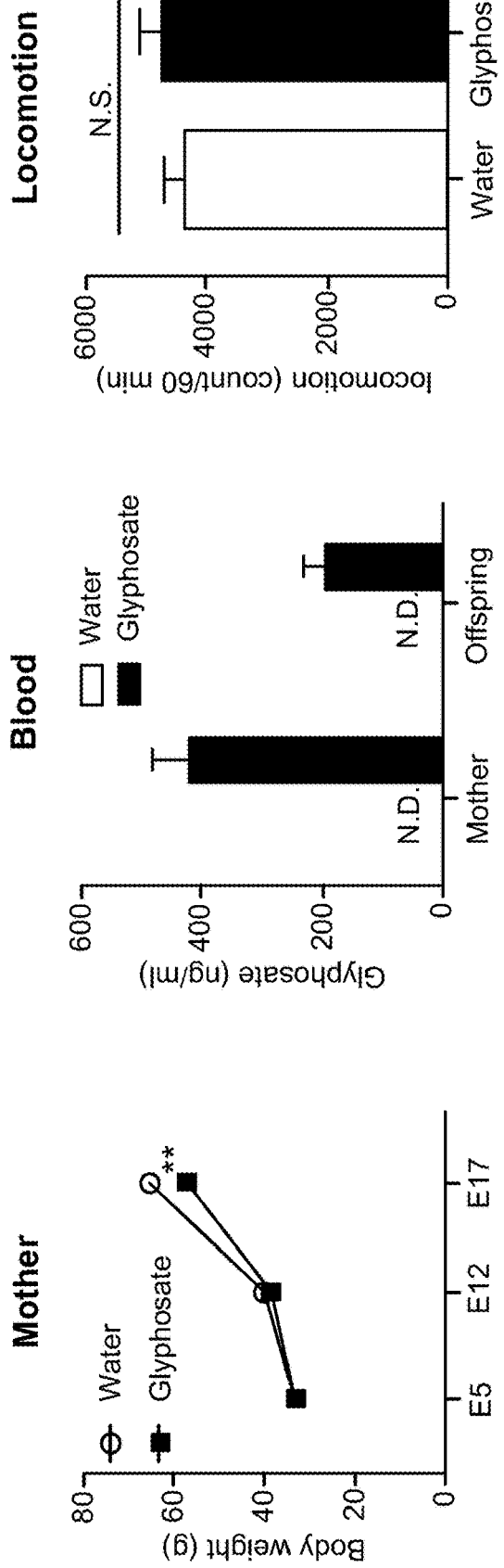
FIG. 8A
FIG. 8B
FIG. 8C
FIG. 8D

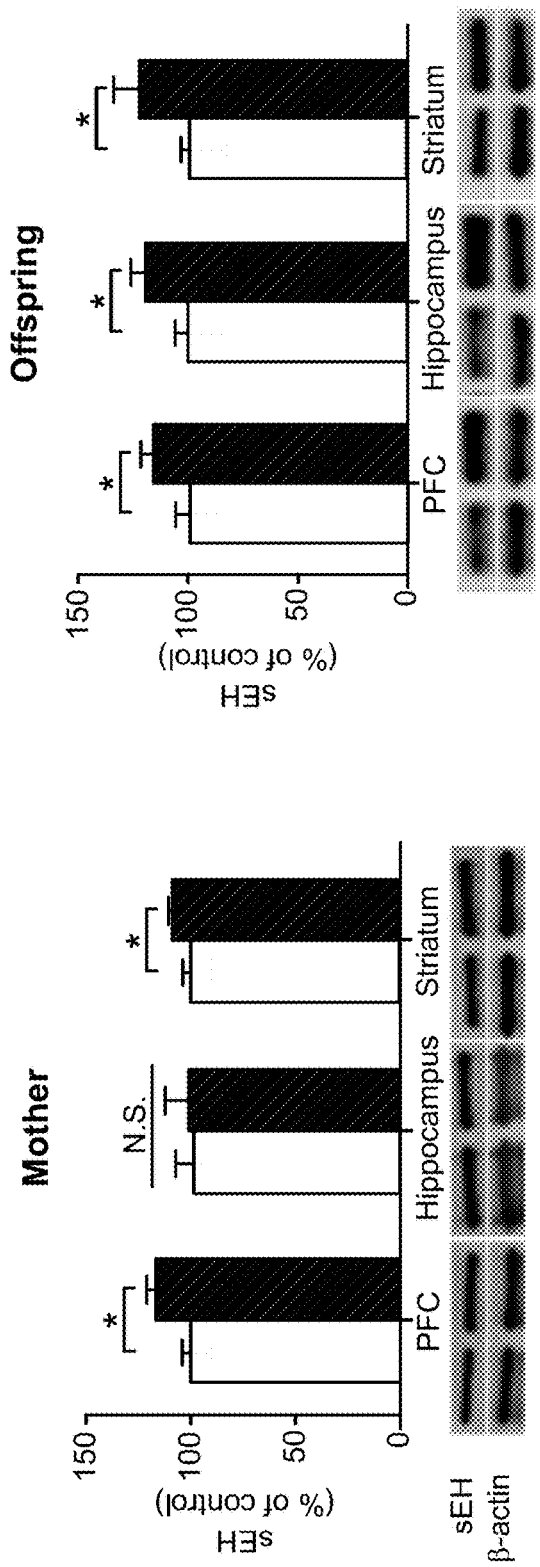
FIG. 8H
FIG. 8I
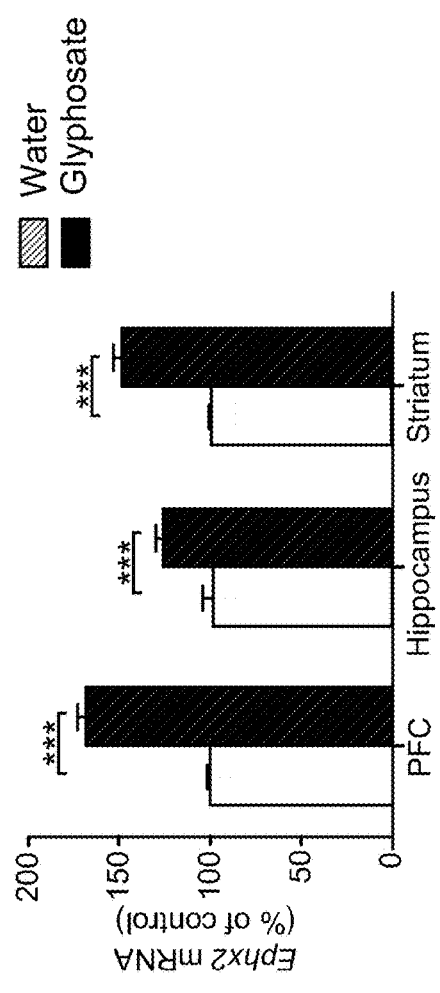
FIG. 8J

TREATMENT OF NEURODEVELOPMENTAL DISORDERS

CROSS-REFERENCE TO RELATED APPLICATIONS

This application is the U.S. National Stage Entry Under § 371 of International Application No. PCT/US2019/067979, filed Dec. 20, 2019, which claims the priority benefit to U.S. Provisional Application No. 62/783,963 filed Dec. 21, 2018, each which is incorporated herein by reference in its entirety for all purposes.

STATEMENT OF GOVERNMENTAL SUPPORT

This work was supported in part by Grant No. ES002710 & ES004699, awarded by the National Institutes of Health (NIH). The Government has certain rights in the invention.

BACKGROUND

Epidemiological studies implicate that prenatal environmental factors, including maternal immune activation (MIA), play a key role in the etiology of neurodevelopmental disorders such as schizophrenia and autism spectrum disorder (ASD) (1-7). A number of studies suggest associations between maternal infections or inflammatory biomarkers and schizophrenia, and ASD (2-4,7). For example, there are key epidemiological results supporting associations between maternal infectious pathogens (i.e., influenza virus, herpes simplex virus, *Toxoplasma gondii*, rubella, and bacterial pathogens) and inflammatory biomarkers (i.e., cytokines and C-reactive protein) and schizophrenia (2,7,8). The Finnish Prenatal Studies birth cohort showed that elevated maternal levels of C-reactive protein in early to mild-gestation was related to an increased risk of ASD in offspring (9), although maternal mid-pregnancy levels of C-reactive protein were related to a decreased risk of ASD (10). A meta-analysis suggests that maternal infection during pregnancy increases the risk of ASD in offspring (4). Collectively, MIA during pregnancy can increase the risk of neurodevelopmental disorders in offspring. The onset of schizophrenia and ASD is young adulthood and before 3 years of age, respectively. However, the precise mechanisms underlying MIA-induced increase of the risk for neurodevelopmental disorders remain largely unknown.

Although animal models are limited in their generalizability to neurodevelopmental disorders, accumulating studies demonstrate the neurobiological pathways between MIA and neurodevelopmental disorders (7,11). A number of studies make use of immune-activating agents that primarily stimulate the innate immune system, such as the synthetic double-stranded RNA analogue polyriboinosinic-polyribocytidilic acid [poly(I:C)], a Toll-like receptor 3 agonist (12-16). Offspring of prenatal rodents exposed to poly(I:C) mimics schizophrenia (or ASD)-like behavioral abnormalities in adulthood (or childhood), although MIA model using poly(I:C) does not reproduce the full spectrum of immune responses normally induced by infectious pathogens (7).

Many epoxy fatty acids (EpFAs) are produced from the corresponding fatty acids by cytochrome P450 enzymes. Epoxyeicosatrienoic acids (EETs) and epoxydocosapentaenoic acids (EDPs) are produced from arachidonic acid and docosahexaenoic acid (DHA), respectively. EETs, EDPs, and some other EpFAs have potent anti-inflammatory properties. However, these mediators are broken down into their corresponding diols by soluble epoxide hydrolase (sEH), and inhibition of sEH enhances the beneficial effects of EpFAs such as EETs (17-19). Potent anti-inflammatory effects of EETs and key role of sEH have been reported in multiple animal models, including pain, obesity, depression, and Parkinson's disease (20-27). However, there are no reports showing the role of sEH in the pathogenesis of neurodevelopmental disorders in offspring after MIA.

SUMMARY

The present methods are based, in part, on the discovery that soluble epoxide hydrolase (sEH) plays a role in the onset of neurodevelopmental disorders related to prenatal maternal immune activation.

In one aspect, provided are methods of preventing, reducing, ameliorating, mitigating, inhibiting, treating and/or reversing one or more symptoms associated with a neurodevelopmental disorder related to prenatal maternal immune activation (MIA) in an individual in need thereof comprising administering to said individual an agent that increases the level of epoxy-fatty acids (EpFAs), wherein said individual experienced maternal immune activation one or more times during gestation. In some embodiments, the methods comprise administering to the subject an agent that increases the level of epoxy-fatty acids, as a sole active agent or co-administered with a second agent.

In one aspect, provided are methods of preventing, reducing, ameliorating, mitigating, inhibiting, treating and/or reversing autism spectrum disorder (ADS) an individual comprising administering to said individual an agent that increases the level of epoxy-fatty acids. In some embodiments, prior to administration of the agent that increases the level of epoxy-fatty acids, the individual is diagnosed as having experienced maternal immune activation during gestation. In some embodiments, prior to administration of the agent that increases the level of epoxy-fatty acids, the individual has been diagnosed as having experienced exposure to a toxin during gestation. In some embodiments, prior to administration of the agent that increases the level of epoxy-fatty acids, the individual has been diagnosed as having autism spectrum disorder.

In one aspect, provided are methods of preventing, reducing, ameliorating, mitigating, inhibiting, treating and/or reversing schizophrenia an individual comprising administering to said individual an agent that increases the level of epoxy-fatty acids. In some embodiments, prior to administration of the agent that increases the level of epoxy-fatty acids, the individual is diagnosed as having experienced maternal immune activation during gestation. In some embodiments, prior to administration of the agent that increases the level of epoxy-fatty acids, the individual has been diagnosed as having experienced exposure to a toxin during gestation. In some embodiments, prior to administration of the agent that increases the level of epoxy-fatty acids, the individual has been diagnosed as having schizophrenia.

In another aspect, provided are methods for maintaining parvalbumin (PV) and/or glutamic acid decarboxylase ($GAD_{67}$) immunoreactivity in the medial prefrontal cortex (mPFC) of a subject comprising administering to said subject an agent that increases the level of epoxy-fatty acids.

With respect to embodiments of the methods, in some embodiments, the agent that increases the level of epoxy-fatty acids comprises one or more epoxy-fatty acids. In varying embodiments, the epoxy-fatty acids are selected from the group consisting of cis-epoxyeicosatrienoic acids ("EETs"), epoxides of linoleic acid, epoxides of eicosapentaenoic acid ("EPA"), epoxides of docosahexaenoic acid ("DHA"), epoxides of cis-7,10,13,16,19-docosapentaenoic acid, and mixtures thereof. In varying embodiments, the agent that agent that increases the level of epoxy-fatty acids is an inhibitor of soluble epoxide hydrolase ("sEH"). In varying embodiments, the inhibitor of sEH comprises an inhibitory nucleic acid that specifically targets soluble epoxide hydrolase ("sEH"). In varying embodiments, the inhibitory nucleic acid is selected from the group consisting of short interfering RNA (siRNA), short hairpin RNA (shRNA), small temporal RNA (stRNA), and micro-RNA (miRNA). In varying embodiments, the inhibitor of sEH comprises a primary or central pharmacophore selected from the group consisting of a urea, a carbamate, or an amide. In varying embodiments, the inhibitor of sEH comprises a cyclohexyl moiety, aromatic moiety, substituted aromatic moiety or alkyl moiety attached to the pharmacophore. In varying embodiments, the inhibitor of sEH comprises a cyclohexyl ether moiety attached to the pharmacophore. In varying embodiments, the inhibitor of sEH comprises a phenyl ether or piperidine moiety attached to the pharmacophore. In varying embodiments, the inhibitor of sEH comprises a polyether secondary pharmacophore. In varying embodiments, the inhibitor of sEH has an $IC_{50}$ of less than about 100 μM. In varying embodiments, the inhibitor of sEH has an $IC_{50}$ of less than about 50 μM. In varying embodiments, the inhibitor of sEH is selected from the group consisting of:

a) 3-(4-chlorophenyl)-1-(3,4-dichlorphenyl)urea or 3,4,4'-trichlorocarbanilide (TCC; compound 295);
b) 12-(3-adamantan-1-yl-ureido) dodecanoic acid (AUDA; compound 700);
c) 1-adamantanyl-3-{5-[2-(2-ethoxyethoxy)ethoxylpentyl]}urea (AEPU; compound 950);
d) 1-(1-acetypiperidin-4-yl)-3-adamantanylurea (APAU; compound 1153);
e) trans-4-[4-(3-Adamantan-1-yl-ureido)-cyclohexyloxy]-benzoic acid (t-AUCB; compound 1471);
f) cis-4-[4-(3-Adamantan-1-yl-ureido)-cyclohexyloxy]-benzoic acid (c-AUCB; compound 1686);
g) 1-(1-methylsulfonyl-piperidin-4-yl)-3-(4-trifluoromethoxy-phenyl)-urea (TUPS; compound 1709);
h) trans-4-{4-[3-(4-Trifluoromethoxy-phenyl)-ureido]-cyclohexyloxy}-benzoic acid (t-TUCB; compound 1728);
i) 1-trifluoromethoxyphenyl-3-(1-propionylpiperidin-4-yl) urea (TPPU; compound 1770);
j) 1-(1-ethylsulfonyl-piperidin-4-yl)-3-(4-trifluoromethoxy-phenyl)-urea (TUPSE; compound 2213);
k) 1-(1-(cyclopropanecarbonyl)piperidin-4-yl)-3-(4-(trifluoromethoxy)phenyl)urea (CPTU; compound 2214);
l) trans-N-methyl-4-[4-(3-Adamantan-1-yl-ureido)-cyclohexyloxy]-benzamide (t-MAUCB; compound 2225);
m) trans-N-methyl-4-[4-((3-trifluoromethyl-4-chlorophenyl)-ureido)-cyclohexyloxy]-benzamide (t-MTCUCB; compound 2226);
n) cis-N-methyl-4-{4-[3-(4-trifluoro methoxy-phenyl)-ureido]-cyclohexyloxy}-benzamide (c-MTUCB; compound 2228);
o) 1-cycloheptyl-3-(3-(1,5-diphenyl-1H-pyrazol-3-yl) propyl)urea (compound 2247);
p) trans-2-(4-(4-(3-(4-trifluoromethoxy-phenyl)-ureido)-cyclohexyloxy)-benzamido)-acetic acid (compound 2283);
q) N-(methylsulfonyl)-4-(trans-4-(3-(4-trifluoromethoxy-phenyl)-ureido)-cyclohexyloxy)-benzamide (compound 2728);
r) 1-(trans-4-(4-(1H-tetrazol-5-yl)-phenoxy)-cyclohexyl)-3-(4-(trifluoromethoxy)-phenyl)-urea (compound 2806);
s) 4-(trans-4-(3-(2-fluorophenyl)-ureido)-cyclohexyloxy)-benzoic acid (compound 2736);
t) 4-(4-(3-(4-(trifluoromethoxy)-phenyl)-ureido)-phenoxy)-benzoic acid (compound 2803);
u) 4-(3-fluoro-4-(3-(4-(trifluoromethoxy)-phenyl)-ureido)-phenoxy)-benzoic acid (compound 2807);
v) N-hydroxy-4-(trans-4-(3-(4-(trifluoromethoxy)-phenyl)-ureido)-cyclohexyloxy)-benzamide (compound 2761);
w) (5-methyl-2-oxo-1,3-dioxol-4-yl)methyl 4-((1r,4r)-4-(3-(4-(trifluoromethoxy)-phenyl)-ureido)-cyclohexyloxy)-benzoate (compound 2796);
x) 1-(4-oxocyclohexyl)-3-(4-(trifluoromethoxy)-phenyl)-urea (compound 2809);
y) methyl 4-(4-(3-(4-(trifluoromethoxy)-phenyl)-ureido)-cyclohexylamino)-benzoate (compound 2804);
z) 1-(4-(pyrimidin-2-yloxy)-cyclohexyl)-3-(4-(trifluoromethoxy)-phenyl)-urea (compound 2810);
aa) 4-(trans-4-(3-(4-(difluoromethoxy)-phenyl)-ureido)-cyclohexyloxy)-benzoic acid (compound 2805); and
bb) (1R,3S)—N-(4-cyano-2-(trifluoromethyl)benzyl)-3-((4-methyl-6-(methylamino)-1,3,5-triazin-2-yl)amino)cyclohexane-1-carboxamide (GSK2256294A).

BRIEF DESCRIPTION OF THE DRAWINGS

FIG. 4A-E Effects of TPPU on behavioral abnormalities and the reduction of PV-IR and $GAD_{67}$-IR in the mPFC of adult offspring after MIA. (A): Schedule of treatment and brain collection. Saline or poly(I:C) (5 mg/kg/day for 6 days) was administered i.p. into pregnant mice. Vehicle or TPPU (15 mg/L) in drinking water was treated into juvenile offspring from P28 to P56. Subsequently, all mice received normal water. Locomotion and NORT were performed after 10 weeks. Brain for immunohistochemistry was collected at P72. (B): Locomotion test. Data are shown as mean±S.E.M. (n=9-13). N.S.: not significant. (C): NORT: Decreased exploratory preference of adult offspring after prenatal poly (I:C) exposure was significantly attenuated by TPPU in drinking water. Data are shown as mean±S.E.M. (n=9-13). ***$P<0.01$ compared to poly(I:C)+vehicle group. N.S.: not significant. (D): PV-immunohistochemistry: Decreased PV-IR in the PrL of mPFC of adult offspring after prenatal poly(I:C) exposure was significantly attenuated by TPPU in drinking water. Data are shown as mean±S.E.M. (n=7 or 8). *$P<0.05$, $P<0.01$, *$P<0.01$ compared to poly(I:C)+vehicle group. N.S.: not significant. (E): $GAD_{67}$-immunohistochemistry: Decreased $GAD_{67}$-IR in the PrL of mPFC of adult offspring after prenatal poly(I:C) exposure was significantly attenuated by TPPU in drinking water. Data are shown as mean±S.E.M. (n=7 or 8). *$P<0.05$, **$P<0.01$ compared to poly(I:C)+vehicle group. N.S.: not significant.

Figure 5A:
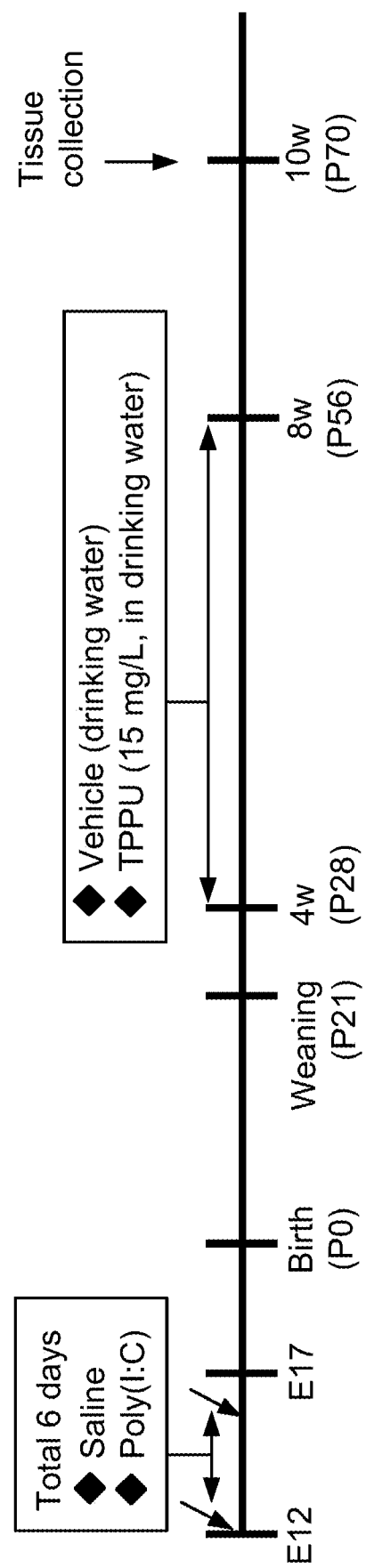
Figure 5B:
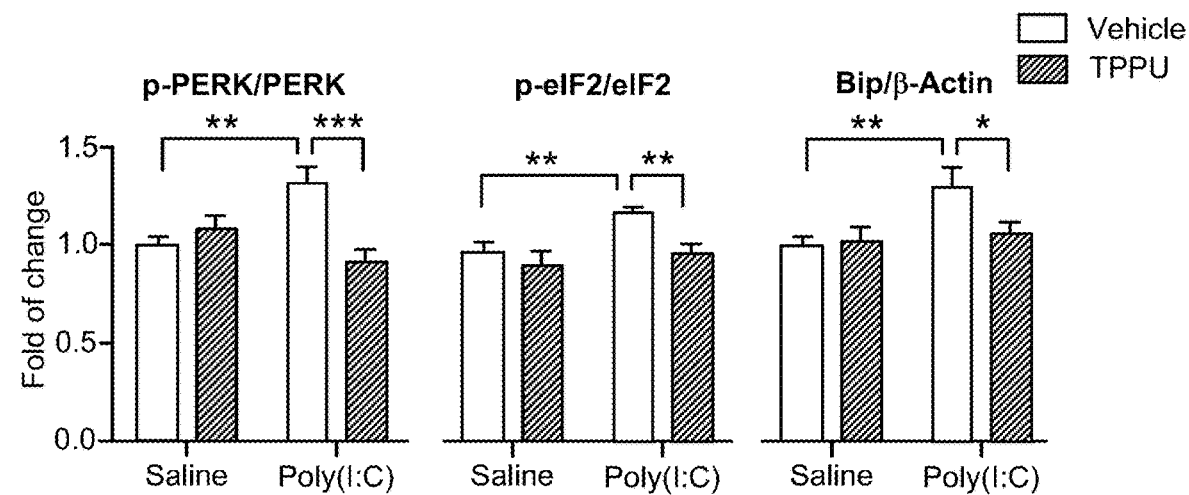
Figure 5B:
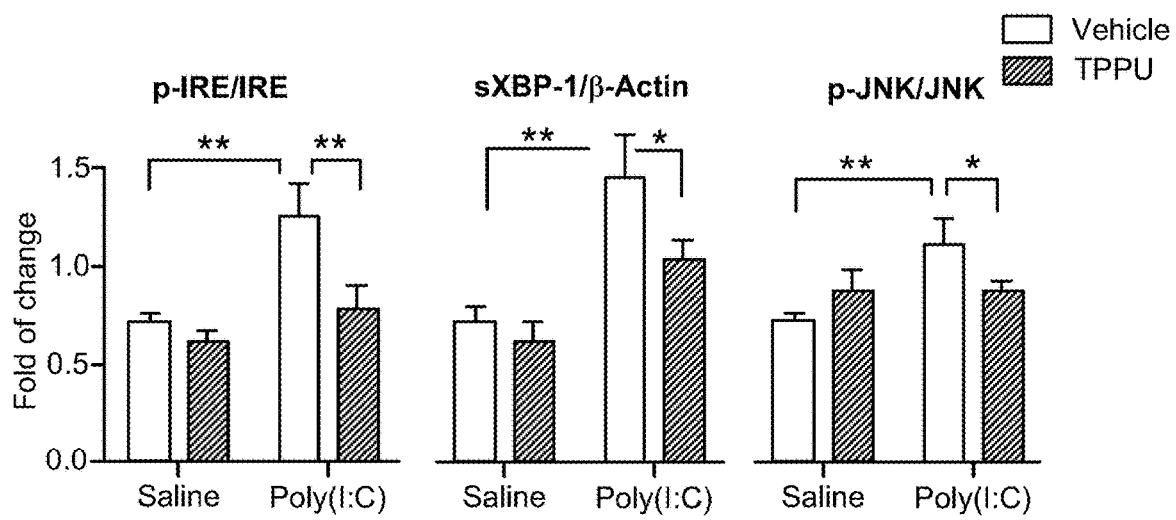
Figure 5B:
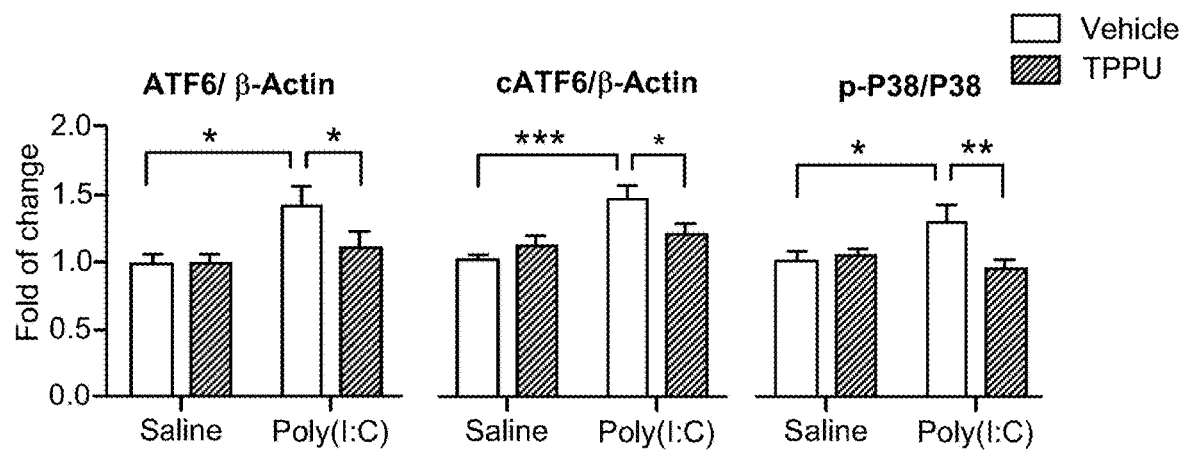

FIG. 5A-B Effects of TPPU on elevated ER stress in the adult offspring after MIA. (A): Schedule of treatment and brain collection. Saline or poly(I:C) (5 mg/kg/day for 6 days) was administered i.p. into pregnant mice. Vehicle or TPPU (15 mg/L) in drinking water was treated into juvenile offspring from P28 to P56. Subsequently, all mice received normal water. PFC from brain was collected at P72. (B): We examined the effects of TPPU in drinking water (from P28 to P56) on markers of ER stress in the PFC from adult offspring after postnatal poly(I:C) exposure. Data are shown as mean±S.E.M. (n=5-7). *$P<0.05$, $P<0.01$, *$P<0.001$ compared to poly(I:C)+vehicle group.

FIG. 6A-E Effects of TPPU on behavioral abnormalities and the reduction of PV-IR in the mPFC of juvenile offspring after MIA. (A): Schedule of treatment and brain collection. Saline or poly(I:C) (5 mg/kg/day for 6 days) was administered i.p. into pregnant mice. Vehicle or TPPU (15 mg/L) in drinking water was administered to pregnant mice from E12 to P21. Subsequently, all mice received normal water. Locomotion and NORT were performed after P28. Brain for immunohistochemistry was collected after behavioral tests. (B): Locomotion test. Data are shown as mean±S.E.M. (n=7-11). N.S.: not significant. (C): NORT: Decreased exploratory preference of juvenile offspring after prenatal poly(I:C) exposure was significantly attenuated by TPPU in drinking water. Data are shown as mean±S.E.M. (n=7-11). *$P<0.05$, **$P<0.01$ compared to poly(I:C)+vehicle group. N.S.: not significant. (D): Three-chamber social interaction test: Social interaction deficits in juvenile offspring after prenatal poly(I:C) exposure was significantly attenuated by TPPU in drinking water. Data are shown as mean±S.E.M. (n=10-17). *$P<0.05$, ***$P<0.001$ compared to poly(I:C)+vehicle group. N.S.: not significant. (E): PV-immunohistochemistry: Decreased PV-IR in the PrL of mPFC of juvenile offspring after prenatal poly(I:C) exposure was significantly attenuated by TPPU in drinking water. Data are shown as mean±S.E.M. (n=6-8). *$P<0.05$, **$P<0.01$ compared to poly(I:C)+vehicle group. N.S.: not significant.

FIG. 7A-E General and behavioral data of mother and juvenile offspring after maternal glyphosate exposure. (A): Schedule of treatment and behavioral tests. Water or glyphosate [0.038% (or 0.1% Roundup®)-0.38% (or 1.0% Roundup®] were given to pregnant mice. (B): Change of body weight of mothers (n=3-6). (C): Locomotion. Data are shown as mean±S.E.M. (n=10). (D): Three chamber social interaction test. Data are shown as mean±S.E.M. (n=6). (E): Forced swimming test. Data are shown as mean±S.E.M. (n=10). N.S.: not significant.

FIG. 8A-K Social interaction deficits, increased expression of sEH and decreased PV-immunoreactivity in the brain from juvenile offspring after maternal glyphosate exposure. (A): Schedule of treatment, behavioral tests and sample collection. (B): Change of body weight of pregnant mothers (n=6). (C): Blood levels of glyphosate in the mothers and offspring at P21. Data are shown as mean±S.E.M. (mother n=7, offspring n=8). (D): Locomotion. Data are shown as mean±S.E.M. (n=7 or 8). (E): Novel object recognition test (NORT). Data are shown as mean±S.E.M. (n=8). (F): Prepulse inhibition (PPI) test. Data are shown as mean±S.E.M. (n=8). (G): Three chamber social interaction test. Data are shown as mean±S.E.M. (n=6 or 7). (H): Protein expression of sEH in the PFC, hippocampus, and striatum of mothers. Data are shown as mean±S.E.M. (n=4 or 5). (I): Protein expression of sEH in the PFC, hippocampus, and striatum from juvenile offspring (P28). Data are shown as mean±S.E.M. (n=10). (J): Gene expression of Ephx2 mRNA in the mouse brain regions from juvenile offspring (P28). Data are shown as mean±S.E.M. (n=8). (K): PV-immunoreactivity in the prelimbic area (PrL) and imfralimbic (IL) of mPFC. The values represent the mean±S.E.M. (n=8). *$P<0.05$, $P<0.01$, *$P<0.001$ compared to control group (Student t-test). N.S.: not significant.

Figure 9A:
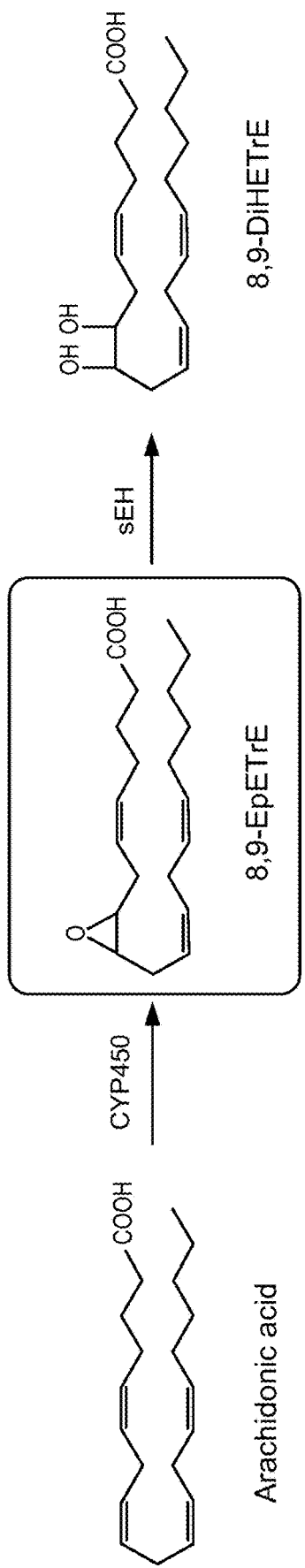
Figure 9B:
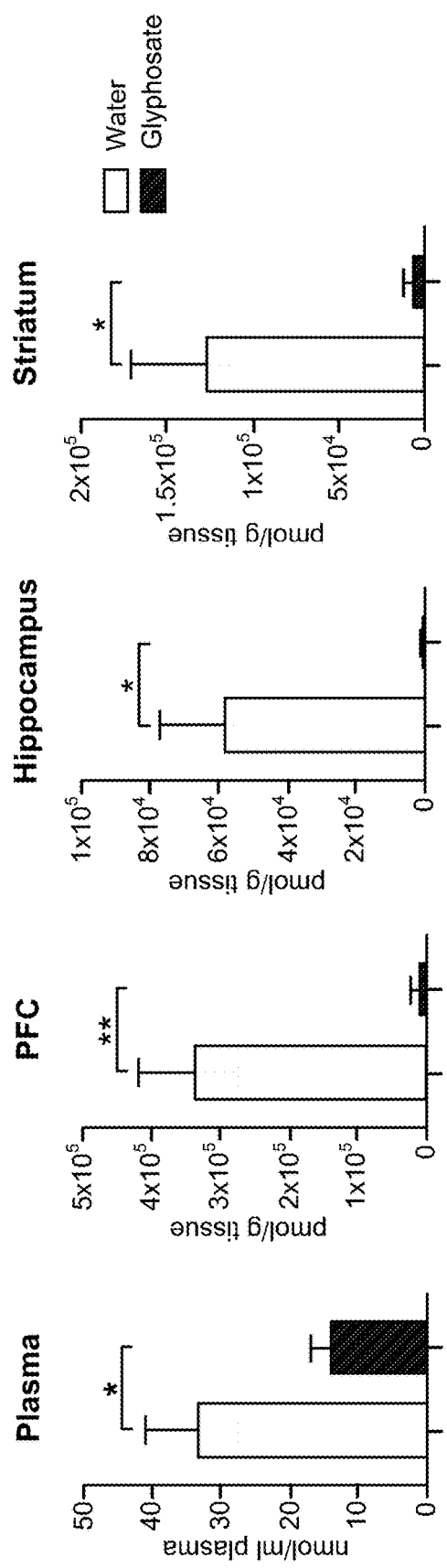

FIG. 9A-B Oxylipin analysis of blood and brain regions. (A): Arachidonic acid is metabolized to 8,9-EpETrE by P450. Subsequently, 8,9-EpETrE is metabolized to 8,9-DiHETrE by sEH. (B): Levels of 8,9-EpETrE in the plasma, PFC, hippocampus, and striatum from juvenile offspring (P28). The values represent the mean±S.E.M. (n=8-10). *$P<0.05$, **$P<0.01$ compared to control group (Student t-test). N.D.: not detected. N.S.: not significant.

Figure 10A:
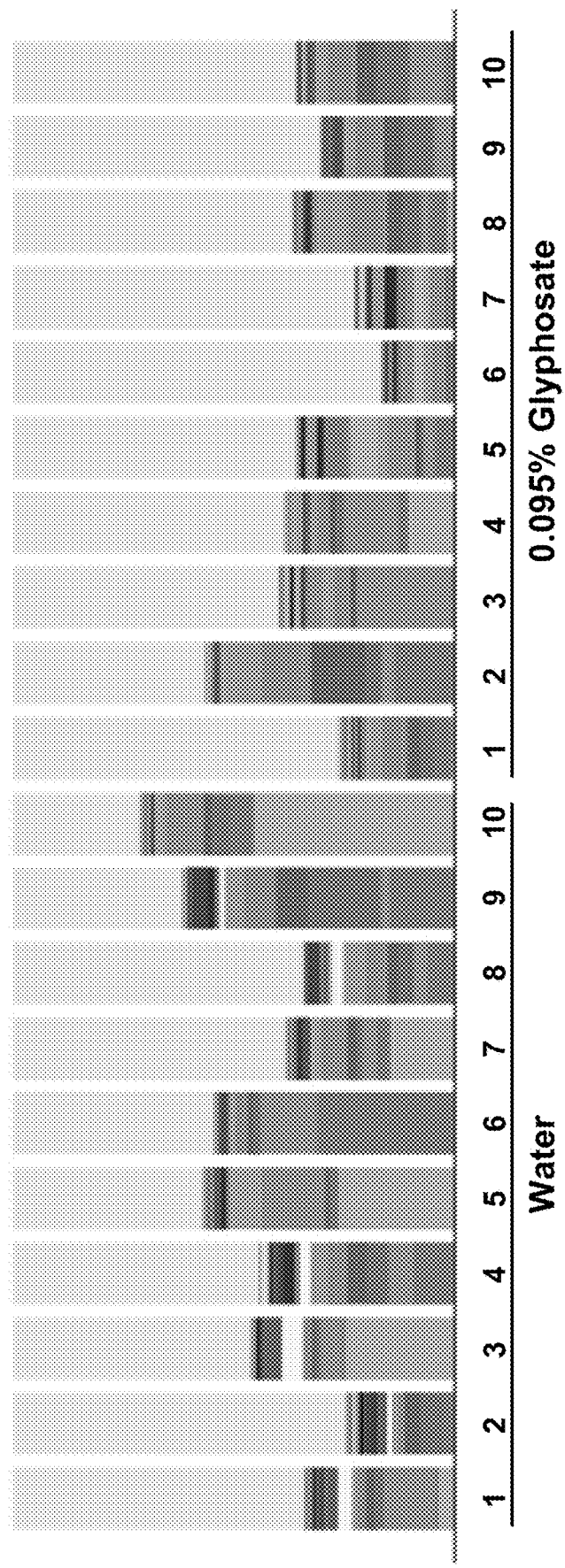
Figure 10A:
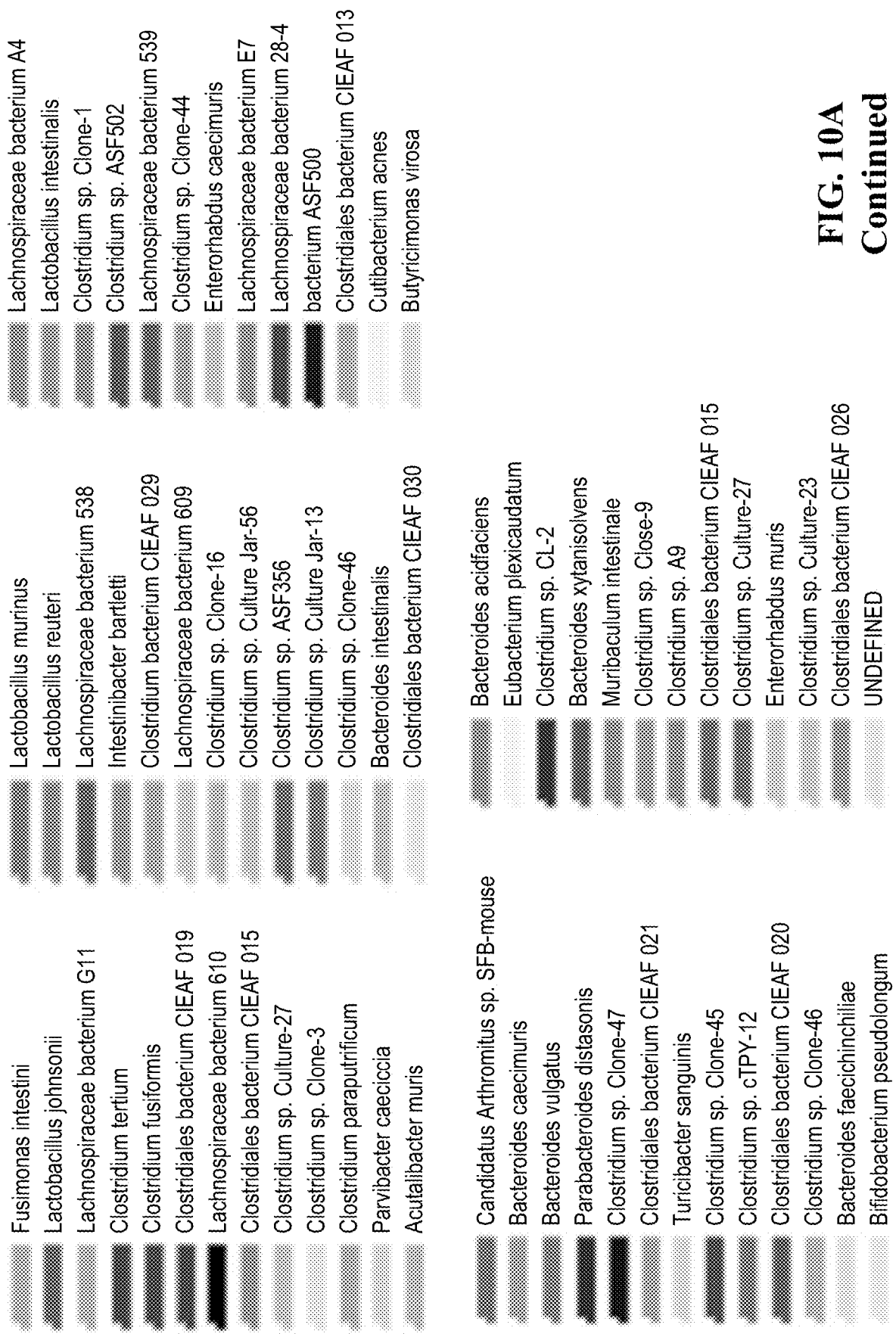
Figure 10B:
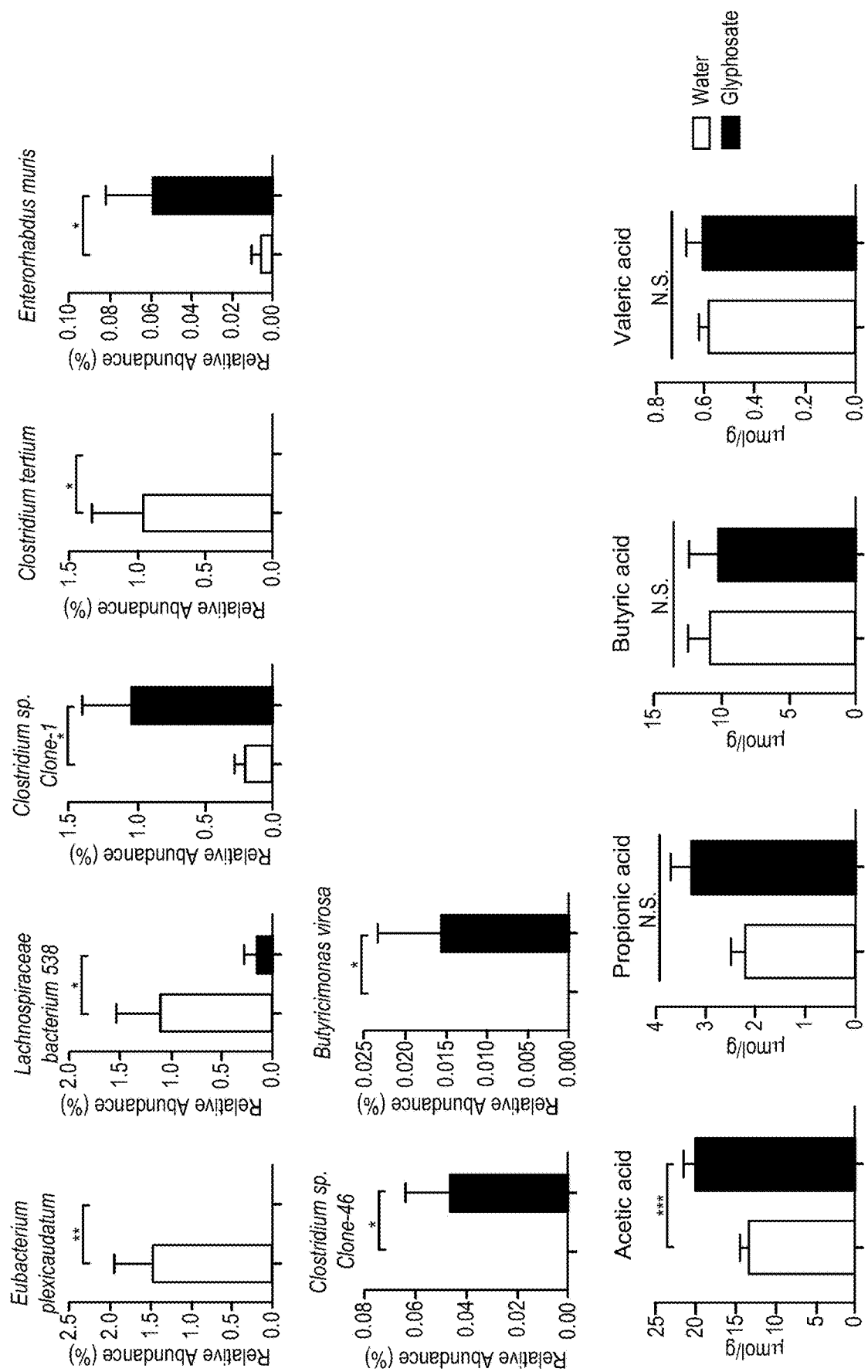

FIG. 10A-B Composition of gut microbiota in fecal samples of juvenile offspring. (A): Histogram of microbiota at species level of offspring (P28). (B): Several bacteria were significantly altered in the offspring after maternal glyphosate exposure. Data are shown as mean±S.E.M. (n=10) *$P<0.05$, **$P<0.01$ compared to control group (Student t-test).

FIG. 11A-D Effects of TPPU on ASD-like behavioral abnormalities in juvenile offspring after maternal glyphosate exposure. (A): Schedule of treatment and behavioral tests. Water or glyphosate (0.095%) was given into pregnant mice. Vehicle (5 ml/kg/day) or TPPU (3 mg/kg/day) was administered orally into pregnant mice from E12 to P21. Subsequently, all mice received normal water. Grooming test and three-chamber social interaction test were performed from P28 to P35. (B): Change of body weight of mothers (n=5 or 6). Two-way ANOVA (glyphosate $F_{1,17}=7.66$, $P=0.013$, TPPU: $F_{1,17}=9.14$, $P=0.008$, interaction $F_{1,17}=1.59$, $P=0.225$). (C): Grooming test. Treatment with TPPU significantly attenuated the increased grooming time in juvenile offspring after maternal glyphosate exposure. Two-way ANOVA (glyphosate $F_{1,36}=14.19$, $P=0.001$, TPPU: $F_{1,36}=25.34$, $P<0.001$, interaction $F_{1,36}=11.31$, $P=0.002$). Data are shown as mean±S.E.M. (n=10). *$P<0.01$ compared to glyphosate+vehicle group. (D): Three-chamber social interaction test. Treatment with TPPU significantly attenuated social interaction deficits in juvenile offspring after maternal glyphosate exposure. Data are shown as mean±S.E.M. (n=8). *$P<0.01$. N.S.: not significant.

DETAILED DESCRIPTION

1. General

Maternal infection during pregnancy increases the risk of neurodevelopmental disorders such as schizophrenia and autism spectrum disorder (ASD) in offspring. In rodents, maternal immune activation (MIA) yields offspring with schizophrenia- and ASD-like behavioral abnormalities. Soluble epoxide hydrolase (sEH) plays a key role in inflammation associated with neurodevelopmental disorders. Here we found higher levels of sEH in the prefrontal cortex (PFC) of juvenile offspring after MIA. Oxylipin analysis showed decreased levels of epoxy-fatty acids (EpFAs) in the PFC of juvenile offspring after MIA, supporting increased activity of sEH in the PFC of juvenile offspring. Furthermore, the expression of sEH (or EPHX2) mRNA in iPSC-derived neurospheres from schizophrenia patients with the 22q11.2 deletion was higher than that of healthy control. Moreover, the expression of EPHX2 mRNA in the postmortem brain samples (Brodmann area 9 and 40) from ASD patients was higher than that of controls. Treatment of TPPU (a potent sEH inhibitor) into juvenile offspring from P28 to P56 could prevent cognitive deficits and loss of parvalbumin (PV)-immunoreactivity in the medial PFC of adult offspring after MIA. In addition, treatment of pregnant mothers with TPPU from E5 to P21 could prevent cognitive deficits, and social interaction deficits and PV-immunoreactivity in the mPFC of juvenile offspring after MIA. These findings suggest that increased activity of sEH in the PFC plays a key role in the etiology of neurodevelopmental disorders in offspring after MIA. Therefore, sEH would represent a promising prophylactic or therapeutic target for neurodevelopmental disorders in offspring after MIA.

The number of children with autism spectrum disorder (ASD) has increased dramatically since the 1980s. We found ASD-like behavioral abnormalities in juvenile offspring after maternal glyphosate exposure. Furthermore, we found higher levels of sEH in the prefrontal cortex (PFC), hippocampus, and striatum of juvenile offspring after maternal glyphosate exposure. Oxylipin analysis showed decreased levels of EpFAs such as 8(9)-EpETrE [8,9-epoxy-5Z,11Z,14Z-eicosatrienoic acid] in the blood, PFC, hippocampus, and striatum of juvenile offspring after maternal glyphosate exposure, supporting increased activity of sEH in the offspring. Moreover, we found abnormal composition of gut microbiota and short chain fatty acids in fecal samples of juvenile offspring after maternal glyphosate exposure. Interestingly, oral administration of TPPU to pregnant mothers from E5 to P21 could prevent ASD-like behaviors such as social interaction deficits and increased grooming time in the juvenile offspring after maternal glyphosate exposure. These findings suggest that maternal glyphosate exposure causes ASD-like behavioral abnormalities and abnormal composition of gut microbiota in juvenile offspring, and that increased activity of sEH plays a key role in ASD-like behaviors in offspring after maternal glyphosate exposure. Therefore, sEH would represent a promising prophylactic target or therapeutic target for ASD in offspring after maternal glyphosate exposure.

Accordingly, the present methods are based, in part, on the discovery that soluble epoxide hydrolase inhibitors can improve symptoms of neurodevelopmental disorders such as autism spectrum disorder. In particular, this disclosure demonstrates a link between offspring exposed to prenatal maternal immune activation (MIA) and the onset of neurodevelopmental disorders in juvenile offspring after MIA. Surprisingly, administration of an agent that increases the level of EpFAs (i.e., an sEH inhibitor, one or more EETs, one or more EEQs, one or more EDPS, or other suitable compounds described herein) can improve, reduce, or prevent the onset of the associated neurodevelopmental disorders.

2. Definitions

Units, prefixes, and symbols are denoted in their Système International d'Unités (SI) accepted form. Numeric ranges are inclusive of the numbers defining the range. Unless otherwise indicated, nucleic acids are written left to right in 5' to 3' orientation; amino acid sequences are written left to right in amino to carboxy orientation. The headings provided herein are not limitations of the various aspects or embodiments, which can be had by reference to the specification as a whole. Accordingly, the terms defined immediately below are more fully defined by reference to the specification in its entirety. Terms not defined herein have their ordinary meaning as understood by a person of skill in the art.

"cis-epoxyeicosatrienoic acids" ("EETs" or "EpETrEs") are epoxides of arachidonic acid that are lipid mediators synthesized by cytochrome P450 enzymes forming epoxides from fatty acid olefins. As discussed further in a separate section below, while the use of unmodified EETs are useful, derivatives of EETs, such as amides and esters (both natural and synthetic), EETs analogs, and EETs optical isomers can all be used in the methods, both in pure form and as mixtures of these forms. For convenience of reference, the term "EETs" as used herein refers to both unmodified EETs as well as derivatives of EETs unless otherwise required by context.

"cis-epoxyeicosatetraenoic acids" ("EEQs" or "EpETEs") are epoxides of eicosapentaenoic acid that are lipid mediators synthesized by cytochrome P450 enzymes forming epoxides from fatty acid olefins. As discussed further in a separate section below, while the use of unmodified EEQs are useful, derivatives of EEQs, such as amides and esters (both natural and synthetic), EEQs analogs, and EEQs optical isomers can all be used in the methods, both in pure form and as mixtures of these forms. For convenience of reference, the term "EEQs" as used herein refers to both unmodified EEQs as well as derivatives of EEQs unless otherwise required by context.

"cis-epoxydocosapentaenoic acids" ("EDPs" or "EpDPEs") are epoxides of docosahexaenoic acid that are lipid mediators synthesized by cytochrome P450 enzymes forming epoxides from fatty acid olefins. As discussed further in a separate section below, while the use of unmodified EDPs are useful, derivatives of EDPs, such as amides and esters (both natural and synthetic), EDPs analogs, and EDPs optical isomers can all be used in the methods, both in pure form and as mixtures of these forms. For convenience of reference, the term "EDPs" as used herein refers to both unmodified EDPs as well as derivatives of EDPs unless otherwise required by context.

"Epoxide hydrolases" ("EH;" EC 3.3.2.3) are enzymes in the alpha beta hydrolase fold family that add water to 3-membered cyclic ethers termed epoxides.

"Soluble epoxide hydrolase" ("sEH"; EC 3.3.2.10) is an epoxide hydrolase which in cells converts EETs to dihydroxy derivatives called dihydroxyeicosatrienoic acids ("DHETs"). The cloning and sequence of the murine sEH is set forth in Grant et al., J. Biol. Chem. 268(23):17628-17633 (1993). The cloning and sequence, and accession numbers of the human sEH sequence are set forth in Beetham et al., Arch. Biochem. Biophys. 305(1):197-201 (1993). The amino acid sequence of human sEH is SEQ ID NO.:1, while the nucleic acid sequence encoding the human sEH is SEQ ID NO.:2. (The sequence set forth as SEQ ID NO.:2 is the coding portion of the sequence set forth in the Beetham et al. 1993 paper and in the NCBI Entrez Nucleotide Browser at accession number L05779, which include the 5' untranslated region and the 3' untranslated region.) The evolution and nomenclature of the gene is discussed in Beetham et al., DNA Cell Biol. 14(1):61-71 (1995). Soluble epoxide hydrolase represents a single highly conserved gene product with over 90% homology between rodent and human (Arand et al., FEBS Lett., 338:251-256 (1994)). Unless otherwise specified, as used herein, the terms "soluble epoxide hydrolase" and "sEH" refer to human sEH.

Unless otherwise specified, as used herein, the term "sEH inhibitor" (also abbreviated as "sEHI" or "sEHi") refers to an inhibitor of human sEH. Preferably, the inhibitor does not also inhibit the activity of microsomal epoxide hydrolase by more than 25% at concentrations at which the inhibitor inhibits sEH by at least 50%, and more preferably does not inhibit mEH by more than 10% at that concentration. For convenience of reference, unless otherwise required by context, the term "sEH inhibitor" as used herein encompasses prodrugs which are metabolized to active inhibitors of sEH. Further for convenience of reference, and except as otherwise required by context, reference herein to a compound as an inhibitor of sEH includes reference to derivatives of that compound (such as an ester of that compound) that retain activity as an sEH inhibitor.

Cytochrome P450 ("CYP450") metabolism produces cis-epoxydocosapentaenoic acids ("EDPs" or "EpDPEs") and cis-epoxyeicosatetraenoic acids ("EEQs" or "EpETEs") from docosahexaenoic acid ("DHA") and eicosapentaenoic acid ("EPA"), respectively. These epoxides are known endothelium-derived hyperpolarizing factors ("EDHFs"). These EDHFs, and others yet unidentified, are mediators released from vascular endothelial cells in response to acetylcholine and bradykinin, and are distinct from the NOS—(nitric oxide) and COX-derived (prostacyclin) vasodilators. Overall cytochrome P450 (CYP450) metabolism of polyunsaturated fatty acids produces epoxides, such as EETs, EEQs, and EDPs which are prime candidates for the active mediator(s). 14(15)-EpETrE, for example, is derived via epoxidation of the 14,15-double bond of EPA and is the ω-3 homolog of 14(15)-EpETrE ("14(15)EET") derived via epoxidation of the 14,15-double bond of arachidonic acid.

"$IC_{50}$" refers to the concentration of an agent required to inhibit enzyme activity by 50%.

"Micro-RNA" ("miRNA") refers to small, noncoding RNAs of 18-25 nt in length that negatively regulate their complementary mRNAs at the posttranscriptional level in many eukaryotic organisms. See, e.g., Kurihara and Watanabe, Proc Natl Acad Sci USA 101(34):12753-12758 (2004). Micro-RNA's were first discovered in the roundworm *C. elegans* in the early 1990s and are now known in many species, including humans. As used herein, it refers to exogenously administered miRNA unless specifically noted or otherwise required by context.

The term "therapeutically effective amount" refers to that amount of the compound being administered sufficient to prevent or decrease the development of one or more of the symptoms of the disease, condition or disorder being treated.

The terms "prophylactically effective amount" and "amount that is effective to prevent" refer to that amount of drug that will prevent or reduce the risk of occurrence of the biological or medical event that is sought to be prevented. In many instances, the prophylactically effective amount is the same as the therapeutically effective amount.

"Subtherapeutic dose" refers to a dose of a pharmacologically active agent(s), either as an administered dose of pharmacologically active agent, or actual level of pharmacologically active agent in a subject that functionally is insufficient to elicit the intended pharmacological effect in itself (e.g., to obtain analgesic, anti-inflammatory, and/or anti-fibrotic effects), or that quantitatively is less than the established therapeutic dose for that particular pharmacological agent (e.g., as published in a reference consulted by a person of skill, for example, doses for a pharmacological agent published in the Physicians' Desk Reference, 69th Ed., 2015, PDR Network or Brunton, et al., Goodman & Gilman's The Pharmacological Basis of Therapeutics, 12th edition, 2010, McGraw-Hill Professional). A "subtherapeutic dose" can be defined in relative terms (i.e., as a percentage amount (less than 100%) of the amount of pharmacologically active agent conventionally administered). For example, a subtherapeutic dose amount can be about 1% to about 75% of the amount of pharmacologically active agent conventionally administered. In some embodiments, a subtherapeutic dose can be about 75%, 50%, 30%, 25%, 20%, 10% or less, than the amount of pharmacologically active agent conventionally administered.

The terms "controlled release," "sustained release," "extended release," and "timed release" are intended to refer interchangeably to any drug-containing formulation in which release of the drug is not immediate, i.e., with a "controlled release" formulation, oral administration does not result in immediate release of the drug into an absorption pool. The terms are used interchangeably with "nonimmediate release" as defined in Remington: The Science and Practice of Pharmacy, University of the Sciences in Philadelphia, Eds., 21$^{st}$ Ed., Lippencott Williams & Wilkins (2005).

The terms "sustained release" and "extended release" are used in their conventional sense to refer to a drug formulation that provides for gradual release of a drug over an extended period of time, for example, 12 hours or more, and that preferably, although not necessarily, results in substantially steady-state blood levels of a drug over an extended time period.

As used herein, the term "delayed release" refers to a pharmaceutical preparation that passes through the stomach intact and dissolves in the small intestine.

As used herein, "synergy" or "synergistic" interchangeably refer to the combined effects of two active agents that are greater than their additive effects. Synergy can also be achieved by producing an efficacious effect with combined inefficacious doses of two active agents. The measure of synergy is independent of statistical significance.

The terms "systemic administration" and "systemically administered" refer to a method of administering agent (e.g., an agent that increases epoxy-fatty acids (e.g., an inhibitor of sEH, an epoxy-fatty acid, and mixtures thereof; optionally co-administered with a second agent (e.g., antidepressant, anti-psychotic, anxiolytic)) to a mammal so that the agent/cells is delivered to sites in the body, including the targeted site of pharmaceutical action, via the circulatory system. Systemic administration includes, but is not limited to, oral, intranasal, rectal and parenteral (i.e., other than through the alimentary tract, such as intramuscular, intravenous, intra-arterial, transdermal and subcutaneous) administration.

The term "co-administration" refers to the presence of both active agents/cells in the blood or body at the same time. Active agents that are co-administered can be delivered concurrently (i.e., at the same time) or sequentially.

The phrase "cause to be administered" refers to the actions taken by a medical professional (e.g., a physician), or a person controlling medical care of a subject, that control and/or permit the administration of the agent(s)/compound(s)/cell(s) at issue to the subject. Causing to be administered can involve diagnosis and/or determination of an appropriate therapeutic or prophylactic regimen, and/or prescribing particular agent(s)/compounds/cell(s) for a subject. Such prescribing can include, for example, drafting a prescription form, annotating a medical record, and the like.

The terms "patient," "subject" or "individual" refers to a human or non-human mammal, including primates (e.g., macaque, pan troglodyte, pongo), a domesticated mammal (e.g., felines, canines), an agricultural mammal (e.g., bovine, ovine, porcine, equine) and a laboratory mammal or rodent (e.g., rattus, murine, lagomorpha, hamster). In some embodiments, the term "patient," "subject" or "individual" refers to a human. In some embodiments, the term "patient," "subject" or "individual" refers to a non-human mammal.

The term "mitigating" refers to reduction or elimination of one or more symptoms of that pathology or disease, and/or a reduction in the rate or delay of onset or severity of one or more symptoms of that pathology or disease, and/or the prevention of that pathology or disease.

The terms "inhibiting," "reducing," "decreasing" refers to inhibiting the disease condition of interest (e.g., neurodevelopmental disorder, e.g., schizophrenia, autism) in a mammalian subject by a measurable amount using any method known in the art. For example, one or more symptoms of a neurodevelopmental disorder is inhibited, reduced or decreased if an indicator of the neurodevelopmental disorder is reduced by a measurable amount, either quantitatively or qualitatively, e.g., in comparison to the same inflammatory indicator prior to administration of an agent that increases epoxy-fatty acids (e.g., an inhibitor of sEH, an epoxy-fatty acid, a mimic of an epoxy-fatty acid, and mixtures thereof). Qualitative and quantitative measures of neurodevelopmental disorders are known in the art, and described, e.g., in the Diagnostic and Statistical Manual of Mental Disorders, 5th Edition (DSM-5) American Psychiatric Association, American Psychiatric Publishing, 2013 and/or the International Statistical Classification of Diseases and Related Health Problems (ICD)-11 of the World Health Organization (WHO) (available online at http://www.who.int/classifications/icd/en/).

As used herein, the phrase "consisting essentially of" refers to the genera or species of active pharmaceutical agents included in a method or composition, as well as any excipients inactive for the intended purpose of the methods or compositions. In some embodiments, the phrase "consisting essentially of" expressly excludes the inclusion of one or more additional active agents other than the listed active agents, e.g., an agent that increases epoxy-fatty acids (e.g., an inhibitor of sEH, an epoxy-fatty acid, and mixtures thereof) and/or an anti-inflammatory agent.

As used herein, the phrase "maternal immune activation" refers to activation that occurs in a pregnant individual who has been exposed to a pathogen such as a virus, a bacterial, or another immunogenic stimuli that elicits an immune response in the pregnant individual. Additional stimuli that provoke maternal immune activation include, but are not limited to, stress, malnourishment, drug abuse, and alcohol abuse.

The terms "autism spectrum disorder" and "ASD" or "ASDs" are used in this disclosure to refer to a spectrum of disorders characterized by abnormalities of social interactions and communication, as well as restricted interests and repetitive behavior. This spectrum includes, but is not limited to, autistic disorder, Asperger's syndrome, childhood disintegrative disorder, atypical autism or pervasive developmental disorder not otherwise specified (PPD-NOS), Rett syndrome and tuberous sclerosis.

3. Subjects Who May Benefit—Conditions Subject to Treatment

Subjects who may benefit generally have a neurodevelopmental disorder or are at risk of developing a neurodevelopmental disorder due to experiencing maternal immune activation one or more times during gestation.

Maternal immune activation can be triggered by a number of stimuli including a virus, a bacterial, or another immunogenic agent. These stimuli elicit an immune response in the pregnant individual thereby causing maternal immune activation. Additional stimuli that provoke maternal immune activation include, but are not limited to, stress, malnourishment, drug abuse, and alcohol abuse. Without being bound to any specific theory, it is believed that particular proinflammatory proteins released during maternal immune infection alter brain development in the unborn offspring. The altered brain development can cause neurodevelopmental disorders, which include schizophrenia and autism. As reported herein, higher levels of soluble epoxide hydrolase (sEH) were found in particular portions of the brain. Treatment with agents that increase epoxy-fatty acids prevented cognitive and social defects associated with neurodevelopmental disorders.

In some embodiments, exposure to a toxin is the additional stimuli that provokes maternal immune activation. Toxins include harmful chemicals such as alcohol, drugs, pesticides or herbicides. Various pesticides and herbicides are known in the art, each of which are included in the current application. Non-limiting examples of pesticides and herbicides include glyphosate, malathion, pentachloronitrobenzene, parathion, tetrachlorvinphos, propoxur, toxaphene, and metiram. In some embodiments, the herbicide is glyphosate.

Neurodevelopmental disorders are often characterized by children with difficulties with speech, language, memory, motor skills, learning, and/or other neurological functions. Illustrative disorders include autism spectrum disorder (ASD), schizophrenia, Tourette's syndrome, obsessive-compulsive disorder (OCD), attention-deficit/hyperactivity disorder (ADHD), schizotypal disorder, hypogonadotropic hypogonadal syndromes, and cerebral palsy. Without being bound to theory, it has been discovered that increased activity of sEH, particularly in the PFC of individuals, plays a key role in the etiology of neurodevelopmental disorders. Inhibitors of soluble epoxide hydrolase and other agents that increase the levels of epoxy-fatty acids increase levels of epoxyeicosatrienoic acids (EETs) and epoxydocosapentaenoic acids (EDPs), and related compounds can inhibit, attenuate, or prevent the development of neurodevelopmental disorders due to the over activity of sEH. The symptoms of the neurodevelopmental disorder may be actively manifesting, or may be suppressed or controlled (e.g., by medication) or in remission. The subject may or may not have been diagnosed with the disorder, e.g., by a qualified medical or psychiatric practitioner. In some embodiments, the subject is already receiving a treatment regime for the neurodevelopmental disorder, e.g., taking a regime of pharmaceuticals appropriate for the diagnosed disease.

In some embodiments, the neurodevelopmental disorder treated by administration of an agent that increases the level of epoxy-fatty acids is autism spectrum disorder (ASD) or schizophrenia.

In some embodiments, the neurodevelopmental disorder treated by administration of an agent that increases the level of epoxy-fatty acids is schizophrenia.

In some embodiments, the neurodevelopmental disorder treated by administration of an agent that increases the level of epoxy-fatty acids is autism spectrum disorder (ASD).

Autism spectrum disorders are pervasive neurodevelopmental disorders generally associated with the loss of acquired skills are lost and/or the delay in acquiring new skills. Typically, ASDs onset is in early childhood and are associated with varying degrees of dysfunctional communication and social skills, in addition to repetitive and stereotypic behaviors. ASDs include, but are not limited to autistic disorder, Asperger's syndrome, childhood disintegrative disorder, atypical autism or pervasive developmental disorder not otherwise specified (PPD-NOS), Rett syndrome and tuberous sclerosis.

Qualitative and quantitative measures of symptoms and behaviors of neurodevelopmental disorders, including those listed above, are known in the art, and described, e.g., in the Diagnostic and Statistical Manual of Mental Disorders, 5th Edition (DSM-5) American Psychiatric Association, American Psychiatric Publishing, 2013 and/or the International Statistical Classification of Diseases and Related Health Problems (ICD)-11 of the World Health Organization (WHO) (available online at http://www.who.int/classifications/icd/en/).

In some embodiments, the subject is an unborn offspring, a child, a juvenile or an adult. In some embodiments, the juvenile, adolescent or adult experienced prenatal maternal immune activation during gestation. In some embodiments, the subject is an unborn offspring whose mother has experienced maternal immune activation. In such embodiments, the mother is administered an agent that increases the level of epoxy-fatty acids, whereby the fetus also receives exposure said agent. Individuals who are nursing can be administered an agent that increases the level of epoxy-fatty acids directly or the agent that increases the level of epoxy-fatty acids can be administered to the mother, whereby the nursing individual receives the agent through the breast milk of the mother.

In some embodiments, the subject is a mammal, for example, a human or a domesticated mammal (e.g., a canine, a feline, an equine).

4. Agents that Increase Epoxy-Fatty Acids

Agents that increase epoxy-fatty acids include epoxy-fatty acids (e.g., including EETs), and inhibitors of soluble epoxide hydrolase (sEH).

a. Inhibitors of Soluble Epoxide Hydrolase (sEH)

Scores of sEH inhibitors are known, of a variety of chemical structures.

Derivatives in which the urea, carbamate or amide pharmacophore are particularly useful as sEH inhibitors. As used herein, "pharmacophore" refers to the section of the structure of a ligand that binds to the sEH. In various embodiments, the urea, carbamate or amide pharmacophore is covalently bound to both an adamantane and to a 12-carbon chain dodecane. Derivatives that are metabolically stable are preferred, as they are expected to have greater activity in vivo. Selective and competitive inhibition of sEH in vitro by a variety of urea, carbamate, and amide derivatives is taught, for example, by Morisseau et al., Proc. Natl. Acad. Sci. U.S.A, 96:8849-8854 (1999), which provides substantial guidance on designing urea derivatives that inhibit the enzyme.

Derivatives of urea are transition state mimetics that form a preferred group of sEH inhibitors. Within this group, N, N'-dodecyl-cyclohexyl urea (DCU), is preferred as an inhibitor, while N-cyclohexyl-N'-dodecylurea (CDU) is particularly preferred. Some compounds, such as dicyclohexylcarbodiimide (a lipophilic diimide), can decompose to an active urea inhibitor such as DCU. Any particular urea derivative or other compound can be easily tested for its ability to inhibit sEH by standard assays, such as those discussed herein. The production and testing of urea and carbamate derivatives as sEH inhibitors is set forth in detail in, for example, Morisseau et al., Proc Natl Acad Sci (USA) 96:8849-8854 (1999).

N-Adamantyl-N'-dodecyl urea ("ADU") is both metabolically stable and has particularly high activity on sEH. (Both the 1- and the 2-adamantyl ureas have been tested and have about the same high activity as an inhibitor of sEH. Thus, isomers of adamantyl dodecyl urea are preferred inhibitors. It is further expected that N, N'-dodecyl-cyclohexyl urea (DCU), and other inhibitors of sEH, and particularly dodecanoic acid ester derivatives of urea, are suitable for use in the methods. Preferred inhibitors include without limitation:

12-(3-Adamantan-1-yl-ureido)dodecanoic acid (AUDA)

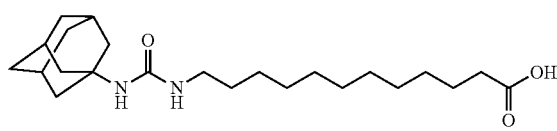 [SMILES: O=C(O)CCCCCCCCCCCNC(=O)NC12CC3CC(CC(C3)C1)C2]

12-(3-Adamantan-1-yl-ureido)dodecanoic acid butyl ester (AUDA-BE)

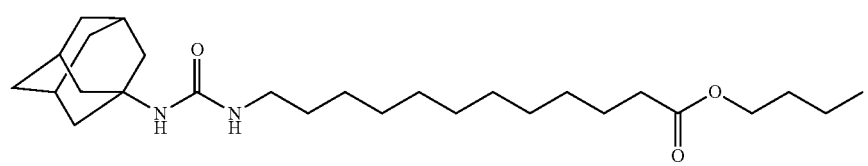 [SMILES: CCCCOC(=O)CCCCCCCCCCCNC(=O)NC12CC3CC(CC(C3)C1)C2]

Adamantan-1-yl-3-{5-[2-(2-ethoxyethoxy)ethoxy]pentyl}urea (Compound 950, also referred to herein as "AEPU"), and

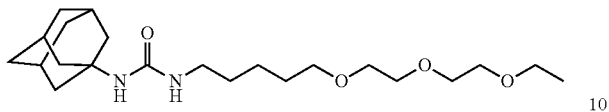

Another preferred group of inhibitors are piperidines. The following Tables sets forth some exemplary inhibitors of sEH and their ability to inhibit sEH activity of the human enzyme and sEH from equine, ovine, porcine, feline and canine, expressed as the amount needed to reduce the activity of the enzyme by 50% (expressed as "$IC_{50}$").

TABLE 1

$IC_{50}$ values for selected alkylpiperidine-based sEH inhibitors against human sEH

|  |  | n = 0 | | n = 1 | |
|---|---|---|---|---|---|
| R: |  | Compound | $IC_{50}$ (μM)[a] | Compound | $IC_{50}$ (μM)[a] |
|  | H | I | 0.30 | II | 4.2 |
|  | (propyl) | 3a | 3.8 | 4.a | 3.9 |
|  | (butyl) | 3b | 0.81 | 4b | 2.6 |
|  | (pentyl) | 3c | 1.2 | 4c | 0.61 |
|  | (benzyl) | 3d | 0.01 | 4d | 0.11 |

[a] As determined via a kinetic fluorescent assay.

TABLE 2 sEH inhibitors

| Structure | Name | sEHi # |
|---|---|---|
|  | 3-(4-chlorophenyl)-1-(3,4-dichlorphenyl)urea or 3,4,4'-trichlorocarbanilide | 295 (TCC) |
| 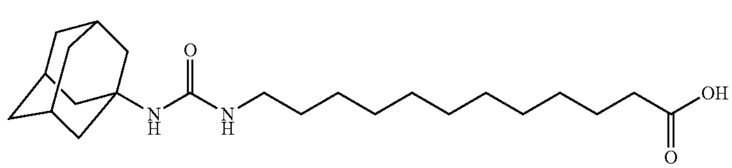 [SMILES: O=C(O)CCCCCCCCCCCNC(=O)NC12CC3CC(CC(C3)C1)C2] | 12-(3-adamantan-1-yl-ureido) dodecanoic acid | 700 (AUDA) |

TABLE 2-continued sEH inhibitors

| Structure | Name | sEHi # |
|---|---|---|
| | 1-adamantanyl-3-{5-[2-(2-ethoxyethoxy)-ethoxy]pentyl}urea | 950 (AEPU) |
| 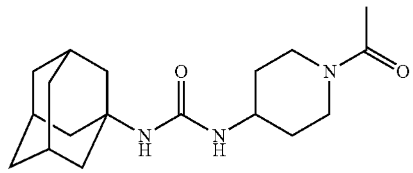 [SMILES: CC(=O)N1CCC(NC(=O)NC23CC4CC(CC(C4)C2)C3)CC1] | 1-(1-acetypiperidin-4-yl)-3-adamantanylurea | 1153 (APAU) |
| 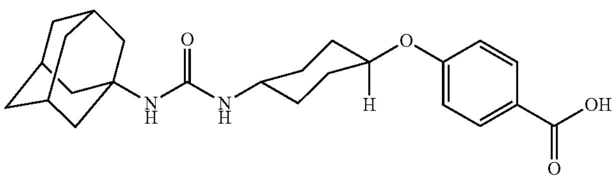 [SMILES: O=C(NC1CCC(Oc2ccc(C(=O)O)cc2)CC1)NC12CC3CC(CC(C3)C1)C2] | trans-4-[4-(3-Adamantan-1-yl-ureido)-cyclohexyloxy]-benzoic acid | 1471 (t-AUCB) |
| 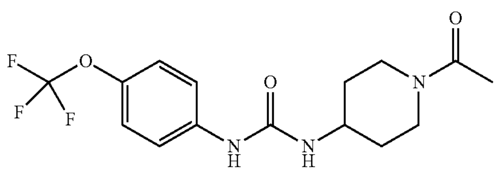 [SMILES: CC(=O)N1CCC(NC(=O)Nc2ccc(OC(F)(F)F)cc2)CC1] | 1-trifluoromethoxy-phenyl-3-(1-acetyl-piperidin-4-yl) urea | 1555 (TPAU) |
| 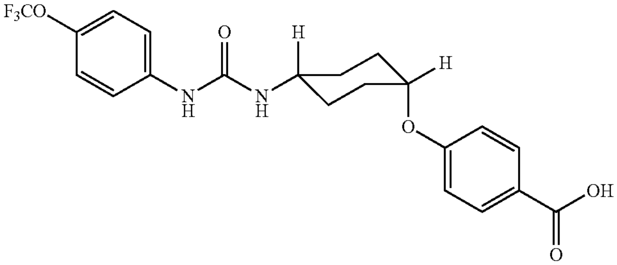 [SMILES: O=C(Nc1ccc(OC(F)(F)F)cc1)NC1CCC(Oc2ccc(C(=O)O)cc2)CC1] | cis-4-[4-(3-Adamantan-1-yl-ureido)-cyclohexyl-oxy]-benzoic acid | 1686 (c-AUCB) |
| 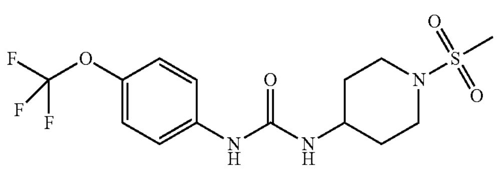 [SMILES: CS(=O)(=O)N1CCC(NC(=O)Nc2ccc(OC(F)(F)F)cc2)CC1] | 1-(1-methylsulfonyl-piperidin-4-yl)-3-(4-trifluoromethoxy-phenyl)-urea | 1709 (TUPS) |
| 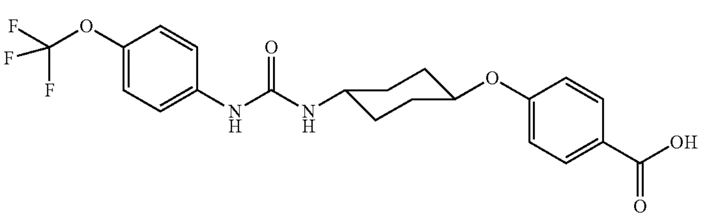 [SMILES: O=C(Nc1ccc(OC(F)(F)F)cc1)NC1CCC(Oc2ccc(C(=O)O)cc2)CC1] | trans-4-{4-[3-(4-Trifluoromethoxy-phenyl)-ureido]-cyclohexyloxy}-benzoic acid | 1728 (t-TUCB) |
| 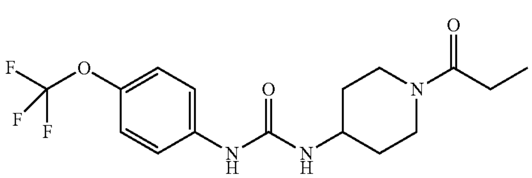 [SMILES: CCC(=O)N1CCC(NC(=O)Nc2ccc(OC(F)(F)F)cc2)CC1] | 1-trifluoromethoxy-phenyl-3-(1-propionyl-piperidin-4-yl) urea | 1770 (TPPU) |

TABLE 2-continued sEH inhibitors

| Structure | Name | sEHi # |
|---|---|---|
| 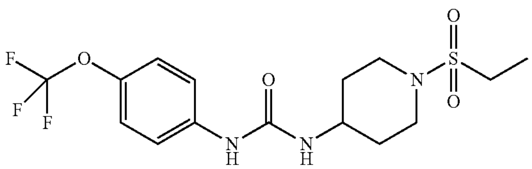 [SMILES: CCS(=O)(=O)N1CCC(NC(=O)Nc2ccc(OC(F)(F)F)cc2)CC1] | 1-(1-ethylsulfonyl-piperidin-4-yl)-3-(4-trifluoromethoxy-phenyl)-urea | 2213 (TUPSE) |
| 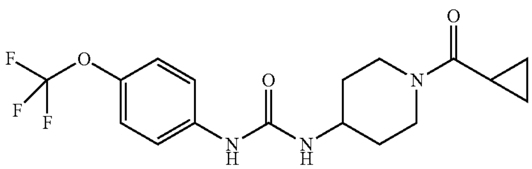 [SMILES: O=C(Nc1ccc(OC(F)(F)F)cc1)NC1CCN(C(=O)C2CC2)CC1] | 1-(1-(cyclopropane-carbonyl)piperidin-4-yl)-3-(4-(trifluoro-methoxy)phenyl)urea | 2214 (CPTU) |
| 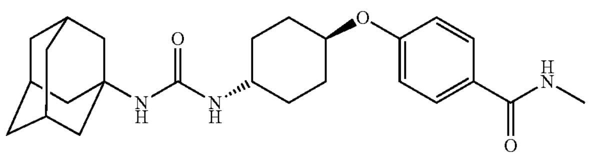 | trans-N-methyl-4-[4-(3-Adamantan-1-yl-ureido)-cyclohexyl-oxy]-benzamide | 2225 (t-MAUCB) |
| 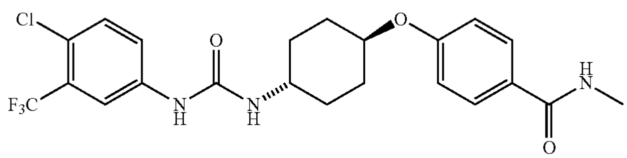 | trans-N-methyl-4-[4-((3-trifluoromethyl-4-chlorophenyl)-ureido)-cyclohexyloxy]-benz-amide | 2226 (t-MTCUCB) |
| 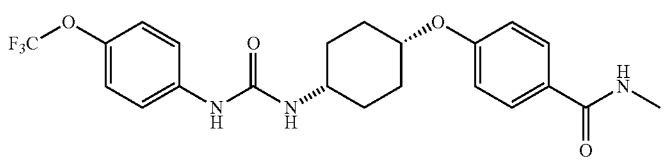 | cis-N-methyl-4-{4-[3-(4-trifluoromethoxy-phenyl)-ureido]-cyclo-hexyloxy}-benzamide | 2228 (c-MTUCB) |
| 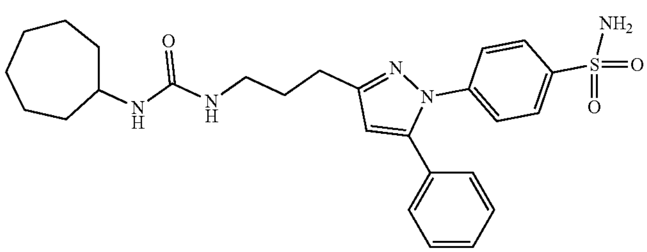 [SMILES: NS(=O)(=O)c1ccc(-n2nc(CCCNC(=O)NC3CCCCCC3)cc2-c2ccccc2)cc1] | 1-cycloheptyl-3-(3-(1,5-diphenyl-1H-pyrazol-3-yl)propyl)urea | 2247 (HDP3U) |

A number of other sEH inhibitors which can be used in the methods and compositions are described in published International Applications PCT/US2015/023048, PCT/US2013/024396, PCT/US2012/025074, PCT/US2011/064474, PCT/US2011/022901, PCT/US2008/072199, PCT/US2007/006412, PCT/US2005/038282, PCT/US2005/08765, PCT/US2004/010298 and U.S. Published Patent Application Publication Nos: 2016/0200683, 2015/0011586, 2014/0088156, 2014/0038923, 2013/0274476, 2013/0143925, 2013/0137726, 2011/0098322, 2005/0026844, each of which is hereby incorporated herein by reference in its entirety for all purposes.

A further inhibitor of soluble epoxide hydrolase useful in the present methods is GSK2256294A (IUPAC/Chemical Name: (1R,3S)—N-(4-cyano-2-(trifluoromethyl)benzyl)-3-((4-methyl-6-(methylamino)-1,3,5-triazin-2-yl)amino)cyclohexane-1-carboxamide; CAS #: 1142090-23-0), described in Podolin, et al., *Prostaglandins Other Lipid Mediat.* (2013) 104-105:25-31, the structure of which is provided below:

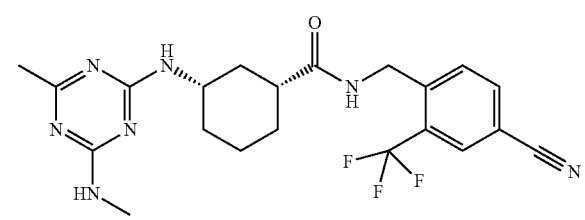 [SMILES: CNc1nc(C)nc(N[C@H]2CCC[C@@H](C(=O)NCc3ccc(C#N)cc3C(F)(F)F)C2)n1]

U.S. Pat. No. 5,955,496 (the '496 patent) also sets forth a number of sEH inhibitors which can be used in the methods. One category of these inhibitors comprises inhibitors that mimic the substrate for the enzyme. The lipid alkoxides (e.g., the 9-methoxide of stearic acid) are an exemplar of this group of inhibitors. In addition to the inhibitors discussed in the '496 patent, a dozen or more lipid alkoxides have been tested as sEH inhibitors and mimics, including the methyl, ethyl, and propyl alkoxides of oleic acid (also known as stearic acid alkoxides), linoleic acid, and arachidonic acid, and all have been found to act as inhibitors of sEH.

In another group of embodiments, the '496 patent sets forth sEH inhibitors that provide alternate substrates for the enzyme that are turned over slowly. Exemplars of this category of inhibitors are phenyl glycidols (e.g., S, S-4-nitrophenylglycidol), and chalcone oxides. The '496 patent notes that suitable chalcone oxides include 4-phenylchalcone oxide and 4-fluourochalcone oxide. The phenyl glycidols and chalcone oxides are believed to form stable acyl enzymes.

Additional inhibitors of sEH suitable for use in the methods are set forth in U.S. Pat. No. 6,150,415 (the '415 patent) and U.S. Pat. No. 6,531,506 (the '506 patent). Two preferred classes of sEH inhibitors are compounds of Formulas 1 and 2, as described in the '415 and '506 patents. Means for preparing such compounds and assaying desired compounds for the ability to inhibit epoxide hydrolases are also described. In particular, the '415 patent describes a spectrophotometric assay for determining the $IC_{50}$ of sEH inhibitors (Dietze et al. "Spectrophotomeric Substrates for Cytosolic Epoxide Hydrolase," *Anal. Biochem*, 216, pp. 176-187, 1994). The '506 patent teaches scores of inhibitors of Formula 1 and some twenty sEH inhibitors of Formula 2, which were shown to inhibit human sEH at concentrations as low as 0.1 µM. Any particular sEH inhibitor can readily be tested to determine whether it will work in the methods by standard assays. Esters and salts of the various compounds discussed above or in the cited patents, for example, can be readily tested by these assays for their use in the methods.

As noted above, chalcone oxides can serve as an alternate substrate for the enzyme. While chalcone oxides have half-lives which depend in part on the particular structure, as a group the chalcone oxides tend to have relatively short half-lives (a drug's half-life is usually defined as the time for the concentration of the drug to drop to half its original value. See, e.g., Thomas, G., Medicinal Chemistry: an introduction, John Wiley & Sons Ltd. (West Sussex, England, 2000)). Since the various uses contemplate inhibition of sEH over differing periods of time which can be measured in days, weeks, or months, chalcone oxides, and other inhibitors which have a half-life whose duration is shorter than the practitioner deems desirable, are preferably administered in a manner which provides the agent over a period of time. For example, the inhibitor can be provided in materials that release the inhibitor slowly. Methods of administration that permit high local concentrations of an inhibitor over a period of time are known, and are not limited to use with inhibitors which have short half-lives although, for inhibitors with a relatively short half-life, they are a preferred method of administration.

In addition to the compounds in Formula 1 of the '506 patent, which interact with the enzyme in a reversible fashion based on the inhibitor mimicking an enzyme-substrate transition state or reaction intermediate, one can have compounds that are irreversible inhibitors of the enzyme. The active structures such as those in the Tables or Formula 1 of the '506 patent can direct the inhibitor to the enzyme where a reactive functionality in the enzyme catalytic site can form a covalent bond with the inhibitor. One group of molecules which could interact like this would have a leaving group such as a halogen or tosylate which could be attacked in an SN2 manner with a lysine or histidine. Alternatively, the reactive functionality could be an epoxide or Michael acceptor such as an α/β-unsaturated ester, aldehyde, ketone, ester, or nitrile.

Further, in addition to the Formula 1 compounds, active derivatives can be designed for practicing the invention. For example, dicyclohexyl thiourea can be oxidized to dicyclohexylcarbodiimide which, with enzyme or aqueous acid (physiological saline), will form an active dicyclohexylurea. Alternatively, the acidic protons on carbamates or ureas can be replaced with a variety of substituents which, upon oxidation, hydrolysis or attack by a nucleophile such as glutathione, will yield the corresponding parent structure. These materials are known as prodrugs or protoxins (Gilman et al., The Pharmacological Basis of Therapeutics, 7th Edition, MacMillan Publishing Company, New York, p. 16 (1985)) Esters, for example, are common prodrugs which are released to give the corresponding alcohols and acids enzymatically (Yoshigae et al., Chirality, 9:661-666 (1997)). The drugs and prodrugs can be chiral for greater specificity. These derivatives have been extensively used in medicinal and agricultural chemistry to alter the pharmacological properties of the compounds such as enhancing water solubility, improving formulation chemistry, altering tissue targeting, altering volume of distribution, and altering penetration. They also have been used to alter toxicology profiles.

There are many prodrugs possible, but replacement of one or both of the two active hydrogens in the ureas described here or the single active hydrogen present in carbamates is particularly attractive. Such derivatives have been extensively described by Fukuto and associates. These derivatives have been extensively described and are commonly used in agricultural and medicinal chemistry to alter the pharmacological properties of the compounds. (Black et al., Journal of Agricultural and Food Chemistry, 21(5):747-751 (1973); Fahmy et al, Journal of Agricultural and Food Chemistry, 26(3):550-556 (1978); Jojima et al., Journal of Agricultural and Food Chemistry, 31(3):613-620 (1983); and Fahmy et al., Journal of Agricultural and Food Chemistry, 29(3):567-572 (1981).)

Such active prodrug derivatives are within the scope of the present invention, and the just-cited references are incorporated herein by reference. Without being bound by theory, it is believed that suitable inhibitors mimic the enzyme transition state so that there is a stable interaction with the enzyme catalytic site. The inhibitors appear to form hydrogen bonds with the nucleophilic carboxylic acid and a polarizing tyrosine of the catalytic site.

In some embodiments, the sEH inhibitor used in the methods taught herein is a "soft drug." Soft drugs are compounds of biological activity that are rapidly inactivated by enzymes as they move from a chosen target site. EETs and simple biodegradable derivatives administered to an area of interest may be considered as soft drugs in that they are likely to be enzymatically degraded by sEH as they diffuse away from the site of interest following administration. Some sEHI, however, may diffuse or be transported following administration to regions where their activity in inhibiting sEH may not be desired. Thus, multiple soft drugs for treatment have been prepared. These include but are not limited to carbamates, esters, carbonates and amides placed in the sEHI, approximately 7.5 angstroms from the carbonyl of the central pharmacophore. These are highly active sEHI that yield biologically inactive metabolites by the action of esterase and/or amidase. Groups such as amides and carbamates on the central pharmacophores can also be used to increase solubility for applications in which that is desirable in forming a soft drug. Similarly, easily metabolized ethers may contribute soft drug properties and also increase the solubility.

In some embodiments, sEH inhibition can include the reduction of the amount of sEH. As used herein, therefore, sEH inhibitors can therefore encompass nucleic acids that inhibit expression of a gene encoding sEH. Many methods of reducing the expression of genes, such as reduction of transcription and siRNA, are known, and are discussed in more detail below.

In various embodiments, a compound with combined functionality to concurrently inhibit sEH and COX-2 is administered. Urea-containing pyrazoles that function as dual inhibitors of cyclooxygenase-2 and soluble epoxide hydrolase are described, e.g., in Hwang, et al., *J Med Chem.* (2011) 28; 54(8):3037-50.

Preferably, the inhibitor inhibits sEH without also significantly inhibiting microsomal epoxide hydrolase ("mEH"). Preferably, at concentrations of 100 µM, the inhibitor inhibits sEH activity by at least 50% while not inhibiting mEH activity by more than 10%. Preferred compounds have an $IC_{50}$ (inhibition potency or, by definition, the concentration of inhibitor which reduces enzyme activity by 50%) of less than about 100 µM. Inhibitors with $IC_{50}$s of less than 100 µM are preferred, with $IC_{50}$s of less than 75 µM being more preferred and, in order of increasing preference, an $IC_{50}$ of 50 µM, 40 µM, 30 µM, 25 µM, 20 µM, 15 µM, 10 µM, 5 µM, 3 µM, 2 µM, 1 µM, 100 nM, 10 nM, 1.0 nM, or even less, being still more preferred. Assays for determining sEH activity are known in the art and described elsewhere herein. The $IC_{50}$ determination of the inhibitor can be made with respect to an sEH enzyme from the species subject to treatment (e.g., the subject receiving the inhibitor of sEH).

b. Cis-Epoxyeicosatrienoic Acids ("EETs"), Epoxyeicosatetraenoic Acids (EEQs) and Epoxydocosapentaenoic Acids (EDPs)

EETs, which are epoxides of arachidonic acid, are known to be effectors of blood pressure, regulators of inflammation, and modulators of vascular permeability. Hydrolysis of the epoxides by sEH diminishes this activity. Inhibition of sEH raises the level of EETs since the rate at which the EETs are hydrolyzed into dihydroxyeicosatrienoic acids ("DHETs") is reduced.

It has long been believed that EETs administered systemically would be hydrolyzed too quickly by endogenous sEH to be helpful. For example, in one prior report of EETs administration, EETs were administered by catheters inserted into mouse aortas. The EETs were infused continuously during the course of the experiment because of concerns over the short half-life of the EETs. See, Liao and Zeldin, International Publication WO 01/10438 (hereafter "Liao and Zeldin"). It also was not known whether endogenous sEH could be inhibited sufficiently in body tissues to permit administration of exogenous EET to result in increased levels of EETs over those normally present. Further, it was thought that EETs, as epoxides, would be too labile to survive the storage and handling necessary for therapeutic use.

Studies from the laboratory of the present inventors, however, showed that systemic administration of EETs in conjunction with inhibitors of sEH had better results than did administration of sEH inhibitors alone. EETs were not administered by themselves in these studies since it was anticipated they would be degraded too quickly to have a useful effect. Additional studies from the laboratory of the present inventors have since shown, however, that administration of EETs by themselves has had therapeutic effect. Without wishing to be bound by theory, it is surmised that the exogenous EET overwhelms endogenous sEH, and allows EETs levels to be increased for a sufficient period of time to have therapeutic effect. Thus, EETs can be administered without also administering an sEHI to provide a therapeutic effect. Moreover, EETs, if not exposed to acidic conditions or to sEH are stable and can withstand reasonable storage, handling and administration.

In short, sEHI, EETs, EEQs and EDPs, or co-administration of sEHIs and one or more of EETs, EEQs and EDPs, can be used in the present methods. In some embodiments, one or more EETs, EEQs and/or EDPs are administered to the patient without also administering an sEHI. In some embodiments, one or more EETs, EEQs and/or EDPs are administered shortly before or concurrently with administration of an sEH inhibitor to slow hydrolysis of the EETs, EEQs and/or EDPs. In some embodiments, one or more EETs, EEQs and/or EDPs are administered after administration of an sEH inhibitor, but before the level of the sEHI has diminished below a level effective to slow the hydrolysis of the EETs, EEQs and/or EDPs.

EETs useful in the methods include 14,15-EET, 8,9-EET and 11,12-EET, and 5,6 EETs. Preferably, the EETs are administered as the methyl ester, which is more stable. Persons of skill will recognize that the EETs are regioisomers, such as 8S,9R- and 14R,15S-EET. 8,9-EET, 11,12-EET, and 14R,15S-EET, are commercially available from, for example, Sigma-Aldrich (catalog nos. E5516, E5641, and E5766, respectively, Sigma-Aldrich Corp., St. Louis, MO). EEQs of use for direct administration include without limitation 17,18-epoxyeicosatetraenoic acid (17,18-EEQ). EDPs of use for direct administration include without limitation 19,20-epoxydocosapentaenoic (19,20-EDP).

If desired, EETs, EEQs and/or EDPs, analogs, or derivatives that retain activity can be used in place of or in combination with unmodified EETs, EEQs and/or EDPs. EETs, EEQs and/or EDPs analogs are defined herein as compounds with structural substitutions or alterations in an EETs, EEQs and/or EDPs, and include structural analogs in which one or more EETs, EEQs and/or EDPs olefins are removed or replaced with acetylene or cyclopropane groups, analogs in which the epoxide moiety is replaced with oxetane or furan rings and heteroatom analogs. In other analogs, the epoxide moiety is replaced with ether, alkoxides, urea, amide, carbamate, difluorocyclopropyl, or carbonyl group, while in others, the carboxylic acid moiety is stabilized by blocking beta oxidation or is replaced with a commonly used mimic, such as a nitrogen heterocycle, a sulfonamide, or another polar functionality. In some embodiments, olefins not critical for biological activity are removed and omega oxidation is reduced. In preferred forms, the analogs or derivatives are relatively stable as compared to an unmodified EETs, EEQs and/or EDPs because they are more resistant than an unmodified EETs, EEQs and/or EDPs to sEH and to chemical breakdown. "Relatively stable" means the rate of hydrolysis by sEH is at least 25% less than the hydrolysis of the unmodified EETs, EEQs and/or EDPs in a hydrolysis assay, and more preferably 50% or more lower than the rate of hydrolysis of an unmodified EETs, EEQs and/or EDPs. Liao and Zeldin show, for example, episulfide and sulfonamide EETs derivatives. In varying embodiments, amide and ester derivatives of EETs, EEQs and/or EDPs and that are relatively stable are administered. Whether or not a particular EETs, EEQs and/or EDPs analog or derivative has the biological activity of the unmodified EETs, EEQs and/or EDPs can be readily determined by using it in standard assays.

In some embodiments, the EETs, EEQs and/or EDPs are embedded or otherwise placed in a material that releases the EETs, EEQs and/or EDPs over time. Materials suitable for promoting the slow release of compositions such as EETs, EEQs and/or EDPs are known in the art. Optionally, one or more sEH inhibitors may also be placed in the slow release material.

Conveniently, the EETs, EEQs and/or EDPs can be administered orally. Since EETs are subject to degradation under acidic conditions, EETs intended for oral administration can be coated with a coating resistant to dissolving under acidic conditions, but which dissolve under the mildly basic conditions present in the intestines. Suitable coatings, commonly known as "enteric coatings" are widely used for products, such as aspirin, which cause gastric distress or which would undergo degradation upon exposure to gastric acid. By using coatings with an appropriate dissolution profile, the coated substance can be released in a chosen section of the intestinal tract. For example, a substance to be released in the colon is coated with a substance that dissolves at pH 6.5-7, while substances to be released in the duodenum can be coated with a coating that dissolves at pH values over 5.5. Such coatings are commercially available from, for example, Rohm Specialty Acrylics (Rohm America LLC, Piscataway, NJ) under the trade name "Eudragit®". The choice of the particular enteric coating is not critical to the practice.

c. Phosphodiesterase Inhibitors (PDEi)

Phosphodiesterase inhibitors (PDEi) are well known anti-inflammatory agents. Many different classes of isozyme selective PDEi lead to remarkable increases in the plasma levels of a broad range of epoxy-fatty acids (EpFAs). The magnitude of this increase is so dramatic that PDEi can elevate EpFAs as well as highly potent inhibitors of soluble epoxide hydrolase. Accordingly, levels of EpFAs (e.g., in blood, plasma, serum) can be increased by administration of a phosphodiesterase inhibitor (PDEi).

The PDEi may or may not be selective, specific or preferential for cAMP. Exemplary PDEs that degrade cAMP include without limitation PDE3, PDE4, PDE7, PDE8 and PDE10. Exemplary cAMP selective hydrolases include PDE4, 7 and 8. Exemplary PDEs that hydrolyze both cAMP and cGMP include PDE1, PDE2, PDE3, PDE10 and PDE11. Isoenzymes and isoforms of PDEs are well known in the art. See, e.g., Boswell-Smith et al., Brit. J. Pharmacol. 147: S252-257 (2006), and Reneerkens, et al., Psychopharmacology (2009) 202:419-443, the contents of which are incorporated herein by reference.

In some embodiments, the PDE inhibitor is a non-selective inhibitor of PDE. Exemplary non-selective PDE inhibitors that find use include without limitation caffeine, theophylline, isobutylmethylxanthine, aminophylline, pentoxifylline, vasoactive intestinal peptide (VIP), secretin, adrenocorticotropic hormone, pilocarpine, alpha-melanocyte stimulating hormone (MSH), beta-MSH, gamma-MSH, the ionophore A23187, prostaglandin E1.

In some embodiments, the PDE inhibitor used specifically or preferentially inhibits PDE4. Exemplary inhibitors that selectively inhibit PDE4 include without limitation rolipram, roflumilast, cilomilast, ariflo, HT0712, ibudilast and mesembrine.

In some embodiments, the PDE inhibitor used specifically or preferentially inhibits a cAMP PDE, e.g., PDE4, PDE7 or PDE8. In some embodiments, the PDE inhibitor used inhibits a cAMP PDE, e.g., PDE1, PDE2, PDE3, PDE4, PDE7, PDE8, PDE10 or PDE11. Exemplary agents that inhibit a cAMP phosphodiesterase include without limitation rolipram, roflumilast, cilomilast, ariflo, HT0712, ibudilast, mesembrine, cilostamide, enoxamone, milrinone, siguazodan and BRL-50481.

In some embodiments, the PDE inhibitor used specifically inhibits PDE5. Exemplary inhibitors that selectively inhibit PDE5 include without limitation sildenafil, zaprinast, tadalafil, udenafil, avanafil and vardenafil.

d. Assays for Epoxide Hydrolase Activity

Any of a number of standard assays for determining epoxide hydrolase activity can be used to determine inhibition of sEH. For example, suitable assays are described in Gill, et al., Anal Biochem 131:273-282 (1983); and Borhan, et al., Analytical Biochemistry 231:188-200 (1995)). Suitable in vitro assays are described in Zeldin et al., J Biol. Chem. 268:6402-6407 (1993). Suitable in vivo assays are described in Zeldin et al., Arch Biochem Biophys 330:87-96 (1996). Assays for epoxide hydrolase using both putative natural substrates and surrogate substrates have been reviewed (see, Hammock, et al. In: Methods in Enzymology, Volume III, Steroids and Isoprenoids, Part B, (Law, J. H. and H. C. Rilling, eds. 1985), Academic Press, Orlando, Florida, pp. 303-311 and Wixtrom et al., In: Biochemical Pharmacology and Toxicology, Vol. 1: Methodological Aspects of Drug Metabolizing Enzymes, (Zakim, D. and D. A. Vessey, eds. 1985), John Wiley & Sons, Inc., New York, pp. 1-93. Several spectral based assays exist based on the reactivity or tendency of the resulting diol product to hydrogen bond (see, e.g., Wixtrom, supra, and Hammock. Anal. Biochem. 174: 291-299 (1985) and Dietze, et al. Anal. Biochem. 216:176-187 (1994)).

The enzyme also can be detected based on the binding of specific ligands to the catalytic site which either immobilize the enzyme or label it with a probe such as dansyl, fluoracein, luciferase, green fluorescent protein or other reagent. The enzyme can be assayed by its hydration of EETs, its hydrolysis of an epoxide to give a colored product as described by Dietze et al., 1994, supra, or its hydrolysis of a radioactive surrogate substrate (Borhan et al., 1995, supra). The enzyme also can be detected based on the generation of fluorescent products following the hydrolysis of the epoxide. Numerous methods of epoxide hydrolase detection have been described (see, e.g., Wixtrom, supra).

The assays are normally carried out with a recombinant enzyme following affinity purification. They can be carried out in crude tissue homogenates, cell culture or even in vivo, as known in the art and described in the references cited above.

e. Other Means of Inhibiting sEH Activity

Other means of inhibiting sEH activity or gene expression can also be used in the methods. For example, a nucleic acid molecule complementary to at least a portion of the human sEH gene can be used to inhibit sEH gene expression. Means for inhibiting gene expression using short RNA molecules, for example, are known. Among these are short interfering RNA (siRNA), small temporal RNAs (stRNAs), and microRNAs (miRNAs). Short interfering RNAs silence genes through a mRNA degradation pathway, while stRNAs and miRNAs are approximately 21 or 22 nt RNAs that are processed from endogenously encoded hairpin-structured precursors, and function to silence genes via translational repression. See, e.g., McManus et al., RNA, 8(6):842-50 (2002); Morris et al., Science, 305(5688):1289-92 (2004); He and Hannon, Nat Rev Genet. 5(7):522-31 (2004).

"RNA interference," a form of post-transcriptional gene silencing ("PTGS"), describes effects that result from the introduction of double-stranded RNA into cells (reviewed in Fire, A. Trends Genet 15:358-363 (1999); Sharp, P. Genes Dev 13:139-141 (1999); Hunter, C. Curr Biol 9:R440-R442 (1999); Baulcombe. D. Curr Biol 9:R599-R601 (1999); Vaucheret et al. Plant J 16: 651-659 (1998)). RNA interference, commonly referred to as RNAi, offers a way of specifically inactivating a cloned gene, and is a powerful tool for investigating gene function.

The active agent in RNAi is a long double-stranded (antiparallel duplex) RNA, with one of the strands corresponding or complementary to the RNA which is to be inhibited. The inhibited RNA is the target RNA. The long double stranded RNA is chopped into smaller duplexes of approximately 20 to 25 nucleotide pairs, after which the mechanism by which the smaller RNAs inhibit expression of the target is largely unknown at this time. While RNAi was shown initially to work well in lower eukaryotes, for mammalian cells, it was thought that RNAi might be suitable only for studies on the oocyte and the preimplantation embryo.

In mammalian cells other than these, however, longer RNA duplexes provoked a response known as "sequence non-specific RNA interference," characterized by the non-specific inhibition of protein synthesis.

Further studies showed this effect to be induced by dsRNA of greater than about 30 base pairs, apparently due to an interferon response. It is thought that dsRNA of greater than about 30 base pairs binds and activates the protein PKR and 2',5'-oligonucleotide synthetase (2',5'-AS). Activated PKR stalls translation by phosphorylation of the translation initiation factors eIF2α, and activated 2',5'-AS causes mRNA degradation by 2',5'-oligonucleotide-activated ribonuclease L. These responses are intrinsically sequence-nonspecific to the inducing dsRNA; they also frequently result in apoptosis, or cell death. Thus, most somatic mammalian cells undergo apoptosis when exposed to the concentrations of dsRNA that induce RNAi in lower eukaryotic cells.

More recently, it was shown that RNAi would work in human cells if the RNA strands were provided as pre-sized duplexes of about 19 nucleotide pairs, and RNAi worked particularly well with small unpaired 3' extensions on the end of each strand (Elbashir et al. Nature 411: 494-498 (2001)). In this report, siRNA was applied to cultured cells by transfection in oligofectamine micelles. These RNA duplexes were too short to elicit sequence-nonspecific responses like apoptosis, yet they efficiently initiated RNAi. Many laboratories then tested the use of siRNA to knock out target genes in mammalian cells. The results demonstrated that siRNA works quite well in most instances.

For purposes of reducing the activity of sEH, siRNAs to the gene encoding sEH can be specifically designed using computer programs. The cloning, sequence, and accession numbers of the human sEH sequence are set forth in Beetham et al., Arch. Biochem. Biophys. 305(1):197-201 (1993). An exemplary amino acid sequence of human sEH (GenBank Accession No. L05779; SEQ ID NO:1) and an exemplary nucleotide sequence encoding that amino acid sequence (GenBank Accession No. AAA02756; SEQ ID NO:2) are set forth in U.S. Pat. No. 5,445,956. The nucleic acid sequence of human sEH is also published as GenBank Accession No. NM_001979.4; the amino acid sequence of human sEH is also published as GenBank Accession No. NP_001970.2.

A program, siDESIGN from Dharmacon, Inc. (Lafayette, CO), permits predicting siRNAs for any nucleic acid sequence, and is available on the World Wide Web at dharmacon.com. Programs for designing siRNAs are also available from others, including Genscript (available on the Web at genscript.com/ssl-bin/app/rnai) and, to academic and non-profit researchers, from the Whitehead Institute for Biomedical Research found on the worldwide web at "jura.wi.mit.edu/pubint/http://iona.wi.mit.edu/siRNAext/."

For example, using the program available from the Whitehead Institute, the following sEH target sequences and siRNA sequences can be generated:

```
1) Target:
                                        (SEQ ID NO: 3)
   CAGTGTTCATTGGCCATGACTGG Sense-siRNA:
                                        (SEQ ID NO: 4)
   5'-GUGUUCAUUGGCCAUGACUTT-3'

Antisense-siRNA:
                                        (SEQ ID NO: 5)
   5'-AGUCAUGGCCAAUGAACACTT-3'

2) Target:
                                        (SEQ ID NO: 6)
   GAAAGGCTATGGAGAGTCATCTG Sense-siRNA:
                                        (SEQ ID NO: 7)
   5'-AAGGCUAUGGAGAGUCAUCTT-3'

Antisense-siRNA:
                                        (SEQ ID NO: 8)
   5'-GAUGACUCUCCAUAGCCUUTT-3'

3) Target
                                        (SEQ ID NO: 9)
   AAAGGCTATGGAGAGTCATCTGC Sense-siRNA:
                                        (SEQ ID NO: 10)
   5'-AGGCUAUGGAGAGUCAUCUTT-3'

Antisense-siRNA:
                                        (SEQ ID NO: 11)
   5'-AGAUGACUCUCCAUAGCCUTT-3'

4) Target:
                                        (SEQ ID NO: 12)
   CAAGCAGTGTTCATTGGCCATGA Sense-siRNA:
                                        (SEQ ID NO: 13)
   5'-AGCAGUGUUCAUUGGCCAUTT-3'

Antisense-siRNA:
                                        (SEQ ID NO: 14)
   5'-AUGGCCAAUGAACACUGCUTT-3'

5) Target:
                                        (SEQ ID NO: 15)
   CAGCACATGGAGGACTGGATTCC Sense-siRNA:
                                        (SEQ ID NO: 16)
   5'-GCACAUGGAGGACUGGAUUTT-3'

Antisense-siRNA:
                                        (SEQ ID NO: 17)
   5'-AAUCCAGUCCUCCAUGUGCTT-3'
```

Alternatively, siRNA can be generated using kits which generate siRNA from the gene. For example, the "Dicer siRNA Generation" kit (catalog number T510001, Gene Therapy Systems, Inc., San Diego, CA) uses the recombinant human enzyme "dicer" in vitro to cleave long double stranded RNA into 22 bp siRNAs. By having a mixture of siRNAs, the kit permits a high degree of success in generating siRNAs that will reduce expression of the target gene.

Similarly, the Silencer™ siRNA Cocktail Kit (RNase III) (catalog no. 1625, Ambion, Inc., Austin, TX) generates a mixture of siRNAs from dsRNA using RNase III instead of dicer. Like dicer, RNase III cleaves dsRNA into 12-30 bp dsRNA fragments with 2 to 3 nucleotide 3' overhangs, and 5'-phosphate and 3'-hydroxyl termini. According to the manufacturer, dsRNA is produced using T7 RNA polymerase, and reaction and purification components included in the kit. The dsRNA is then digested by RNase III to create a population of siRNAs. The kit includes reagents to synthesize long dsRNAs by in vitro transcription and to digest those dsRNAs into siRNA-like molecules using RNase III. The manufacturer indicates that the user need only supply a DNA template with opposing T7 phage polymerase promoters or two separate templates with promoters on opposite ends of the region to be transcribed.

The siRNAs can also be expressed from vectors. Typically, such vectors are administered in conjunction with a second vector encoding the corresponding complementary strand. Once expressed, the two strands anneal to each other and form the functional double stranded siRNA. One exemplar vector suitable for use in the invention is pSuper, available from OligoEngine, Inc. (Seattle, WA). In some embodiments, the vector contains two promoters, one positioned downstream of the first and in antiparallel orientation. The first promoter is transcribed in one direction, and the second in the direction antiparallel to the first, resulting in expression of the complementary strands. In yet another set of embodiments, the promoter is followed by a first segment encoding the first strand, and a second segment encoding the second strand. The second strand is complementary to the palindrome of the first strand. Between the first and the second strands is a section of RNA serving as a linker (sometimes called a "spacer") to permit the second strand to bend around and anneal to the first strand, in a configuration known as a "hairpin."

The formation of hairpin RNAs, including use of linker sections, is well known in the art. Typically, an siRNA expression cassette is employed, using a Polymerase III promoter such as human U6, mouse U6, or human H1. The coding sequence is typically a 19-nucleotide sense siRNA sequence linked to its reverse complementary antisense siRNA sequence by a short spacer. Nine-nucleotide spacers are typical, although other spacers can be designed. For example, the Ambion website indicates that its scientists have had success with the spacer TTCAAGAGA (SEQ ID NO:18). Further, 5-6 T's are often added to the 3' end of the oligonucleotide to serve as a termination site for Polymerase III. See also, Yu et al., Mol Ther 7(2):228-36 (2003); Matsukura et al., Nucleic Acids Res 31(15):e77 (2003).

As an example, the siRNA targets identified above can be targeted by hairpin siRNA as follows. To attack the same targets by short hairpin RNAs, produced by a vector (permanent RNAi effect), sense and antisense strand can be put in a row with a loop forming sequence in between and suitable sequences for an adequate expression vector to both ends of the sequence. The following are non-limiting examples of hairpin sequences that can be cloned into the pSuper vector:

1) Target:
(SEQ ID NO: 19)
CAGTGTTCATTGGCCATGACTGG

Sense strand:
(SEQ ID NO: 20)
5'-GATCCCCGTGTTCATTGGCCATGACTTTCAAGAGAAGTCATGGCCA
ATGAACACTTTTT-3'

Antisense strand:
(SEQ ID NO: 21)
5'-AGCTAAAAAGTGTTCATTGGCCATGACTTCTCTTGAAAGTCATGGC
CAATGAACACGGG-3'

2) Target:
(SEQ ID NO: 22)
GAAAGGCTATGGAGAGTCATCTG

Sense strand:
(SEQ ID NO: 23)
5'-GATCCCCAAGGCTATGGAGAGTCATCTTCAAGAGAGATGACTCTCC
ATAGCCTTTTTT-3'

Antisense strand:
(SEQ ID NO: 24)
5'-AGCTAAAAAAGGCTATGGAGAGTCATCTCTCTTGAAGATGACTCT
CCATAGCCTTGGG-3'

3) Target:
(SEQ ID NO: 25)
AAAGGCTATGGAGAGTCATCTGC

Sense strand:
(SEQ ID NO: 26)
5'-GATCCCCAGGCTATGGAGAGTCATCTTTCAAGAGAAGATGACTCTC
CATAGCCTTTTTT-3'

Antisense strand:
(SEQ ID NO: 27)
5'-AGCTAAAAAAGGCTATGGAGAGTCATCATCTCTTGAAAGATGACTC
TCCATAGCCTGGG-3'

4) Target:
(SEQ ID NO: 28)
CAAGCAGTGTTCATTGGCCATGA

Sense strand:
(SEQ ID NO: 29)
5'-GATCCCCAGCAGTGTTCATTGGCCATTTCAAGAGAATGGCCAATGA
ACACTGCTTTTTT-3'

Antisense strand:
(SEQ ID NO: 30)
5'-AGCTAAAAAAGCAGTGTTCATTGGCCATTCTCTTGAAATGGCCAAT
GAACACTGCTGGG-3'

5) Target:
(SEQ ID NO: 31)
CAGCACATGGAGGACTGGATTCC

Sense strand
(SEQ ID NO: 32)
5'-GATCCCCGCACATGGAGGACTGGATTTTCAAGAGAAATCCAGTCCT
CCATGTGCTTTTT-3'

Antisense strand:
(SEQ ID NO: 33)
5'-AGCTAAAAAGCACATGGAGGACTGGATTTCTCTTGAAAATCCAGTC
CTCCATGTGCGGG-3'

In addition to siRNAs, other means are known in the art for inhibiting the expression of antisense molecules, ribozymes, and the like are well known to those of skill in the art. The nucleic acid molecule can be a DNA probe, a riboprobe, a peptide nucleic acid probe, a phosphorothioate probe, or a 2'-O methyl probe.

Generally, to assure specific hybridization, the antisense sequence is substantially complementary to the target sequence. In certain embodiments, the antisense sequence is exactly complementary to the target sequence. The antisense polynucleotides may also include, however, nucleotide substitutions, additions, deletions, transitions, transpositions, or modifications, or other nucleic acid sequences or non-nucleic acid moieties so long as specific binding to the relevant target sequence corresponding to the sEH gene is retained as a functional property of the polynucleotide. In one embodiment, the antisense molecules form a triple helix-containing, or "triplex" nucleic acid. Triple helix formation results in inhibition of gene expression by, for example, preventing transcription of the target gene (see, e.g., Cheng et al., 1988, J. Biol. Chem. 263:15110; Ferrin and Camerini-Otero, 1991, Science 354:1494; Ramdas et al., 1989, J. Biol. Chem. 264:17395; Strobel et al., 1991, Science 254:1639; and Rigas et al., 1986, Proc. Natl. Acad. Sci. U.S.A. 83:9591)

Antisense molecules can be designed by methods known in the art. For example, Integrated DNA Technologies (Coralville, IA) makes available a program found on the worldwide web "biotools.idtdna.com/antisense/AntiSense.aspx", which will provide appropriate antisense sequences for nucleic acid sequences up to 10,000 nucleotides in length. Using this program with the sEH gene provides the following exemplar sequences:

1)
UGUCCAGUGCCCACAGUCCU (SEQ ID NO: 34)

2)
UUCCCACCUGACACGACUCU (SEQ ID NO: 35)

3)
GUUCAGCCUCAGCCACUCCU (SEQ ID NO: 36)

4)
AGUCCUCCCGCUUCACAGA (SEQ ID NO: 37)

5)
GCCCACUUCCAGUUCCUUUCC (SEQ ID NO: 38)

In another embodiment, ribozymes can be designed to cleave the mRNA at a desired position. (See, e.g., Cech, 1995, Biotechnology 13:323; and Edgington, 1992, Biotechnology 10:256 and Hu et al., PCT Publication WO 94/03596).

The antisense nucleic acids (DNA, RNA, modified, analogues, and the like) can be made using any suitable method for producing a nucleic acid, such as the chemical synthesis and recombinant methods disclosed herein and known to one of skill in the art. In one embodiment, for example, antisense RNA molecules may be prepared by de novo chemical synthesis or by cloning. For example, an antisense RNA can be made by inserting (ligating) a sEH gene sequence in reverse orientation operably linked to a promoter in a vector (e.g., plasmid). Provided that the promoter and, preferably termination and polyadenylation signals, are properly positioned, the strand of the inserted sequence corresponding to the noncoding strand are transcribed and act as an antisense oligonucleotide.

It are appreciated that the oligonucleotides can be made using nonstandard bases (e.g., other than adenine, cytidine, guanine, thymine, and uridine) or nonstandard backbone structures to provides desirable properties (e.g., increased nuclease-resistance, tighter-binding, stability or a desired Tm). Techniques for rendering oligonucleotides nuclease-resistant include those described in PCT Publication WO 94/12633. A wide variety of useful modified oligonucleotides may be produced, including oligonucleotides having a peptide-nucleic acid (PNA) backbone (Nielsen et al., 1991, Science 254:1497) or incorporating 2'-O-methyl ribonucleotides, phosphorothioate nucleotides, methyl phosphonate nucleotides, phosphotriester nucleotides, phosphorothioate nucleotides, phosphoramidates.

Proteins have been described that have the ability to translocate desired nucleic acids across a cell membrane. Typically, such proteins have amphiphilic or hydrophobic subsequences that have the ability to act as membrane-translocating carriers. For example, homeodomain proteins have the ability to translocate across cell membranes. The shortest internalizable peptide of a homeodomain protein, Antennapedia, was found to be the third helix of the protein, from amino acid position 43 to 58 (see, e.g., Prochiantz, Current Opinion in Neurobiology 6:629-634 (1996). Another subsequence, the h (hydrophobic) domain of signal peptides, was found to have similar cell membrane translocation characteristics (see, e.g., Lin et al., J. Biol. Chem. 270:14255-14258 (1995)). Such subsequences can be used to translocate oligonucleotides across a cell membrane. Oligonucleotides can be conveniently derivatized with such sequences. For example, a linker can be used to link the oligonucleotides and the translocation sequence. Any suitable linker can be used, e.g., a peptide linker or any other suitable chemical linker.

More recently, it has been discovered that siRNAs can be introduced into mammals without eliciting an immune response by encapsulating them in nanoparticles of cyclodextrin. Information on this method can be found on the worldwide web at "nature.com/news/2005/050418/full/050418-6.html."

In another method, the nucleic acid is introduced directly into superficial layers of the skin or into muscle cells by a jet of compressed gas or the like. Methods for administering naked polynucleotides are well known and are taught, for example, in U.S. Pat. No. 5,830,877 and International Publication Nos. WO 99/52483 and WO 94/21797. Devices for accelerating particles into body tissues using compressed gases are described in, for example, U.S. Pat. Nos. 6,592,545, 6,475,181, and 6,328,714. The nucleic acid may be lyophilized and may be complexed, for example, with polysaccharides to form a particle of appropriate size and mass for acceleration into tissue. Conveniently, the nucleic acid can be placed on a gold bead or other particle which provides suitable mass or other characteristics. Use of gold beads to carry nucleic acids into body tissues is taught in, for example, U.S. Pat. Nos. 4,945,050 and 6,194,389.

The nucleic acid can also be introduced into the body in a virus modified to serve as a vehicle without causing pathogenicity. The virus can be, for example, adenovirus, fowlpox virus or vaccinia virus.

miRNAs and siRNAs differ in several ways: miRNA derive from points in the genome different from previously recognized genes, while siRNAs derive from mRNA, viruses or transposons, miRNA derives from hairpin structures, while siRNA derives from longer duplexed RNA, miRNA is conserved among related organisms, while siRNA usually is not, and miRNA silences loci other than that from which it derives, while siRNA silences the loci from which it arises. Interestingly, miRNAs tend not to exhibit perfect complementarity to the mRNA whose expression they inhibit. See, McManus et al., supra. See also, Cheng et al., Nucleic Acids Res. 33(4):1290-7 (2005); Robins and Padgett, Proc Natl Acad Sci USA. 102(11): 4006-9 (2005); Brennecke et al., PLoS Biol. 3(3):e85

(2005). Methods of designing miRNAs are known. See, e.g., Zeng et al., Methods Enzymol. 392:371-80 (2005); Krol et al., J Biol Chem. 279(40):42230-9 (2004); Ying and Lin, Biochem Biophys Res Commun. 326(3):515-20 (2005).

In some embodiments, the endogenous polynucleotide encoding sEH in the subject can be rendered non-functional or non-expressing, e.g., by employing gene therapy methodologies. This can be accomplished using any method known in the art, including the working embodiment described herein. In varying embodiments, the endogenous gene encoding sEH in the subject is rendered non-functional or non-expressing in certain desired tissues, e.g., in renal tissue or more specifically in podocyte cells, as demonstrated herein. In varying embodiments, the endogenous gene encoding sEH in the subject is rendered non-functional or non-expressing by employing homologous recombination, mutating, replacing or eliminating the functional or expressing gene encoding sEH. Illustrative methods are known in the art and described, e.g., in Flynn, et al., *Exp Hematol.* (2015) Jun. 19. pii: S0301-472X(15)00207-6 (using CRISPR); Truong, et al, *Nucleic Acids Res.* (2015) Jun. 16. pii: gkv601 (using split-Cas9); Yang, *Mil Med Res.* (2015) May 9; 2:11 (using CRISPR-Cas9); and Imai, et al., *Intern Med.* (2004) February; 43(2):85-96.

f. Epoxy-Fatty Acids (EpFAs)

In some embodiments, an epoxy-fatty acid is administered as an agent that increases epoxy-fatty acids. Illustrative epoxy-fatty acids include epoxides of linoleic acid, eicosapentaenoic acid ("EPA") and docosahexaenoic acid ("DHA").

The fatty acids eicosapentaenoic acid ("EPA") and docosahexaenoic acid ("DHA") have recently become recognized as having beneficial effects, and fish oil tablets, which are a good source of these fatty acids, are widely sold as supplements. In 2003, it was reported that these fatty acids reduced pain and inflammation. Sethi, S. et al., Blood 100: 1340-1346 (2002). The paper did not identify the mechanism of action, nor the agents responsible for this relief.

Cytochrome P450 ("CYP450") metabolism produces cis-epoxydocosapentaenoic acids ("EDPs" or "EpDPEs") and cis-epoxyeicosatetraenoic acids ("EEQs" or "EpETEs") from docosahexaenoic acid ("DHA") and eicosapentaenoic acid ("EPA"), respectively. These epoxides are known endothelium-derived hyperpolarizing factors ("EDHFs"). These EDHFs, and others yet unidentified, are mediators released from vascular endothelial cells in response to acetylcholine and bradykinin, and are distinct from the NOS— (nitric oxide) and COX-derived (prostacyclin) vasodilators. Overall cytochrome P450 (CYP450) metabolism of polyunsaturated fatty acids produces epoxides, such as EETs, which are prime candidates for the active mediator(s). 14(15)-EpETE, for example, is derived via epoxidation of the 14,15-double bond of EPA and is the ω-3 homolog of 14(15)-EpETrE ("14(15)EET") derived via epoxidation of the 14,15-double bond of arachidonic acid.

As mentioned, it is beneficial to elevate the levels of EETs, which are epoxides of the fatty acid arachidonic acid. Our studies of the effects of EETs has led us to realization that the anti-inflammatory effect of EPA and DHA are likely due to increasing the levels of the epoxides of these two fatty acids. Thus, increasing the levels of epoxides of EPA, of DHA, or of both, will act to reduce, mitigate, ameliorate, improve symptoms associated with a neuropsychiatric illness characterized by depressive symptoms, in mammals in need thereof. This beneficial effect of the epoxides of these fatty acids has not been previously recognized. Moreover, these epoxides have not previously been administered as agents, in part because, as noted above, epoxides have generally been considered too labile to be administered.

Like EETs, the epoxides of EPA and DHA are substrates for sEH. The epoxides of EPA and DHA are produced in the body at low levels by the action of cytochrome P450s. Endogenous levels of these epoxides can be maintained or increased by the administration of sEHI. However, the endogenous production of these epoxides is low and usually occurs in relatively special circumstances, such as the resolution of inflammation. Our expectation is that administering these epoxides from exogenous sources will aid in the resolution of symptoms of neuropsychiatric illnesses characterized by depressive symptoms. It is further beneficial with pain or inflammation to inhibit sEH with sEHI to reduce hydrolysis of these epoxides, thereby maintaining them at relatively high levels.

EPA has five unsaturated bonds, and thus five positions at which epoxides can be formed, while DHA has six. The epoxides of EPA are typically abbreviated and referred to generically as "EEQs" or "EpETEs", while the epoxides of DHA are typically abbreviated and referred to generically as "EDPs" or "EpDPEs". The specific regioisomers of the epoxides of each fatty acid are set forth in the following Table 3.

TABLE 3

Regioisomers of Eicosapentaenoic acid ("EPA") epoxides:
1. Formal name: (±)5(6)- epoxy- 8Z, 11Z, 14Z, 17Z-eicosatetraenoic acid,
    Synonym 5(6)- epoxy Eicosatetraenoic acid
    Abbreviation 5(6)- EpETE
2. Formal name: (±)8(9)- epoxy- 5Z, 11Z, 14Z, 17Z-eicosatetraenoic acid,
    Synonym 8(9)- epoxy Eicosatetraenoic acid
    Abbreviation 8(9)- EpETE
3. Formal name: (±)11(12)- epoxy- 5Z, 8Z, 14Z, 17Z -eicosatetraenoic acid,
    Synonym 11(12)- epoxy Eicosatetraenoic acid
    Abbreviation 11(12)- EpETE
4. Formal name: (±)14(15)- epoxy-5Z, 8Z, 11Z, 17Z-eicosatetraenoic acid,
    Synonym 14(15)- epoxy Eicosatetraenoic acid
    Abbreviation 14(15)- EpETE
5. Formal name: (±)17(18)- epoxy- 5Z, 8Z, 11Z, 14Z-eicosatetraenoic acid,
    Synonym 17(18)- epoxy Eicosatetraenoic acid
    Abbreviation 17(18)- EpETE
Regioisomers of Docosahexaenoic acid ("DHA") epoxides:
1. Formal name: (±) 4(5)- epoxy- 7Z, 10Z, 13Z, 16Z, 19Z -docosapentaenoic acid,
    Synonym 4(5)- epoxy Docosapentaenoic acid
    Abbreviation 4(5)- EpDPE

TABLE 3-continued

2. Formal name: (±) 7(8)- epoxy- 4Z, 10Z, 13Z, 16Z, 19Z -docosapentaenoic acid,
   Synonym 7(8)- epoxy Docosapentaenoic acid
   Abbreviation 7(8)- EpDPE
3. Formal name: (±)10(11)- epoxy-4Z, 7Z, 13Z, 16Z, 19Z -docosapentaenoic acid,
   Synonym 10(11)- epoxy Docosapentaenoic acid
   Abbreviation 10(11)- EpDPE
4. Formal name: (±)13(14)- epoxy-4Z, 7Z, 10Z, 16Z, 19Z -docosapentaenoic acid,
   Synonym 13(14)- epoxy Docosapentaenoic acid
   Abbreviation 13(14)- EpDPE
5. Formal name: (±) 16(17)- epoxy- 4Z, 7Z, 10Z, 13Z, 19Z -docosapentaenoic acid,
   Synonym 16(17)- epoxy Docosapentaenoic acid
   Abbreviation 16(17)- EpDPE
6. Formal name: (±) 19(20)- epoxy- 4Z, 7Z, 10Z, 13Z, 16Z -docosapentaenoic acid,
   Synonym 19(20)- epoxy Docosapentaenoic acid
   Abbreviation 19(20)- EpDPE Any of these epoxides, or combinations of any of these, can be administered in the compositions and methods.

5. Secondary Agents that Synergize with Inhibitors of Soluble Epoxide Hydrolase In varying embodiments, the agent that increases epoxy-fatty acids or the inhibitor of soluble epoxide hydrolase is co-administered with an enhancing or synergizing agent. Illustrative agents that enhance the activity or efficaciousness of directly inhibiting soluble epoxide hydrolase include without limitation inhibitors of cyclooxygenase-2 (COX-2), inhibitors of phosphodiesterase, agonists of peroxisome proliferator activated receptor alpha (PPARα) and agonists of peroxisome proliferator activated receptor gamma (PPARγ).

Illustrative selective or preferential inhibitors of COX-2 that may be co-administered with an inhibitor of soluble epoxide hydrolase include without limitation celecoxib, valdecoxib, lumiracoxib, etoricoxib, and rofecoxib. Illustrative inhibitors of phosphodiesterase 4 that may be co-administered with an inhibitor of soluble epoxide hydrolase include without limitation rolipram, roflumilast, cilomilast, ariflo, HT0712, ibudilast and mesembrine. Illustrative inhibitors of phosphodiesterase 5 that may be co-administered with an inhibitor of soluble epoxide hydrolase include without limitation sildenafil, zaprinast, tadalafil, udenafil, avanafil and vardenafil. Illustrative agonists of PPARα that may be co-administered with an inhibitor of soluble epoxide hydrolase include without limitation clofibrate, gemfibrozil, ciprofibrate, bezafibrate, and fenofibrate. Illustrative agonists of PPARγ that may be co-administered with an inhibitor of soluble epoxide hydrolase include without limitation thiazolidinediones (TZDs).

6. Agents for Treating Neurodevelopmental Disorders

There are a number of pharmacological agents that are used to treat or ameliorate neurodevelopmental disorders. For example, patients with autism spectrum disorder are sometimes prescribed antidepressants, anti-psychotics, stimulants, and/or anticonvulsants. Additional agents sometime used to treat neurodevelopmental disorders are anxiolytics. When co-administered with an agent that increases epoxy-fatty acids, e.g., an inhibitor of soluble epoxide hydrolase, the effectiveness of the additional therapeutic agent in mitigating, ameliorating, reducing and/or inhibiting one or more symptoms associated with a neurodevelopmental disorder can be enhanced, in terms of increased potency, reduced dosage requirements, earlier onset to effectiveness and sustained efficacy.

a. Antidepressants

Illustrative antidepressant agents that can be co-administered with an agent that increases epoxy-fatty acids include without limitation selective serotonin reuptake inhibitors (SSRIs), serotonin-norepinephrine reuptake inhibitors (SNRIs), tricyclic or tetracyclic antidepressants (TCAs), a monoamine oxidase inhibitors (MAOIs) and atypical antidepressants.

Illustrative selective serotonin reuptake inhibitors (SSRIs) include without limitation citalopram, escitalopram, fluoxetine, fluvoxamine, fluvoxamine CR, paroxetine, paroxetine CR, and sertraline.

Illustrative serotonin-norepinephrine reuptake inhibitors (SNRIs) include without limitation desvenlafaxine, duloxetine, venlafaxine, venlafaxine XR, milnacipran, and levomilnacipran.

Illustrative tricyclic or tetracyclic antidepressants (TCAs) include without limitation amitriptyline, amoxapine, desipramine, doxepin, imipramine, nortriptyline, protriptyline, trimipramine and maprotiline.

Illustrative monoamine oxidase inhibitors (MAOIs) include without limitation selegiline, moclobemide, tranylcypromine, isocarboxazid and phenylzine.

b. Antipsychotics

Illustrative antipsychotics that can be co-administered with an agent that increases epoxy-fatty acids include without limitation a butyrophenone, a diphenylbutylpiperidine, a phenothiazine, a thioxanthene, or is an atypical antipsychotic agent.

In varying embodiments, the antipsychotic is selected from the group consisting of benperidol, bromperidol, droperidol, haloperidol, moperone, pipamperone, timiperone, fluspirilene, penfluridol, pimozide, phenothiazines, acepromazine, chlorpromazine, cyamemazine, dixyrazine, fluphenazine, levomepromazine, mesoridazine, perazine, pericyazine, perphenazine, pipotiazine, prochlorperazine, promazine, promethazine, prothipendyl, thioproperazine, thioridazine, trifluoperazine, triflupromazine, thioxanthenes, chlorprothixene, clopenthixol, flupentixol, thiothixene, zuclopenthixol, clotiapine, loxapine, prothipendyl, carpipramine, clocapramine, molindone, mosapramine, sulpiride, sultopride, veralipride, amisulpride, amoxapine, aripiprazole, asenapine, cariprazine, clozapine, blonanserin, iloperidone, lurasidone, melperone, nemonapride, olanzapine, paliperidone, perospirone, quetiapine, remoxipride, risperidone, aripiprazole, sertindole, sultopride, trimipramine, ziprasidone, zotepine, brexpiprazole, ITI-007, pimavanserin and RP5063.

c. Stimulants

Illustrative stimulants that can be co-administered with an agent that increases epoxy-fatty acids include without limitation amphetamines such as amphetamine, dextroamphetamine, methamphetamine, lisdexamfetamine, or a combination thereof.

d. Anticonvulsants

Illustrative anticonvulsants that can be co-administered with an agent that increases epoxy-fatty acids include without limitation Valproic acid, Phenytoin, Clonazepam, and Carbamazepine.

e. Anxiolytics

Illustrative anxiolytics (e.g., anti-anxiety agent, anti-panic agent) that can be co-administered with an agent that increases epoxy-fatty acids include without limitation a barbiturate, a benzodiazepine and a beta-blocker.

In varying embodiments, the anxiolytic drug is selected from the group consisting of alprazolam, bromazepam, chlordiazepoxide, clonazepam, clorazepate, diazepam, flurazepam, lorazepam, oxazepam, temazepam, triazolam, tofisopam, clonidine, guanfacine, mebicar, fabomotizole, selank, bromantane, emoxypine, buspirone, tandospirone, hydroxyzine, pregabalin, menthyl isovalerate, cannabidiol (cbd), tetrahydrocannabinol, *Garcinia indica* (kokum), *Scutellaria lateriflora, Coriandrum sativum* (coriander), *Salvia elegans* (pineapple sage), picamilon, chlorpheniramine, diphenhydramine, melatonin and myo-inositol.

7. Formulation and Administration

In some embodiments, the agent that increases epoxy-fatty acids (e.g., an inhibitor of sEH, an epoxy-fatty acid, and mixtures thereof) is administered as a monotherapy.

Pharmaceutical compositions or medicaments comprising an agent that increases epoxy-fatty acids (e.g., an inhibitor of sEH, an epoxy-fatty acid, and mixtures thereof) can be administered to a subject at a therapeutically effective dose. In some embodiments, the pharmaceutical composition or medicament comprising an agent that increases epoxy-fatty acids (e.g., an inhibitor of sEH, an epoxy-fatty acid, and mixtures thereof) is administered to a subject in an amount sufficient to elicit an effective therapeutic response in the subject. In some embodiments, the pharmaceutical composition or medicament comprising an agent that increases epoxy-fatty acids (e.g., an inhibitor of sEH, an epoxy-fatty acid, and mixtures thereof) can be administered to a subject at a therapeutically effective dose.

The agent that increases epoxy-fatty acids can be prepared and administered in a wide variety of oral, parenteral and topical dosage forms. In some embodiments, the agent that increases epoxy-fatty acids is administered orally or by injection, that is, intravenously, intramuscularly, intracutaneously, subcutaneously, intraduodenally, or intraperitoneally. In some embodiments, the agent that increases epoxy-fatty acids is administered by inhalation, for example, intranasally. In some embodiments, the agent that increases epoxy-fatty acids is administered transdermally.

In some embodiments of the compositions, the agent that increases epoxy-fatty acids (e.g., an inhibitor of sEH, an epoxy-fatty acid, and mixtures thereof) is co-administered with the second agent (e.g., antidepressant, anti-psychotic, etc.). In some embodiments, the agent that increases epoxy-fatty acids comprises an epoxide of EPA, an epoxide of DHA, or epoxides of both, and an sEHI.

The agent that increases epoxy-fatty acids and the second agent (e.g., antidepressant, anti-psychotic, etc.) independently can be prepared and administered in a wide variety of oral, parenteral and topical dosage forms. The agent that increases epoxy-fatty acids and the second agent (e.g., antidepressant, anti-psychotic, etc.) can be administered via the same or different routes of administration. In varying embodiments, the agent that increases epoxy-fatty acids and the second agent (e.g., antidepressant, anti-psychotic, etc.) independently can be administered orally, by injection, that is, intravenously, intramuscularly, intracutaneously, subcutaneously, intraduodenally, or intraperitoneally. In some embodiments, the agent that increases epoxy-fatty acids and the second agent (e.g., antidepressant, anti-psychotic, etc.) is administered by inhalation, for example, intranasally. In some embodiments, the agent that increases epoxy-fatty acids and the second agent (e.g., antidepressant, anti-psychotic, etc.) is administered transdermally.

In varying embodiments, the agent that increases epoxy-fatty acids (e.g., an sEHI or a pharmaceutically acceptable salt of the inhibitor and, optionally, one or more EETs or epoxides of EPA or of DHA, or of both), and/or the second agent (e.g., antidepressant, mood stabilizer, anti-psychotic, anxiolytic) are specifically, predominantly or preferentially targeted to the brain. Methods for preferentially targeting therapeutic agents to brain tissues are known in the art and find use. Illustrative strategies useful for targeted and/or enhanced delivery of organic compounds and oligonucleotides to the brain are discussed in, e.g., Hanson, et al., *BMC Neurosci.* (2008) 9 Suppl 3:S5; Kim, et al., *Mol Ther.* (2012) 20(4):829-39; Gong, et al., *Biomaterials.* (2012) 33(12): 3456-63; Gomez, et al., *Front Biosci* (Schol Ed). (2012) 4:74-89; Patel, et al., *CNS Drugs.* (2009) 23(1):35-58; Fonseca-Santos, et al., *Int J Nanomedicine.* (2015) 10:4981-5003; Sela, et al., *J Nanobiotechnology.* (2015) Oct. 21; 13:71; and Rajadhyaksha, et al., *Curr Drug Discov Technol.* (2011) 8(2):87-101.

In varying embodiments, in order to enhance delivery to the brain, the one or more agents or compounds can be co-administered with, conjugated to or encapsulated within an agent that facilitate transport across the blood-brain-barrier. Strategies and agents useful for facilitating delivery across the blood-brain-barrier are known in the art and can be employed in the present methods. Current strategies for delivering active agents across the blood-brain barrier and that find use in the present methods include without limitation nanocarriers and nanoparticles (Tam, et al., *Int J Pharm.* (2016) 515(1-2):331-342; Zhao, et al., *Nanoscale Res Lett.* 2016 December; 11(1):451; Song, et al., *Mol Pharm.* (2016) Oct. 4; PMID: 27700119; Lalatsa, et al., *Int Rev Neurobiol.* 2016; 130:115-53; Kundo, et al., *ACS Chem Neurosci.* (2016) Oct. 3; PMID: 27642670); functionalized carbon nanotubes (Costa, et al., *J Control Release.* (2016) 241:200-219); nanowires (Sharma, et al., *CNS Neurol Disord Drug Targets.* 2016 Aug. 19; PMID: 27538949); viral vectors (Fu, et al., *Curr Opin Virol.* (2016) 21:87-92); liposomes and exosomes (Tremmel, et al., *Int J Pharm.* (2016) 512(1):87-95; Sanchez-Purrà, et al., *Int J Pharm.* (2016) 511(2):946-56; Bender, et al. *J Vis Exp.* (2016) Jul. 23; (113). doi: 10.3791/54106; Ha, et al., *Acta Pharm Sin B.* (2016) 6(4): 287-96); dendrimers (Jiang, et al, *Colloids Surf B Biointerfaces.* (2016) 147:242-9) and ultrasound (Park, et al., *J Control Release.* (2016) Oct. 11. pii: S0168-3659(16)30955-5; Airan, et al., *Mol Imaging Biol.* (2016) Aug. 1; PMID: 27481359). In varying embodiments, the one or more compounds can be conjugated to or administered in conjunction with a peptide that promotes transcytosis and traversal of the blood-brain barrier. Illustrative peptides include without limitation Angiopep-2 (Li, et al., *Oncotarget.* 2016 Oct. 17. doi: 10.18632; PMID: 27765902); Transferrin (Nanoscale.

(2016) 8(37):16662-16669); penetratin (Spencer, et al., *Ann Clin Transl Neurol*. (2016) 3(8):588-606); and M36 fungalysin metalloprotease (WO 2013/036827).

Furthermore, the agent that increases epoxy-fatty acids and the optional second agent (e.g., antidepressant, antipsychotic, etc.) can be co-formulated in a single composition or can be formulated for separate co-administration. Accordingly, in some embodiments, the methods contemplate administration of compositions comprising a pharmaceutically acceptable carrier or excipient, an agent that increases epoxy-fatty acids (e.g., an sEHI or a pharmaceutically acceptable salt of the inhibitor and, optionally, one or more EETs or epoxides of EPA or of DHA, or of both), and optionally the second agent (e.g., antidepressant, mood stabilizer, anti-psychotic, anxiolytic). In some embodiments, the methods comprise administration of an sEHI and one or more epoxides of EPA or of DHA, or of both.

For preparing the pharmaceutical compositions, the pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component. In tablets, the active component is mixed with the carrier having the necessary binding properties in suitable proportions and compacted in the shape and size desired. The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution. Transdermal administration can be performed using suitable carriers. If desired, apparatuses designed to facilitate transdermal delivery can be employed. Suitable carriers and apparatuses are well known in the art, as exemplified by U.S. Pat. Nos. 6,635,274, 6,623,457, 6,562,004, and 6,274,166.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active components in water with viscous material, such as natural or synthetic gums, resins, methylcellulose, sodium carboxymethylcellulose, polyethylene glycols and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

A variety of solid, semisolid and liquid vehicles have been known in the art for years for topical application of agents to the skin. Such vehicles include creams, lotions, gels, balms, oils, ointments and sprays. See, e.g., Provost C. "Transparent oil-water gels: a review," Int J Cosmet Sci. 8:233-247 (1986), Katz and Poulsen, Concepts in biochemical pharmacology, part I. In: Brodie B B, Gilette J R, eds. Handbook of Experimental Pharmacology. Vol. 28. New York, NY: Springer; 107-174 (1971), and Hadgcraft, "Recent progress in the formulation of vehicles for topical applications," Br J Dermatol., 81:386-389 (1972). A number of topical formulations of analgesics, including capsaicin (e.g., Capsin®), so-called "counter-irritants" (e.g., Icy-Hot®), substances such as menthol, oil of wintergreen, camphor, or eucalyptus oil compounds which, when applied to skin over an area presumably alter or off-set pain in joints or muscles served by the same nerves) and salicylates (e.g. BenGay®), are known and can be readily adapted for topical administration of sEHI by replacing the active ingredient or ingredient with an sEHI, with or without EETs. It is presumed that the person of skill is familiar with these various vehicles and preparations and they need not be described in detail herein.

The agent that increases epoxy-fatty acids (e.g., an inhibitor of sEH, an epoxy-fatty acid, and mixtures thereof), optionally mixed with an anti-inflammatory and/or analgesic agent, can be mixed into such modalities (creams, lotions, gels, etc.) for topical administration. In general, the concentration of the agents provides a gradient which drives the agent into the skin. Standard ways of determining flux of drugs into the skin, as well as for modifying agents to speed or slow their delivery into the skin are well known in the art and taught, for example, in Osborne and Amann, eds., Topical Drug Delivery Formulations, Marcel Dekker, 1989. The use of dermal drug delivery agents in particular is taught in, for example, Ghosh et al., eds., Transdermal and Topical Drug Delivery Systems, CRC Press, (Boca Raton, FL, 1997).

In some embodiments, the agents are in a cream. Typically, the cream comprises one or more hydrophobic lipids, with other agents to improve the "feel" of the cream or to provide other useful characteristics. In one embodiment, for example, a cream may contain 0.01 mg to 10 mg of sEHI, with or without one or more EETs, per gram of cream in a white to off-white, opaque cream base of purified water USP, white petrolatum USP, stearyl alcohol NF, propylene glycol USP, polysorbate 60 NF, cetyl alcohol NF, and benzoic acid USP 0.2% as a preservative. In various embodiments, an agent that increases epoxy-fatty acids (e.g., an sEHI or a pharmaceutically acceptable salt of the inhibitor and, optionally, one or more EETs or epoxides of EPA or of DHA, or of both), and/or the second agent (e.g., antidepressant, mood stabilizer, anti-psychotic, anxiolytic) can be mixed into a commercially available cream, Vanicream® (Pharmaceutical Specialties, Inc., Rochester, MN) comprising purified water, white petrolatum, cetearyl alcohol and ceteareth-20, sorbitol solution, propylene glycol, simethicone, glyceryl monostearate, polyethylene glycol monostearate, sorbic acid and BHT.

In other embodiments, the agent or agents are in a lotion. Typical lotions comprise, for example, water, mineral oil, petrolatum, sorbitol solution, stearic acid, lanolin, lanolin alcohol, cetyl alcohol, glyceryl stearate/PEG-100 stearate, triethanolamine, dimethicone, propylene glycol, microcrystalline wax, tri (PPG-3 myristyl ether) citrate, disodium EDTA, methylparaben, ethylparaben, propylparaben, xanthan gum, butylparaben, and methyldibromo glutaronitrile.

In some embodiments, the agent is, or agents are, in an oil, such as jojoba oil. In some embodiments, the agent is, or agents are, in an ointment, which may, for example, white petrolatum, hydrophilic petrolatum, anhydrous lanolin, hydrous lanolin, or polyethylene glycol. In some embodiments, the agent is, or agents are, in a spray, which typically comprise an alcohol and a propellant. If absorption through the skin needs to be enhanced, the spray may optionally contain, for example, isopropyl myristate.

Whatever the form in which the agents that inhibit sEH are topically administered (that is, whether by solid, liquid, lotion, gel, spray, etc.), in various embodiments they are administered at a therapeutically effective dosage of about 0.01 mg to 10 mg per 10 cm$^2$. An exemplary therapeutically effective dose for systemic administration of an inhibitor of sEH is from about 0.1 μg/kg to about 100 mg/kg, e.g., about 0.001 mg/kg to about 10 mg/kg, e.g., about 0.01 mg/kg to about 1.0 mg/kg, body weight of the mammal. In various embodiments, dose and frequency of administration of an sEH inhibitor are selected to produce plasma concentrations within the range of 2.5 μM and 30 nM.

The agent that increases epoxy-fatty acids (e.g., an inhibitor of sEH, an epoxy-fatty acid, and mixtures thereof), optionally mixed with an anti-inflammatory and/or analgesic agent, can be introduced into the bowel by use of a suppository. As is known in the art, suppositories are solid compositions of various sizes and shapes intended for introduction into body cavities. Typically, the suppository comprises a medication, which is released into the immediate area from the suppository. Typically, suppositories are made using a fatty base, such as cocoa butter, that melts at body temperature, or a water-soluble or miscible base, such as glycerinated gelatin or polyethylene glycol.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as tablets, capsules, and powders in vials or ampoules. Also, the unit dosage form can be a capsule, tablet, cachet, or lozenge itself, or it can be the appropriate number of any of these in packaged form.

The term "unit dosage form", as used in the specification, refers to physically discrete units suitable as unitary dosages for human subjects and animals, each unit containing a predetermined quantity of active material calculated to produce the desired pharmaceutical effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification.

A therapeutically effective amount or a sub-therapeutic amount of the agent that increases epoxy-fatty acids can be co-administered with the second agent (e.g., antidepressant, mood stabilizer, anti-psychotic, anxiolytic). The dosage of the specific compounds depends on many factors that are well known to those skilled in the art. They include for example, the route of administration and the potency of the particular compound. An exemplary therapeutically effective dose is from about 0.1 μg/kg to about 100 mg/kg, e.g., about 0.001 mg/kg to about 10 mg/kg, e.g., about 0.01 mg/kg to about 1.0 mg/kg, body weight of the mammal. Determination of an effective amount is well within the capability of those skilled in the art.

Generally, an efficacious or effective amount of a combination of one or more agents is determined by first administering a low dose or small amount of a polypeptide or composition and then incrementally increasing the administered dose or dosages, adding a second or third medication as needed, until a desired effect of is observed in the treated subject with minimal or no toxic side effects. Applicable methods for determining an appropriate dose and dosing schedule for administration of a combination of the one or more agents are described, for example, in *Goodman and Gilman's The Pharmacological Basis of Therapeutics*, 12th Edition, 2010, McGraw-Hill Professional; in a Physicians' Desk Reference (PDR), 69$^{th}$ Edition, 2015 and 70$^{th}$ Edition, 2016, PDR Network; in *Remington: The Science and Practice of Pharmacy*, 21$^{st}$ Ed., 2005, supra; and in *Martindale: The Complete Drug Reference*, Sweetman, 2005, London: Pharmaceutical Press, and in Martindale, *Martindale: The Extra Pharmacopoeia*, 31st Edition, 1996, Amer Pharmaceutical Assn, each of which are hereby incorporated herein by reference.

EETs, EDPs, or EEQs are unstable, and can be converted to the corresponding diols, in acidic conditions, such as those in the stomach. To avoid this, EETs, EDPs, or EEQs can be administered intravenously or by injection. EETs, EDPs, or EEQs intended for oral administration can be encapsulated in a coating that protects the compounds during passage through the stomach. For example, the E EETs, EDPs, or EEQs can be provided with a so-called "enteric" coating, such as those used for some brands of aspirin, or embedded in a formulation. Such enteric coatings and formulations are well known in the art. In some formulations, the compositions are embedded in a slow-release formulation to facilitate administration of the agents over time.

It is understood that, like all drugs, sEHIs have half-lives defined by the rate at which they are metabolized by or excreted from the body, and that the sEHIs will have a period following administration during which they are present in amounts sufficient to be effective. If EETs, EDPs, or EpETEs are administered after the sEHI is administered, therefore, it is desirable that the EETs, EDPs, or EpETEs be administered during the period during which the sEHI are present in amounts to be effective in delaying hydrolysis of the EETs, EDPs, or EpETEs. Typically, the EETs, EDPs, or EpETEs are administered within 48 hours of administering an sEH inhibitor. Preferably, the EETs, EDPs, or EpETEs are administered within 24 hours of the sEHI, and even more preferably within 12 hours. In increasing order of desirability, the EETs, EDPs, or EpETEs are administered within 10, 8, 6, 4, 2, hours, 1 hour, or one half hour after administration of the inhibitor. When co-administered, the EETs, EDPs, or EpETEs are preferably administered concurrently with the sEHI.

In some embodiments, prior to administration of an agent that increases the level of epoxy-fatty acids, the individual to be treated has been previously diagnosed as having a neurodegenerative disorder.

8. Methods of Monitoring

Clinical efficacy can be monitored using any method known in the art. Measurable parameters to monitor efficacy will depend on the condition being treated. For monitoring the status or improvement of one or more symptoms associated with a neurodevelopmental disease, both subjective parameters (e.g., patient reporting) and objective parameters (e.g., reduction or elimination of an associated symptoms a with the neurodevelopmental disorder observable by a clinician or psychologist; brain scans; cognitive functions (e.g., verbal learning, speed of processing, attention/vigilance, working memory, visual learning, reasoning and problem solving, social cognition)). Symptoms for patients with psychiatric disorders can be measured and quantified using appropriate tests and scales established in the art, e.g., HAMD (Hamilton Depression Rating Scale) (Williams, *Arch Gen Psychiatry.* 1988 August; 45(8):742-7 and Zimmerman, et al., *J Affect Disord.* 2013 Sep. 5; 150(2):384-8), HAMA (Hamilton Anxiety Rating Scale) (Bruss, et al., *Psychiatry Res.* 1994 August; 53(2):191-202), YMRS (Young Mania Rating Scale) (Lukasiewicz, et al., *Int J Methods Psychiatr Res.* 2013 March; 22(1):46-58), BPRS (Brief Psychiatric Rating Scale) (Bell, et al., *J Nerv Ment Dis.* 1992 November; 180(11):723-8 and Lachar, et al., *J Am Acad Child Adolesc Psychiatry.* 2001 March; 40(3):333-40), PANSS (Positive and Negative Syndrome Scale) (Kay, et al., *Schizophr Bull.* 1987; 13(2):261-76 and Kay, et al., *Psychiatry Res.* 1988 January; 23(1):99-110), and/or CGS-I (Clinical Global Impression—Severity) (Pinna, et al., *Ann Gen Psychiatry.* 2015 Feb. 13; 14:6). Applicable assays or diagnostic parameters for the monitoring neurodevelopmental illness are known in the art, e.g., as set forth in the Diagnostic and Statistical Manual of Mental Disorders, 5th Edition (DSM-5) American Psychiatric Association, American Psychiatric Publishing, 2013 and/or the International Statistical Classification of Diseases and Related Health Problems (ICD)-11 of the World Health Organization (WHO) (available online at http://www.who.int/classifications/icd/en/). Behavioral changes in the subject (e.g., attitude, mood, appetite, grooming, sociability, energy levels, increased activity levels, weight gain/loss, exhibition of increased comfort) are also relevant to neurodevelopmental disorders. These parameters can be measured using any methods known in the art. In varying embodiments, the different parameters can be assigned a score. Further, the scores of two or more parameters can be combined to provide an index for the subject.

Observation of the stabilization, improvement and/or reversal of one or more symptoms or parameters by a measurable amount indicates that the treatment or prevention regime is efficacious. Observation of the progression, increase or exacerbation of one or more symptoms indicates that the treatment or prevention regime is not efficacious. For example, in the case of a neurodevelopmental disorders, observing the improvement of one or more subjective parameters (e.g., patient reporting); objective parameters (e.g., reduction or elimination of an associated symptoms a with the neurodevelopmental disorder observable by a clinician or psychologist); brain scans; cognitive functions (e.g., verbal learning, speed of processing, attention/vigilance, working memory, visual learning, reasoning and problem solving, social cognition)) and/or behavioral changes in the subject (e.g., attitude, mood, appetite, grooming, sociability, energy levels, increased activity levels, weight gain/loss, exhibition of increased comfort) after one or more administrations of an agent that increases epoxy-fatty acids (e.g., an inhibitor of sEH) indicates that the treatment or prevention regime is efficacious. Likewise, observation of reduction or decline, lack of improvement or worsening of one or both of subjective parameters (e.g., patient reporting) and objective parameters (e.g., reduction or elimination of an associated symptoms a with the neurodevelopmental disorder observable by a clinician or psychologist); brain scans; cognitive functions (e.g., verbal learning, speed of processing, attention/vigilance, working memory, visual learning, reasoning and problem solving, social cognition)), and/or behavioral changes in the subject (e.g., attitude, mood, appetite, grooming, sociability, energy levels, increased activity levels, weight gain/loss, exhibition of increased comfort) after one or more administrations of an agent that increases epoxy-fatty acids (e.g., an inhibitor of sEH) indicates that the treatment or prevention regime is not efficacious.

In certain embodiments, the monitoring methods can entail determining a baseline value of a measurable biomarker or disease parameter in a subject before administering a dosage of the one or more active agents described herein, and comparing this with a value for the same measurable biomarker or parameter after a course of treatment.

In other methods, a control value (i.e., a mean and standard deviation) of the measurable biomarker or parameter is determined for a control population. In certain embodiments, the individuals in the control population have not received prior treatment and do not have the disease condition subject to treatment, nor are at risk of developing the disease condition subject to treatment (e.g., do not have and are not at risk of developing a neurodevelopmental disorder). In such cases, if the value of the measurable biomarker or clinical parameter approaches the control value, then treatment is considered efficacious. In other embodiments, the individuals in the control population have not received prior treatment and have been diagnosed with the disease condition subject to treatment (e.g., has been diagnosed with a neurodevelopmental disorder). In such cases, if the value of the measurable biomarker or clinical parameter approaches the control value, then treatment is considered inefficacious.

In other methods, a subject who is not presently receiving treatment but has undergone a previous course of treatment is monitored for one or more of the biomarkers or clinical parameters to determine whether a resumption of treatment is required. The measured value of one or more of the biomarkers or clinical parameters in the subject can be compared with a value previously achieved in the subject after a previous course of treatment. Alternatively, the value measured in the subject can be compared with a control value (mean plus standard deviation) determined in population of subjects after undergoing a course of treatment. Alternatively, the measured value in the subject can be compared with a control value in populations of prophylactically treated subjects who remain free of symptoms of disease, or populations of therapeutically treated subjects who show amelioration of disease characteristics. In such cases, if the value of the measurable biomarker or clinical parameter approaches the control value, then treatment is considered efficacious and need not be resumed. In all of these cases, a significant difference relative to the control level (i.e., more than a standard deviation) is an indicator that treatment should be resumed in the subject.

9. Kits

Further provided herein are kits. In varying embodiments, the kits comprise one or more agents that increase the level of epoxy-fatty acids. In some embodiments, the kits further comprise one or more additional agents described herein.

Embodiments of the agents that increase the level of epoxy-fatty acids and embodiments of the additional agent(s) are as described above and herein. Embodiments of formulations of the agents are as described above and herein. In varying embodiments, the agent that increases the level of epoxy-fatty acids and the additional agent(s) can be co-formulated for administration as a single composition. In some embodiments, the agent that increases the level of epoxy-fatty acids and the additional agent(s) are formulated for separate administration, e.g., via the same or different route of administration. In varying embodiments, one or both the agent that increases the level of epoxy-fatty acids and the additional agent(s) are provided in unitary dosages in the kits.

Some of the kits described herein include a label describing a method of administering one or more agents that increase the level of epoxy-fatty acids and/or one or more additional therapeutic agents described herein.

10. Methods of Use

In further uses, the present disclosure demonstrates that treatment of an individual with an agent that increases the level of epoxy-fatty acids prevents the loss of parvalbumin and/or $GAD_{67}$ proteins in the prefrontal cortex of individuals receiving treatment.

As such, provided herein are methods for maintaining parvalbumin (PV) and/or glutamic acid decarboxylase ($GAD_{67}$) immunoreactivity in the medial prefrontal cortex (mPFC) of an individual comprising administering to said individual an agent that increases the level of epoxy-fatty acids.

EXAMPLES

The following examples are offered to illustrate, but not to limit the claimed invention.

Example 1

Key Role of Soluble Epoxide Hydrolase in the Neurodevelopmental Disorders of Offspring after Maternal Immune Activation Materials and Methods Animals and animal care. Pregnant ddY mice (embryo at the 5$^{th}$ day (E5), 9-10 weeks old) were purchased from Japan SLC Inc. (Hamamatsu, Shizuoka, Japan). Pregnant mice in each clear polycarbonate cage (22.5×33.8×14.0 cm) one by one were housed under controlled temperatures and 12-hour light/dark cycles (lights on between 07:00-19:00 h), with ad libitum food (CE-2; CLEA Japan, Inc., Tokyo, Japan) and water. The protocol was approved by the Chiba University Institutional Animal Care and Use Committee. This study was carried out in strict accordance with the recommendations in the Guide for the Care and Use of Laboratory Animals of the National Institutes of Health, USA.

Administration of poly(I:C) into pregnant mice. The schedule of poly(I:C) treatment was performed as reported previously (13,36-39). The pregnant mice were injected intraperitoneally (i.p.) for six consecutive days from E12 to E17 with poly(I:C) (5.0 mg/kg/day, Sigma-Aldrich Co. Ltd., St. Louis, MO, USA) dissolved in physiological saline, or an equivalent volume (5 ml/kg) of saline. The male offspring were separated from their mothers at wearing (P21), and mice were caged each three-five in the groups in clear polycarbonate cage (22.5×33.8×14.0 cm). Mice were housed under controlled temperatures and 12-hour light/dark cycles (lights on between 07:00-19:00 h), with ad libitum food and water.

Collection of brain samples and oxylipin profiling. The pregnant mice were injected i.p. with poly(I:C) (5.0 mg/kg/day for 6 days from E12 to E17) or saline, as described above. The male offspring were separated from their mothers at wearing (P21). On P28, mice were deeply anesthetized with isoflurane and brains were removed from the skulls. For Western blot analysis, brain regions such as prefrontal cortex (PFC), striatum, CA1, CA3 and dentate gyrus (DG) of the hippocampus were dissected from brain on ice using a Leica microscope S9E (Leica Microsystems, Tokyo, Japan). The samples were stored at −80° C. before assay. For oxylipin analysis, PFC, hippocampus, and cerebellum were dissected from brain on ice, and the samples were stored at −80° C. before assay. Measurement of eicosanoids was performed at UC Davis using the previous method (57).

Western blot analysis. Western blot analysis was performed as reported previously (22,26). Basically, the tissue samples were homogenized in Leammli lysis buffer. 50 μg of protein were measured using the DC protein assay kit (Bio-Rad), and incubated for 5 min at 95° C., with an equal volume of 125 mM Tris-HCl, pH6.8, 20% glycerol, 0.1% bromophenol blue, 10% β-mercaptoethanol, 4% sodium dodecyl sulfate, and subjected to sodium dodecyl sulfate polyacrylamide gel electrophoresis, using 7.5% or AnyKD mini-gels (Mini-PROTEAN® TGX™ Precast Gel; Bio-Rad, CA, USA). Proteins were transferred onto polyvinylidenedifluoride (PVDF) membranes using a Trans Blot Mini Cell (Bio-Rad). For immunodetection, the blots were blocked with 2% BSA in TBST (TBS+0.1% Tween-20) for 1 h at room temperature (RT), and kept with primary antibodies overnight at 4° C. The primary antibodies were used. The next day, blots were washed three times in TBST and incubated with horseradish peroxidase conjugated anti-rabbit or anti-mouse antibody 1 hour, at RT. After final three washes with TBST, bands were detected using enhanced chemiluminescence (ECL) prime Western Blotting Detection system (GE Healthcare Bioscience). Images were captured with a ChemDoc imaging system (Bio-Rad), and the immunoreactive bands were analysis by Image Lab software.

Gene expression analysis by quantitative real-time PCR. At juvenile (P28) stage, mice were sacrificed, and their brains were removed for measurement of gene expression of Ephx2 mRNA. Brain regions such as PFC, striatum, CA1, CA3 and DG of the hippocampus were dissected from brain on ice using a Leica microscope S9E (Leica Microsystems, Tokyo, Japan). A quantitative RT-PCR system (Step One Plus, Thermo Fisher Scientific, Yokohama, Japan) was used to measure mRNAs. The specific mRNA transcripts were quantified by TaqManGene Expression assays (Thermo Fisher Scientific, Yokohama, Japan). Expression levels of Ephx2 (Mm01313813_m1) was measured in brain tissue. Total RNA was extracted by use of an RNeasy Mini Kit (Qiagen, Hilden, Germany). The purity of total RNA was assessed by Biophotometer plus (Eppendorf, Hamburg, Germany). The RNA samples were used in the first strand cDNA synthesis with High Capacity cDNA Reverse Transcription Kit (#4368813 Thermo Fisher Scientific, Yokohama, Japan). All samples were tested in triplicate and average values were used for quantification. The average values were normalized to Vic-labeled Actb mRNA (Cat #4352341E: pre-developed TaqMan Assay Reagents, Thermo Fisher Scientific, Yokohama, Japan).

The study using iPSC was approved by the Ethics Committees of RIKEN, and conducted according to the principles expressed in the Declaration of Helsinki. Neurospheres from iPSC with two schizophrenia patients (two cell lines from each subject. Total of four cell lines) with 22q11.2 deletion and three healthy control subjects (total of four cell lines) (Table 8) were used. Total RNA from neurospheres was extracted using the RNeasy Mini Kit (Qiagen), as reported previously (33).

Postmortem brain tissues from ASD and age-matched control samples were obtained from the National Institute of Child Health and Human Development (NICHD) Brain and Tissue Bank, University of Maryland School of Medicine (http://medschool.umaryland.edu/btbank/), for gene expression analysis (Table 9) (34). Frozen tissue samples from BA09 (ASD; n=10, control; n=10), BA21 (ASD; n=14, control; n=14), and BA40 (ASD; n=14, control; n=13) were used. Total RNA from brain tissues was extracted using a miRNAeasy Mini kit (QIAGEN GmbH, Hilden, Germany) and single stranded cDNA was synthesized using a SuperScript VILO Master Mix (Life Technologies Co., Carlsbad, CA, USA), according to the manufacturers' instructions.

Real-time quantitative RT-PCR analysis was conducted using standard procedures, in a QuantStudio12K Flex Real-Time PCR System (Life Technologies Co., Carlsbad, CA, USA). TaqMan probes and primers for EPHX2 and GAPDH (internal control) were chosen from TaqMan Gene Expression Assays (ABI, Foster City, CA, USA). All real-time quantitative RT-PCR reactions were performed in triplicate, based on the standard curve method. To check for expressional changes between cases and controls, expression of EPHX2 [Hs00932316_m1], and GAPDH [Hs02758991_g1] were measured using TaqMan Gene Expression Assays in a QuantStudio12K Flex Real-Time PCR System (Life Technologies Co., Carlsbad, CA, USA).

Experiments of TPPU in drinking water. For experiment of TPPU (synthesized at UC Davis, CA) in drinking water in juvenile and adolescent stages, TPPU (15 mg/L) or water in drinking water was given in the male offspring from P28 to P56. Subsequently, normal water was given to all groups for 4 weeks (P57-P84). Behavioral tests of adult offspring were performed during adulthood (P70-P84) after prenatal poly(I:C) injections (FIG. 4A).

For experiment of TPPU in drinking water in pregnant stages, TPPU (15 mg/L) or water in drinking water was given in the pregnant mice from E12 to P21. Subsequently, normal water was given to all groups for 2 weeks (P21-P42). Behavioral tests of offspring were performed during juvenile stage (P28-P42) after prenatal poly(I:C) injections (FIG. 6A).

Behavioral analysis. Locomotion and the novel object recognition test (NORT) were performed as reported previously (36-39,58,59). Locomotor Activity: Both horizontal and rearing activity were monitored by an infrared ray passive sensor system (SCANET-SV10, Melquest Ltd., Toyama, Japan), and activity was integrated every minute. Individual mice were placed in activity chambers and allowed 1 hour of free exploration as spontaneous activity.

Novel Object Recognition Test (NORT): Mice were habituated for 10 minutes in the box for 3 straight days. At 4th day, two objects (differing in shape and color but of similar size) were placed in the box 35.5 cm apart (symmetrically), and each animal was allowed to explore in the box for 5 minutes. The animals were considered to be exploring the object when the head of the animal was both facing and within 2.54 cm of the object or when any part of the body, except for the tail was touching the object. The time that mice spent exploring each object was recorded. After training, mice were immediately returned to their home cages, and the box and objects were cleaned with 75% ethanol, to avoid any possible instinctive odorant cues. Retention tests were carried out at one-day intervals, following the respective training. During the retention test, each mouse was reintroduced into their original test box, and one of the training objects was replaced by a novel object. The mice were then allowed to explore freely for 5 minutes, and the time spent exploring each object was recorded. Throughout the experiments, the objects were counter-balanced, in terms of their physical complexity and emotional neutrality. A preference index, that is, the ratio of time spent exploring either of the two objects (training session) or the novel object (retention test session) over the total time spent exploring both objects, was used.

Three-chamber Social Interaction Test: The three-chamber social interaction test was performed to investigate sociability and preference for social novelty in mice. The apparatus consisted of a rectangular, three-chambered box and a lid with a video camera (BrainScience Idea, Co., Ltd, Osaka, Japan). Each chamber (22.5 cm×41 cm×62 cm) was divided by a clear plastic wall with a small square opening (5 cm×8 cm). First, each subject mouse was placed in the box and allowed to explore for 10 min to habituate the environment. During the session, an empty wire cage (10 cm in diameter, 17.5 cm in height, with vertical bars 0.3 cm apart) was located in the corner of each chamber. Next, an unfamiliar ddY male mouse (stranger 1) that had had no prior contact with the subject mouse was put into a wire cage that was placed into one of the side chambers. To assess sociability, the subject mouse was allowed to explore the box for an additional 10-min session. Finally, to evaluate social preference for a new stranger, a second stranger male mouse (stranger 2) was placed into the wire cage that had been empty during the first 10-min session (social novelty preference test). Thus, the subject mouse had a choice between the first, now-familiar mouse (stranger 1) and the novel unfamiliar mouse (stranger 2). The time spent in each chamber and the time spent around each cage was recorded on video.

Immunohistochemistry. Immunohistochemistry of PV was performed as reported previously (37,39,59,60). Mice were anesthetized with 5% isoflurane and sodium pentobarbital (50 mg/kg), and perfused transcardially with 10 mL of physiological saline, followed by 40 mL of ice-cold 4% paraformaldehyde in 0.1M phosphate buffer (pH 7.4). Brains were removed from the skulls and post fixed overnight at 4° C. in the same fixative. For the immunohistochemical analysis, 50 µm-thick serial, coronal sections of brain tissue were cut in ice-cold 0.01M phosphate buffered saline (pH 7.5) using a vibrating blade microtome (VT1000s, Leica Microsystems, Tokyo, Japan). Free-floating sections were treated with 0.3% $H_2O_2$ in 50 mM Tris-HCl saline (TBS) for 30 min and were blocked in TBS containing 0.2% Triton X-100 (TBST) and 1.5% normal serum for 1 h at room temperature. The samples were then incubated for 24 h at 4° C. with mouse polyclonal anti-parvalbumin (PV) antibody or mouse anti-$GAD_{67}$ (Table 4). The sections were washed three times in TBS and then processed using the avidin-biotin-peroxidase method (Vectastain Elite ABC, Vector Laboratories, Inc., Burlingame, CA, USA). Sections were incubated for 3 min in a solution of 0.25 mg/mL DAB containing 0.01% $H_2O_2$. Then, sections were mounted on gelatinized slides, dehydrated, cleared, and cover slipped under Permount® (Fisher Scientific, Fair Lawn, NJ, USA). The sections were imaged, and the staining intensity of PV (or GADO immunoreactivity in the inflalimbic (IL) and prelimbic (PrL) regions of mPFC was analyzed using a light micro-scope equipped with a CCD camera (Olympus IX70, Tokyo, Japan) and the SCION IMAGE software package. Images of sections within mPFC region were captured using a 100× objective with a Keyence BZ-X710 microscope (Keyence Corporation, Osaka, Japan).

TABLE 4

Information of primary antibodies used in this study

| Antibodies | Species, Isotype | Label | Dilution (or Concentration) | Name of company | Catalog number |
|---|---|---|---|---|---|
| Parvalbumin (PV) | Mouse IgG | — | 1:5000 | Swant | #235 |
| GAD67 | Mouse IgG | — | 1:1000 | Merk | #MAB5406 |
| Phospho-PERK (Thr980) | Rabbit IgG | — | 1:1000 | Cell Signaling Technology | #3179 |
| PERK | Rabbit IgG | — | 1:1000 | Cell Signaling Technology | #3192 |
| elF2α | Rabbit IgG | — | 1:1000 | Cell Signaling Technology | #5324 |
| Bip | Rabbit IgG | — | 1:1000 | Cell Signaling Technology | #3177 |
| IRE1α(phospho S724) | Rabbit IgG | — | 1:1000 | abcam | ab38187 |
| IRE1α | Rabbit IgG | — | 1:1000 | Cell Signaling Technology | #3294 |
| XBP-1s | Rabbit IgG | — | 1:1000 | Cell Signaling Technology | #12782 |
| JNK1 + JNK2(phspho T183 + Y185) | Rabbit IgG | — | 1:1000 | abcam | ab4821 |
| JNK1 + JNK2 | Rabbit IgG | — | 1 µg/ml | abcam | ab112501 |
| ATF6 | Rabbit IgG | — | 1:1000 | Cell Signaling Technology | #65880 |
| Phospho-p38 MAPK(Thr180/Tyr182) | Rabbit IgG | — | 1:1000 | Cell Signaling Technology | #4511 |
| p38 MAPK | Rabbit IgG | — | 1:1000 | Cell Signaling Technology | #8690 |
| mouse sEH | Rabbit IgG | — | 1:5000 | UC Davis | — |
| β-actin | Mouse IgG | — | 1:10000 | Sigma-Aldrich | A5441 |

Statistical analysis. Analysis of the data was performed using GraphPad Prism (La Jolla, CA). Comparisons between two groups were performed using Student t-test. Comparisons among four groups were performed using the two-way analysis of variance (ANOVA), followed by Fisher's LSD test. The P-values of less than 0.05 were considered statistically significant.

Results

Figure 1A:
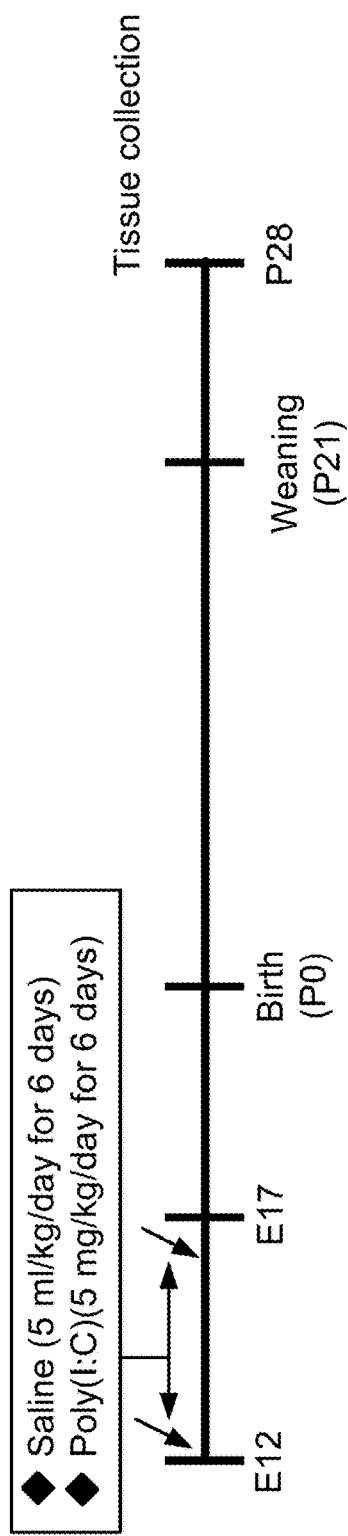
FIG. 1A-D Increased expression of sEH and decreased levels of epoxy fatty acids in the brain from juvenile offspring after MIA. (A): Schedule of treatment and brain collection. (B): Protein expression of sEH in the mouse brain regions from juvenile offspring after prenatal poly(I:C) exposure. Data are shown as mean±S.E.M. (n=7 or 8). *P<0.05 compared to control group (two-tailed Student t-test). N.S.: not significant. (C): Gene expression of Ephx2 mRNA in the mouse brain regions from juvenile offspring after prenatal poly(I:C) exposure. Data are shown as mean±S.E.M. (n=6). **P<0.01 compared to control group (two-tailed Student t-test). N.S.: not significant. (D): Tissue levels of four EpFAs such as 10,11-EpDPE, 11,12-EpETrE, 8,9-EpETrE, and 5,6-EpETrE in the PFC from juvenile offspring after MIA. The values represent the mean±S.E.M. (n=10 or 11). *P<0.05, **P<0.01 compared to control group (two-tailed Student t-test). N.S.: not significant.
Figure 1B:
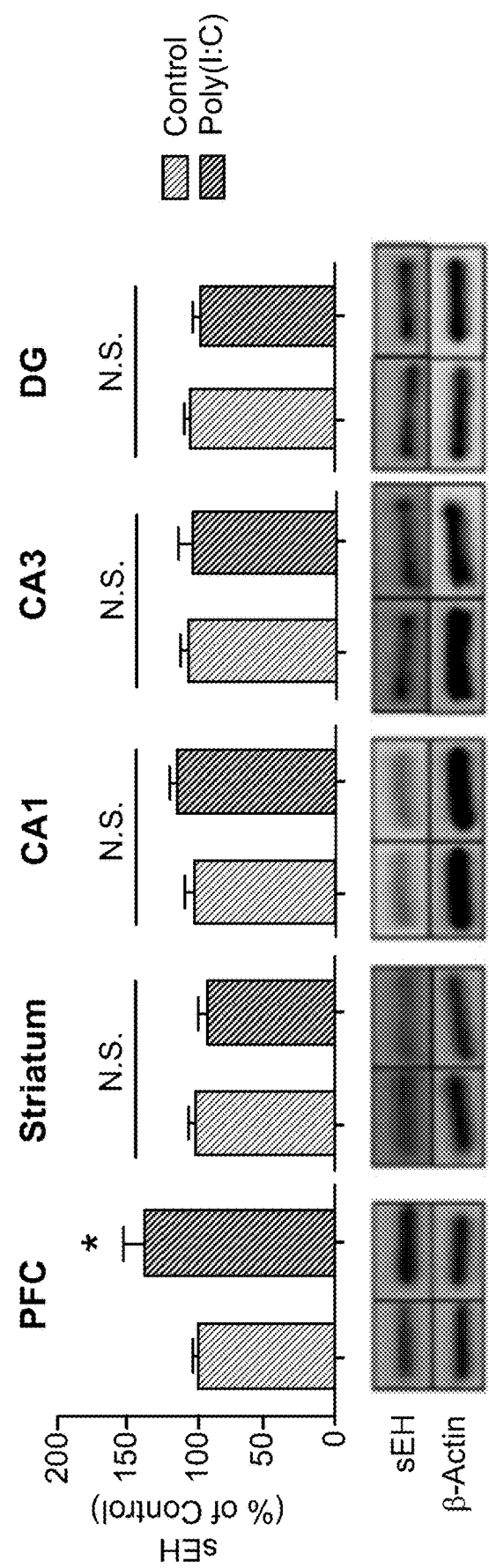
Figure 1C:
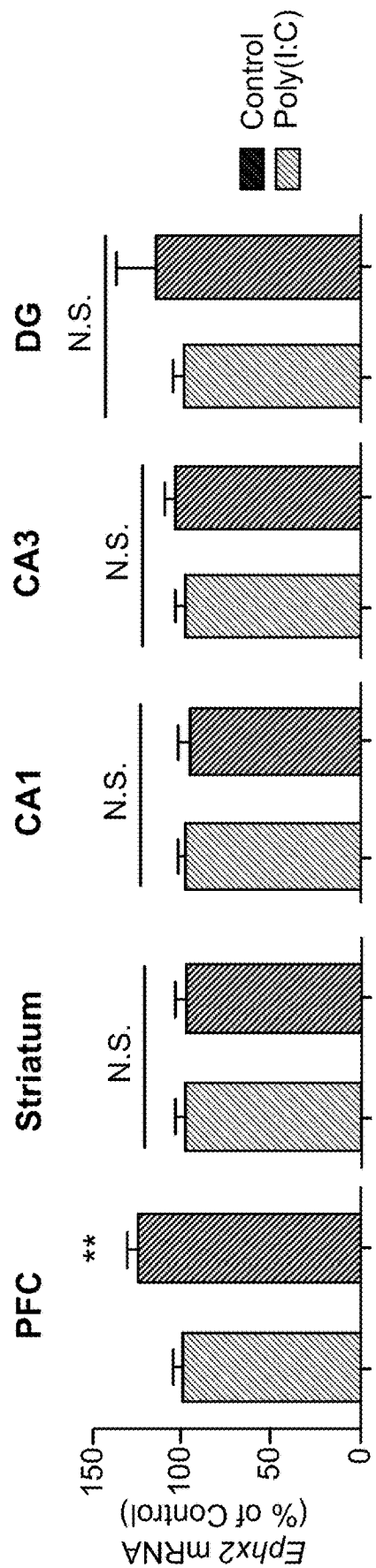

Levels of sEH and eicosanoid metabolites in the brain from juvenile offspring after MIA. First, we examined whether expressions of sEH are altered in the brain regions from juvenile offspring after neonatal poly(I:C)(5 mg/kg/day from E12 to E17) exposure (FIG. 1A). Levels of sEH in the PFC from juvenile offspring from poly(I:C)-treated mice are significantly higher than those of saline-treated mice (FIG. 1B). In contrast, there were no changes of sEH in other brain regions such as striatum, and hippocampus (CA1, CA3, dentate gyrus (DG)) (FIG. 1B). Furthermore, expressions of sEH (or Ephx2) mRNA in the PFC, but not other regions, from juvenile offspring from poly(I:C)-treated mice are significantly higher than those of saline-treated mice (FIG. 1C).

Figure 1D:
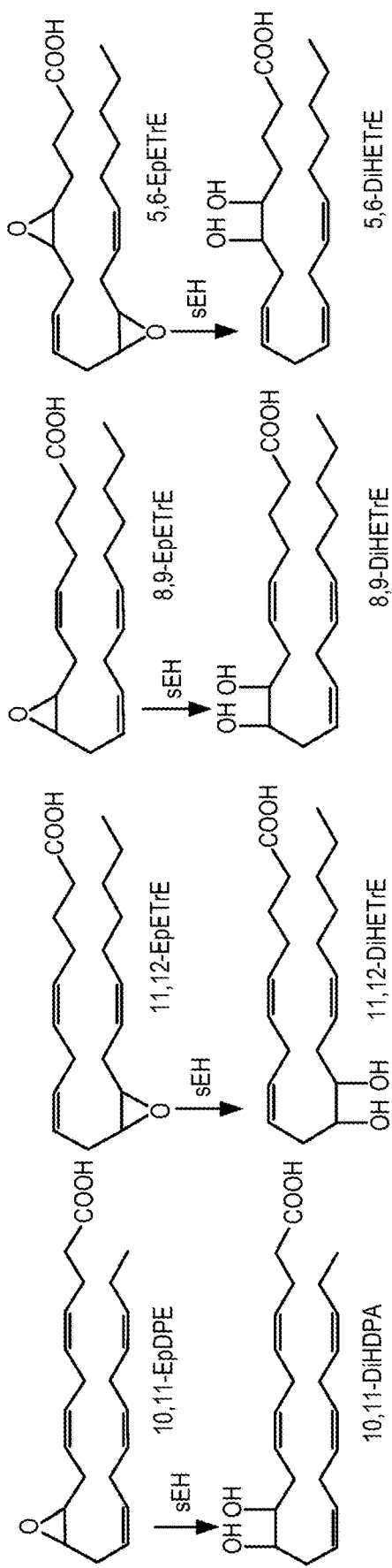
Figure 1D:
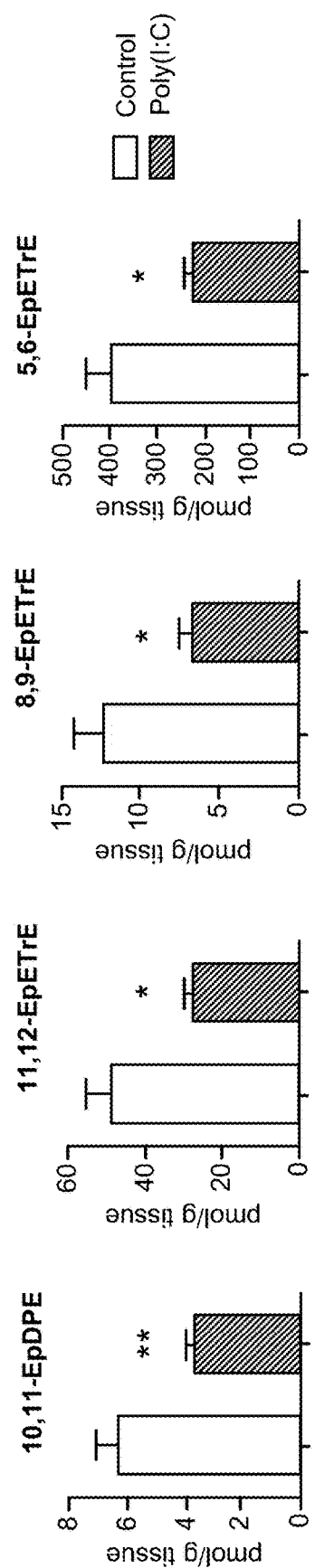
Figure 2:
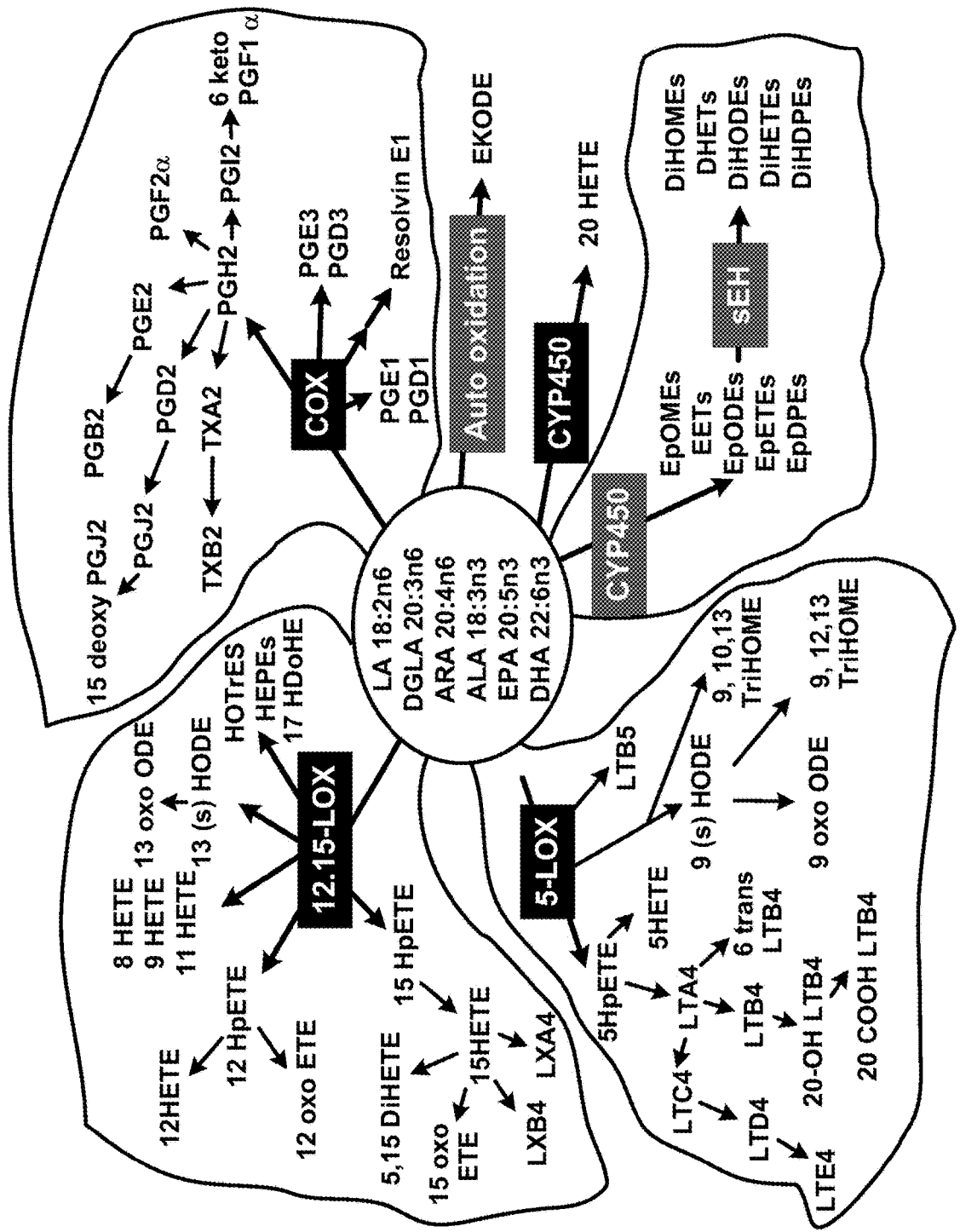
FIG. 2 illustrates the eicosanoids measured in the brain regions from male juvenile offspring after MIA.

Using oxylipin analysis, we measured tissue levels of eicosanoid metabolites in the PFC, hippocampus, and cerebellum from juvenile offspring after neonatal poly(I:C)(or saline) exposure (FIG. 2, Table 5-Table 7). Tissue levels of 10,11-EpDPE [10,11-epoxy-4Z,7Z,13Z,16Z,19Z-docosapentaenoic acid], 11,12-EpETrE [(5Z,8Z,14Z)-11,12-epoxyicosa-5,8,14-trienoate], 8,9-EpETrE [8,9-epoxy-5Z,11Z,14Z-eicosatrienoic acid], 5,6-EpETrE [N-((+/+5,6-epoxy-8Z,11Z,14Z-eicosatrienoyl)-ethanolamine], and 6-keto-PGF1α in the PFC from juvenile offspring after MIA were significantly lower than those of control mice (FIG. 1D and Table 5). In contrast, tissue levels of 19,20-DiHDPE [(4Z,7Z,10Z,13Z,16Z)-19,20-dihydroxydocosa-4,7,10,13,16-pentaenoic acid] in the PFC from juvenile offspring after MIA were significantly higher than those of control mice. Lower levels of these epoxy-eicosanoids [10,11-EpDPE, 11,12-EpETrE, 8,9-EpETrE, 5,6-EpETrE] in the PFC from juvenile offspring after MIA support the increased expression of sEH in this region. Furthermore, tissue levels of thromboxane B2, 19,20-DiHDPE, EKODE [12,13-epoxy 9-keto-10(trans)-octadecenoic acid], and 9-oxo-ODE [9-oxo-10E,12Z-octadecadienoic acid] in the hippocampus from juvenile offspring after MIA were significantly higher than those of control mice (Table 6). In contrast, there were no changes of eicosanoid metabolites in the cerebellum between two groups (Table 7).

TABLE 5

Levels of eicosanoid metabolites in the PFC from juvenile offspring

| Compounds | Control | Poly(I:C) | P value |
|---|---|---|---|
| 6-keto-PGF1α | 29.700 ± 2.627 | 22.088 ± 1.785 | 0.032 |
| Thromboxane 2 | 33.788 ± 3.503 | 43.922 ± 3.349 | 0.053 |
| 9,12,13-TriHOME | 51.554 ± 7.229 | 39.728 ± 6.854 | 0.254 |
| 9,10,13-TriHOME | 29.975 ± 4.266 | 22.676 ± 3.814 | 0.223 |
| PGF2a | 82.064 ± 5.492 | 86.798 ± 6.454 | 0.581 |
| PGE2 | 23.754 ± 6.369 | 16.359 ± 1.175 | 0.294 |
| PGD2 | 123.52 ± 9.281 | 147.79 ± 9.748 | 0.089 |
| 15,16-DiHODE | 1.868 ± 0.197 | 2.785 ± 0.414 | 0.054 |
| 12,13-DiHOME | 8.281 ± 2.107 | 4.640 ± 0.477 | 0.127 |
| 9,10-DiHOME | 1.057 ± 0.285 | 1.069 ± 0.188 | 0.972 |
| 19,20-DiHDPE | 2.910 ± 0.273 | 4.319 ± 0.331 | 0.004 |
| EKODE | 9.386 ± 1.782 | 6.552 ± 1.725 | 0.271 |
| 13-HODE | 44.173 ± 11.783 | 31.020 ± 5.237 | 0.340 |
| 9-HODE | 28.921 ± 5.534 | 24.253 ± 3.782 | 0.505 |
| 15-HETE | 67.926 ± 4.005 | 68.997 ± 4.672 | 0.863 |
| 11-HETE | 67.003 ± 3.854 | 72.292 ± 5.677 | 0.443 |
| 9-oxo-ODE | 20.059 ± 3.553 | 15.032 ± 2.690 | 0.283 |
| 12-HETE | 44.580 ± 10.506 | 28.597 ± 2.727 | 0.179 |
| 12,13-EpOME | 4.671 ± 1.039 | 2.934 ± 0.435 | 0.157 |
| 14,15-EpETrE | 61.25 ± 14.305 | 30.74 ± 5.605 | 0.074 |
| 9,10-EpOME | 4.397 ± 1.079 | 2.695 ± 0.424 | 0.177 |
| 10,11-EpDPE | 6.274 ± 0.763 | 3.698 ± 0.292 | 0.008 |
| 11,12-EpETrE | 46.674 ± 8.181 | 26.639 ± 3.530 | 0.045 |
| 8,9-EpETrE | 12.390 ± 2.101 | 6.725 ± 0.892 | 0.029 |
| 5,6-EpETrE | 397.82 ± 61.53 | 222.07 ± 22.38 | 0.020 |

The value (pmol/g tissue) are the mean ± SEM (n = 10).

The bold is statistically significant.

TABLE 6

Levels of eicosanoid metabolites in the hippocampus from juvenile offspring

| Compounds | Control | Poly(I:C) | P value |
|---|---|---|---|
| 6-keto-PGF1α | 61.959 ± 7.219 | 47.853 ± 3.589 | 0.109 |
| Thromboxane B2 | 48.930 ± 4.565 | 65.491 ± 5.906 | 0.038 |
| 9,12,13-TriHOME | 56.011 ± 6.305 | 54.137 ± 3.954 | 0.809 |
| 9,10,13-TriHOME | 31.976 ± 3.810 | 31.142 ± 2.301 | 0.858 |
| PGF2a | 155.85 ± 9.119 | 153.113 ± 10.00 | 0.842 |
| PGE2 | 21.946 ± 1.541 | 20.186 ± 1.410 | 0.415 |
| PGD2 | 127.00 ± 5.897 | 119.25 ± 8.999 | 0.472 |
| 15,16-DiHODE | 1.845 ± 0.176 | 2.295 ± 0.364 | 0.266 |
| 12,13-DiHOME | 3.970 ± 0.218 | 4.478 ± 0.528 | 0.476 |
| 9,10-DiHOME | 0.557 ± 0.089 | 0.814 ± 0.116 | 0.092 |
| 19,20-DiHDPE | 2.919 ± 0.227 | 4.228 ± 0.321 | 0.004 |
| EKODE | 10.97 ± 1.241 | 14.86 ± 0.949 | 0.026 |
| 13-HODE | 40.789 ± 2.783 | 41.916 ± 2.454 | 0.767 |
| 9-HODE | 31.405 ± 1.996 | 34.887 ± 1.969 | 0.233 |
| 15-HETE | 95.073 ± 6.050 | 100.514 ± 6.210 | 0.539 |
| 11-HETE | 95.154 ± 5.569 | 106.263 ± 6.366 | 0.218 |
| 9-oxo-ODE | 16.67 ± 1.280 | 24.50 ± 1.957 | 0.003 |
| 12-HETE | 89.02 ± 21.57 | 83.22 ± 12.09 | 0.823 |
| 12,13-EpOME | 4.829 ± 0.544 | 4.641 ± 0.393 | 0.788 |
| 14,15-EpETrE | 43.926 ± 5.373 | 45.020 ± 3.734 | 0.872 |
| 9,10-EpOME | 3.228 ± 0.303 | 3.933 ± 0.304 | 0.120 |
| 10,11-EpDPE | 5.297 ± 0.398 | 6.103 ± 0.347 | 0.149 |
| 11,12-EpETrE | 47.81 ± 4.042 | 42.05 ± 3.911 | 0.323 |
| 8,9-EpETrE | 13.32 ± 1.066 | 10.53 ± 0.809 | 0.056 |
| 5,6-EpETrE | 388.14 ± 25.47 | 333.09 ± 30.68 | 0.182 |

The value (pmol/g tissue) are the mean ± SEM (n = 10).
The bold is statistically significant.

TABLE 7

Levels of eicosanoid metabolites in the cerebellum from juvenile offspring

| Compounds | Control | Poly(I:C) | P value |
|---|---|---|---|
| 6-keto-PGF1a | 30.060 ± 3.729 | 29.69 ± 1.379 | 0.928 |
| TXB2 | 12.13 ± 1.042 | 14.62 ± 0.876 | 0.087 |
| 9,12,13-TriHOME | 49.40 ± 5.976 | 37.62 ± 5.925 | 0.181 |
| 9,10,13-TriHOME | 28.21 ± 3.566 | 20.84 ± 3.099 | 0.138 |
| PGF2a | 59.74 ± 7.023 | 46.32 ± 3.830 | 0.113 |
| PGE2 | 9.092 ± 1.281 | 6.969 ± 0.684 | 0.163 |
| PGD2 | 22.57 ± 2.637 | 21.60 ± 1.774 | 0.764 |
| 15,16-DiHODE | 2.293 ± 0.380 | 2.772 ± 0.423 | 0.411 |
| 12,13-DiHOME | 6.207 ± 0.768 | 5.406 ± 0.682 | 0.542 |
| 9,10-DiHOME | 1.055 ± 0.123 | 1.283 ± 0.279 | 0.466 |
| 19,20-DiHDPE | 6.984 ± 0.780 | 9.767 ± 0.858 | 0.029 |
| EKODE | 8.319 ± 1.046 | 7.801 ± 1.325 | 0.763 |
| 13-HODE | 34.35 ± 3.711 | 30.47 ± 4.048 | 0.490 |
| 9-HODE | 26.02 ± 2.772 | 23.33 ± 2.571 | 0.487 |
| 15-HETE | 38.05 ± 5.689 | 36.59 ± 3.256 | 0.827 |
| 12-HETE | 33.32 ± 4.798 | 34.19 ± 3.215 | 0.881 |
| 9-oxo-ODE | 18.31 ± 1.684 | 16.56 ± 2.802 | 0.599 |
| 12-HETE | 59.43 ± 18.09 | 75.46 ± 28.38 | 0.640 |
| 12,13-EpOME | 3.087 ± 0.296 | 2.989 ± 0.423 | 0.852 |
| 14,15-EpETrE | 24.50 ± 4.194 | 26.63 ± 3.595 | 0.704 |
| 9,10-EpOME | 3.251 ± 0.405 | 3.076 ± 0.662 | 0.824 |
| 10,11-EpDPE | 6.726 ± 1.295 | 6.061 ± 0.717 | 0.659 |
| 11,12-EpETrE | 24.260 ± 4.597 | 21.10 ± 1.869 | 0.533 |
| 8,9-EpETrE | 6.760 ± 1.641 | 5.453 ± 0.582 | 0.464 |
| 5,6-EpETrE | 186.72 ± 29.47 | 174.37 ± 11.71 | 0.702 |

The value (pmol/g tissue) are the mean ± SEM (n = 10).

Figure 3A:
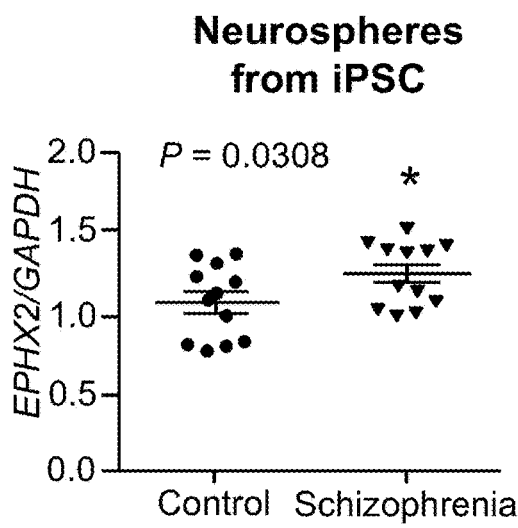
FIG. 3A-D Decreased expression of EPHX2 mRNA in the neurospheres from iPSC of schizophrenia patients and post-mortem brain samples from ASD patients. (A): Gene expression of EPHX2 mRNA in the neurospheres from iPSC from schizophrenia patients with 22q11.2 deletion was significantly higher than that of healthy controls. Data are shown as mean±S.D. (n=12). *P<0.05 compared to control group (one-tailed Student t-test). (B-D): Gene expression of EPHX2 mRNA in the BA09 and BA40, but not BA21, from ASD patients was significantly higher than that of controls. Data are shown as mean±S.D. *P<0.05, **P<0.01 compared to control group (one-tailed Student t-test).

Increased expression of sEH in the neurospheres from iPSCs from patients with schizophrenia and postmortem brain samples from ASD patients. Induced pluripotent stem cell (iPSC) technologies have provided an unprecedented opportunity to establish pluripotent stem cells from patients with schizophrenia and differentiate them into neuronal lineage, enabling an in vitro recapitulation of the pathogenesis of the disease (32). Previously, we reported that expression of sEH in the parietal cortex [Brodmann area (BA) 7] from schizophrenia patients was significantly higher than that of controls (22). Therefore, we measured whether sEH gene expression alters in the neurospheres from iPSCs from schizophrenia patients with the 22q11.2 deletion (Table 8) and healthy controls (33). Expression of EPHX2 mRNA in the neurospheres from iPSCs with schizophrenia patients was significantly higher than that of healthy control subjects (FIG. 3A).

TABLE 8

Summary of the iPSC lines from healthy controls and schizophrenia patients with 22q11.2 deletion

| Sample ID | iPSC Line ID | Line ID | Diagnosis | Gender | Age | Reference |
|---|---|---|---|---|---|---|
| C1-1 | 201B7 | NS1, NS2, NS3 | Control | F | 36 | Takashi et al (61) |
| C1-2 | YA9 | NS1, NS2, NS3 | | | | Imaizumi et al (62) |
| C3 | WD39 | NS1, NS2, NS3 | Control | F | 17 | Imaizumi et al (62) |
| C4 | KA23 | NS1, NS2, NS3 | Control | M | 40 | Matsumoto et al (63) |
| S1-1 | SA001_1D2 | NS1, NS2, NS3 | Schizophrenia | F | 37 | Toyoshima et al (63) |
| S1-2 | SA001_3B1 | NS1, NS2, NS3 | | | | |
| S2-1 | K0001_19 | NS1, NS2, NS3 | Schizophrenia | F | 30 | Toyoshima et al (63) |
| S2-2 | K0001_25 | NS1, NS2, NS3 | | | | |

Figure 3B:
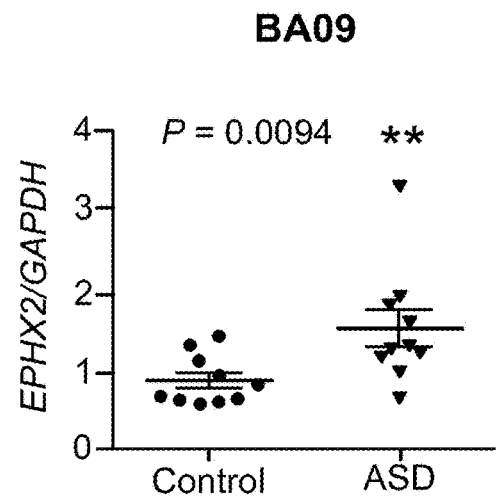
Figure 3C:
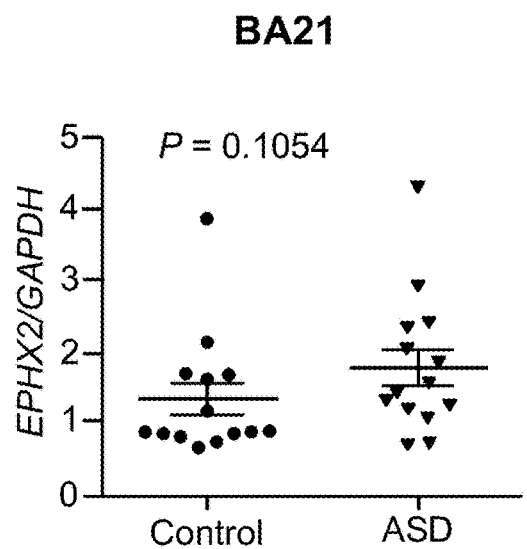
Figure 3D:
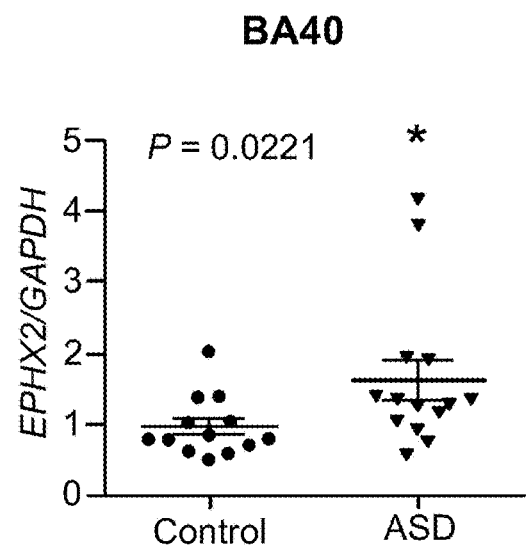

Next, we measured expression of EPHX2 mRNA in the postmortem brain samples (BA09, BA21, BA40) from ASD patients and age- and gender-matched controls (Table 9) (34). Expression of EPHX2 mRNA in the BA09 and BA40 from ASD patients was significantly higher than that of controls (FIG. 3B and FIG. 3D). Expression of EPHX2 mRNA in the BA21 from ASD patients was slightly higher than that of controls; but statistical analysis did not reach statistical significance (FIG. 3C). Collectively, it is likely that increased expression of sEH may play a role in the pathogenesis of schizophrenia and ASD.

TABLE 9

Demographic details of ASD and control brain samples from the NICHD Brain and Tissue Bank, University of Maryland School of Medicine

| | BA09 (CONT) | BA09 (ASD) | BA21(CONT) | BA21 (ASD) | BA40 (CONT) | BA40 (ASD) |
|---|---|---|---|---|---|---|
| Age | 13.70 ± 5.72 | 13.50 ± 5.87 | 12.43 ± 5.45 | 12.21 ± 5.62 | 12.85 ± 5.43 | 12.21 ± 5.62 |
| Gender | 3/7 (F/M) | 3/7 (F/M) | 4/10 (F/M) | 4/10 (F/M) | 4/9 (F/M) | 4/10 (F/M) |
| PMI (hr) | 16.60 ± 7.32 | 22.50 ± 12.87 | 16.43 ± 6.30 | 22.36 ± 12.37 | 16.77 ± 6.42 | 22.36 ± 12.37 |
| RIN | 6.29 ± 1.02 | 5.75 ± 1.39 | 5.79 ± 1.28 | 4.84 ± 1.58 | 6.03 ± 0.96 | 5.84 ± 1.57 |

The value is the mean ± SD.
CONT: Control,
ASD: Autism spectrum disorder.
PMI: Post mortem interval.
RIN RNA Integrity Number.
F: Female,
M: Male Effects of TPPU treatment during juvenile and adolescent stages on cognitive deficits and reduction of PV- and $GAD_{67}$-IR in the mPFC of adult offspring after MIA. Cognitive impairment is the core symptom in patients with schizophrenia (35). Previously, we reported that juvenile offspring of prenatal poly(I:C)-treated mice showed cognitive deficits and the reduction of PV-IR in the mPFC (36-39). Here we examined whether TPPU (15 mg/L) in drinking water during juvenile and adolescent stages (from P28 to P56) could prevent cognitive deficits and reduction of PV-IR in the mPFC of adult offspring after MIA. In the open field test, locomotion was unchanged among the four groups (FIG. 4B). There was no difference among the four groups in training sessions of novel object recognition test (NORT). However, in the retention session of NORT, the exploratory preference of the poly(I:C)+TPPU group was significantly higher than that of the poly(I:C)+water group (FIG. 4C). These findings suggest that TPPU in drinking water from P28 to P56 could improve cognitive deficits in adult offspring after MIA.

Figure 4D:
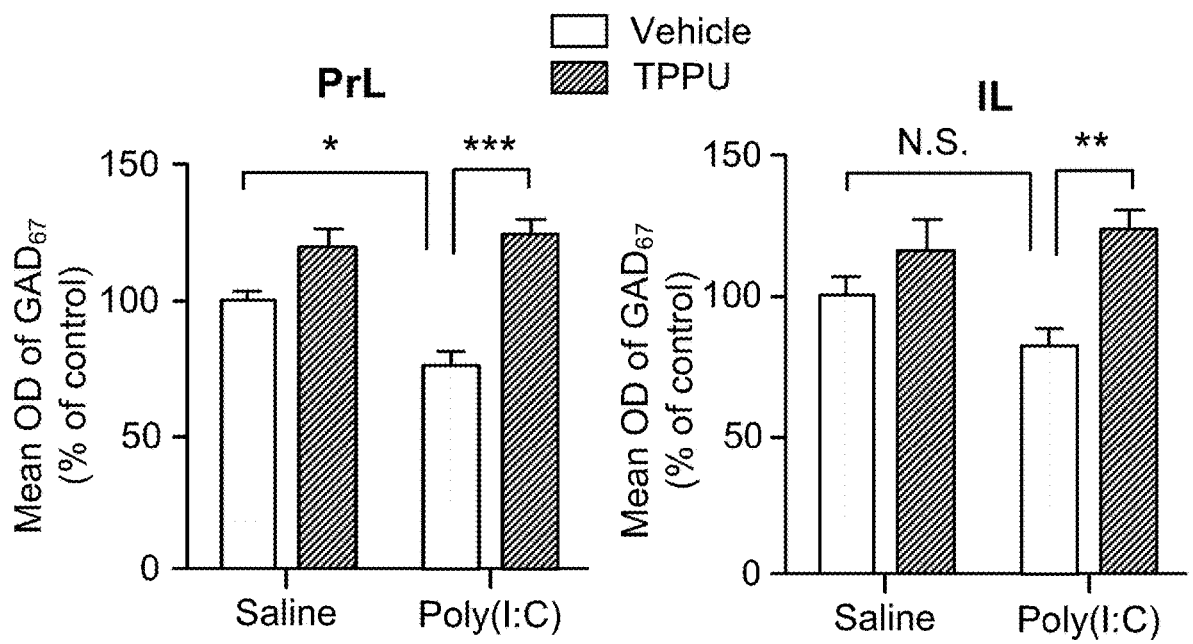
Figure 4D:
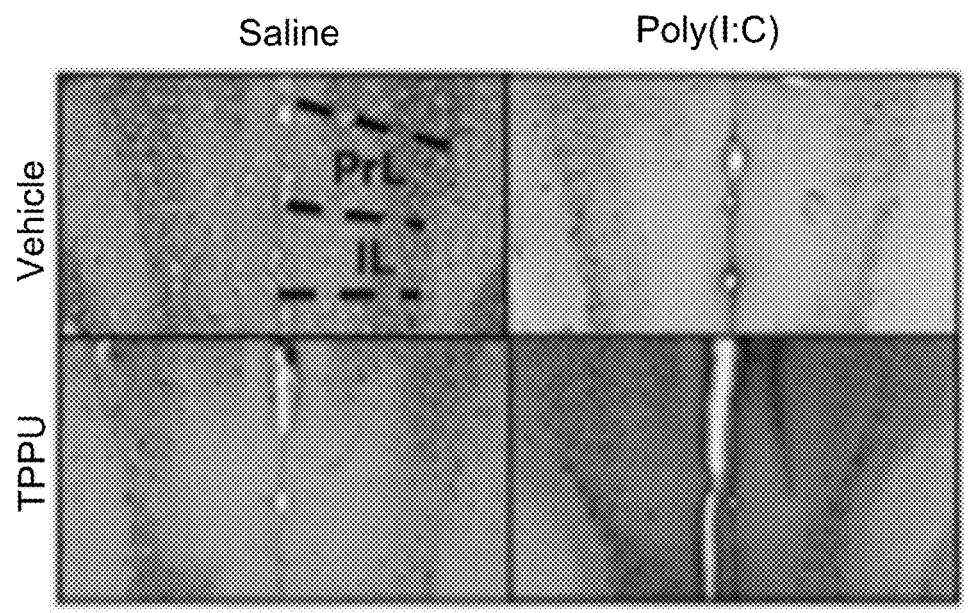
Figure 4D:
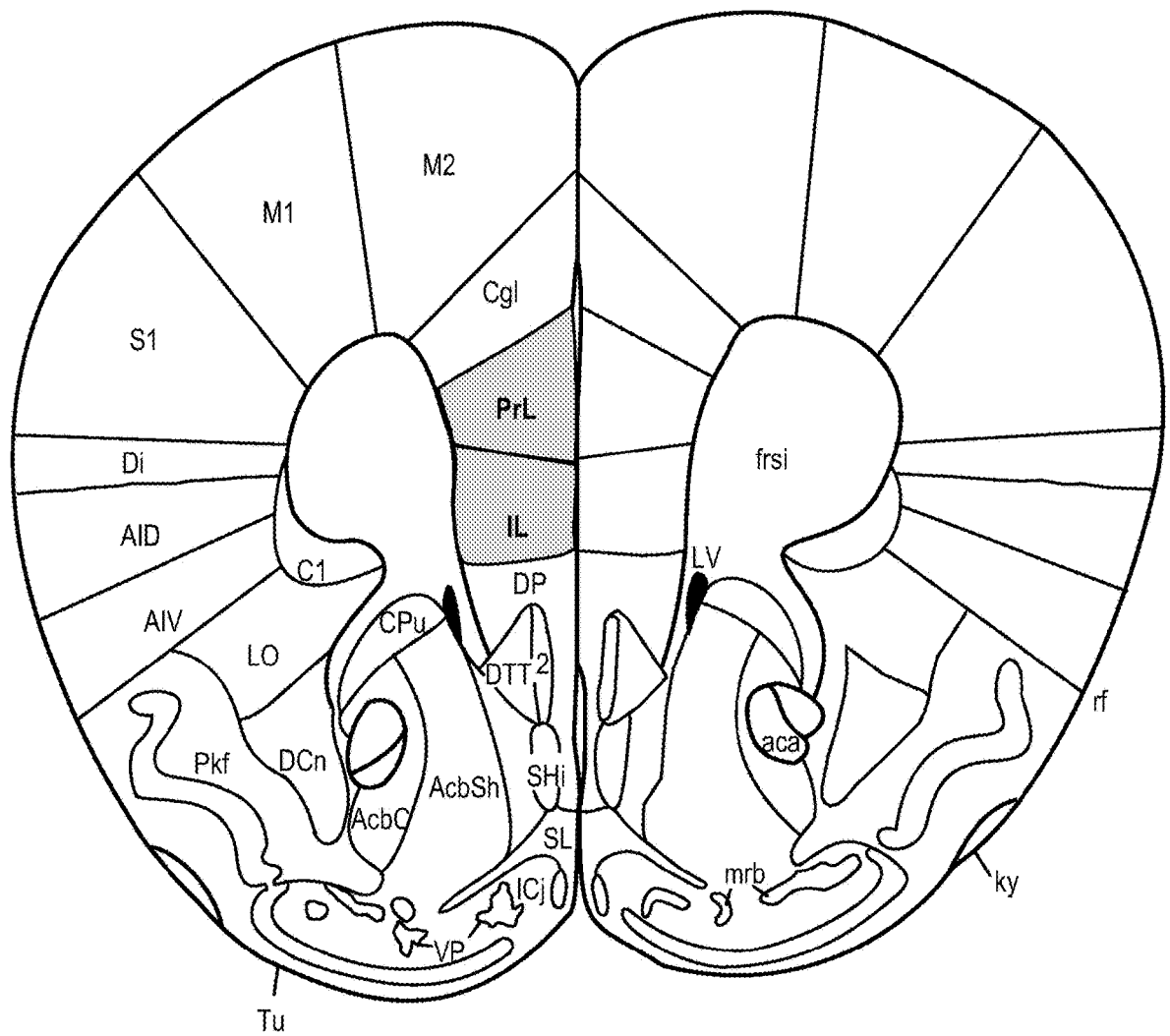

Furthermore, we performed PV and $GAD_{67}$ immunohistochemistry at adulthood (10 weeks) (FIG. 4D). PV-IR in the prelimbic (PrL), not IL (infralimbic), of mPFC in the offspring of poly(I:C)-treated mice was significantly lower than that of saline-treated group (FIG. 4D). PV-IR in the PrL (not IL) of the mPFC of the poly(I:C)+TPPU group was significantly higher than that in the poly(I:C)+control group (FIG. 4D).

Figure 4E:
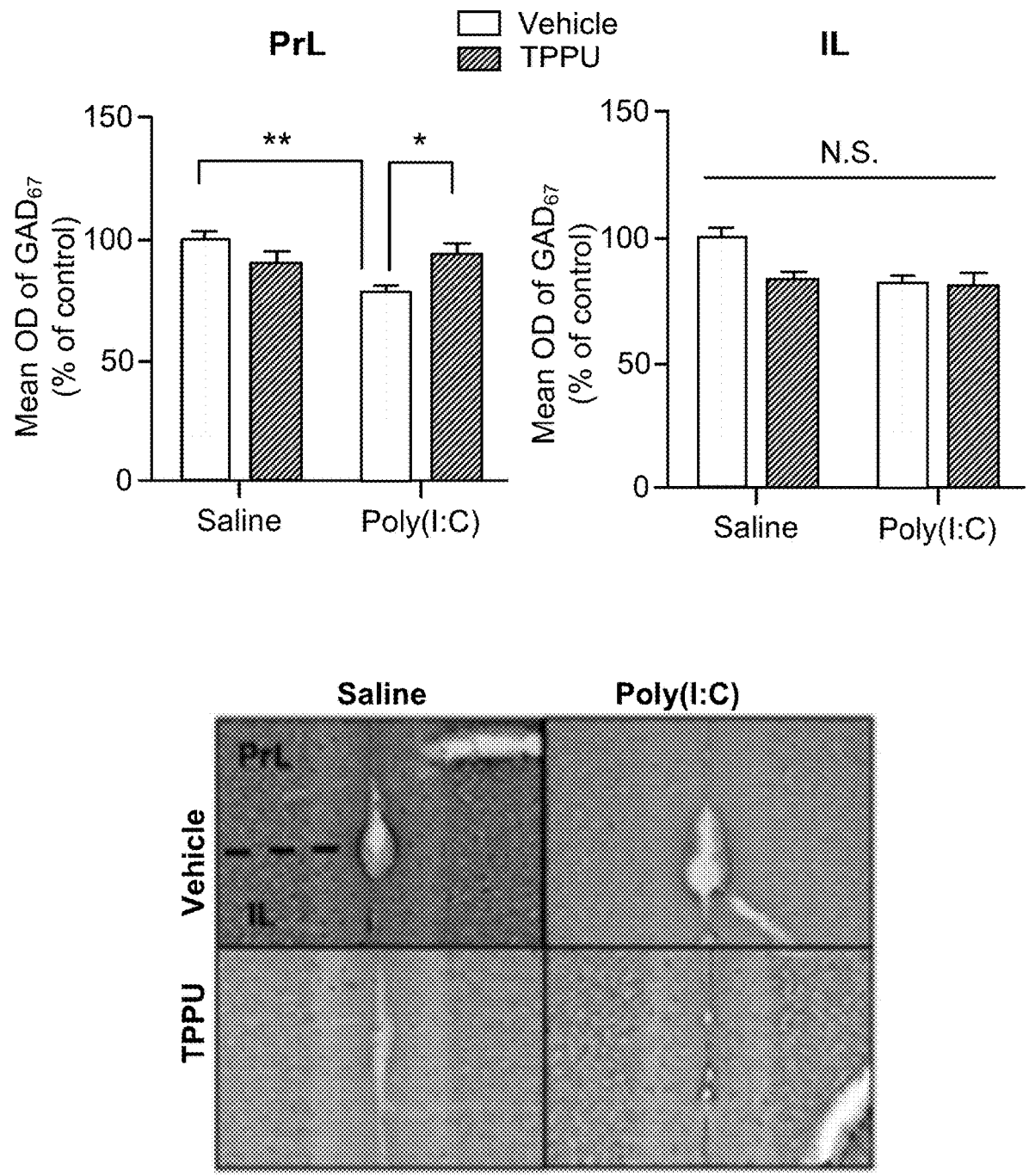

$GAD_{67}$, a key enzyme of y-aminobutyric acid (GABA) synthesis, is reported to be lower in the PFC from schizophrenia (40,41). $GAD_{67}$-IR in the PrL and IL of mPFC in the offspring of poly(I:C)-treated mice was significantly lower than that of saline-treated group (FIG. 4E). $GAD_{67}$-IR in the PrL (not IL) of the mPFC of the poly(I:C)+TPPU group was significantly higher than that in the poly(I:C)+control group (FIG. 4E). These findings suggest that TPPU in drinking water from P28 to P56 could prevent the reduction of PV- and $GAD_{67}$-IR in the PrL of the mPFC in adult offspring after MIA.

Role of sEH in ER stress in the mouse brain from juvenile offspring after MIA. It is reported that the sEH inhibitor attenuates activation of the endoplasmic reticulum (ER) (26,42-44). In this study, we examined the effects of TPPU on ER stress in the brain regions from juvenile offspring after MIA. We found increased levels of three key sensors in the ER stress signaling pathway, including PKR-like ER-resident kinase (PERK), inositol-requiring enzyme 1α (IRE1α), and activating transcription factor 6 (ATF6) (FIG. 5A and FIG. 5B). Levels of the associated downstream targets were elevated, suggesting full-scale activation of the ER stress pathway (26,43). Accordingly, phosphorylation of eukaryotic initiation factor 2 subunit a (eIF2a), mediated by phospho-PERK, was also increased. Phosphorylation of IRE1a led to a significant rise in total protein levels of spliced X-box binding protein 1 (Xbp1), as well as levels of the ER chaperone binding immunoglobulin protein (Bip). Increased phosphorylation of p38 and c-jun NH2-terminal kinase (JNK) ½ was also observed. Pharmacological inhibition by TPPU significantly attenuated ER stress in the brain regions from offspring after MIA (FIG. 5A and FIG. 5B).

Effect of TPPU in drinking water on cognitive and social interaction deficits and in juvenile offspring of prenatal mice exposed to poly(I:C). The pregnant mice were administrated with vehicle or TPPU (15 mg/L in drinking water) from E12 to 3-week old (P21). Subsequently, normal drinking water was given into all male offspring for additional 2 weeks (from 3 to 5-week old). Behavioral tests were performed at 4-5 week old (FIG. 6A). There were no differences of locomotion among the four groups (FIG. 6B). Two-way ANOVA analysis of NORT data in the training session revealed no significant interaction among four groups (FIG. 6C). In the retention session of NORT, two-way ANOVA analysis revealed a significant effect among four groups (FIG. 6C). Exploratory preference of poly(I:C)+water group was significantly lower than that of saline+water group or poly(I:C)+TPPU group (FIG. 6C).

Figure 6D:
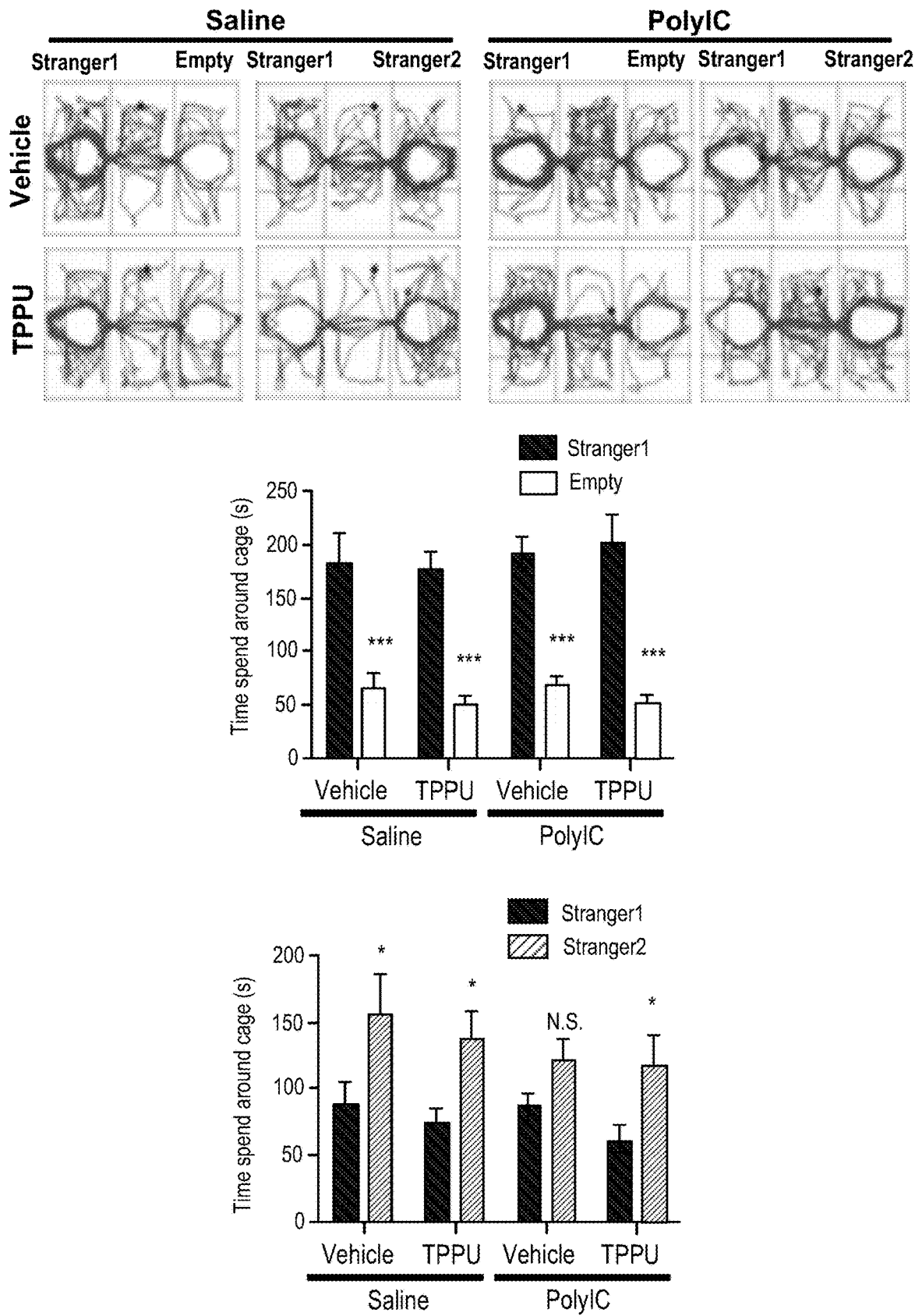
Figure 6E:
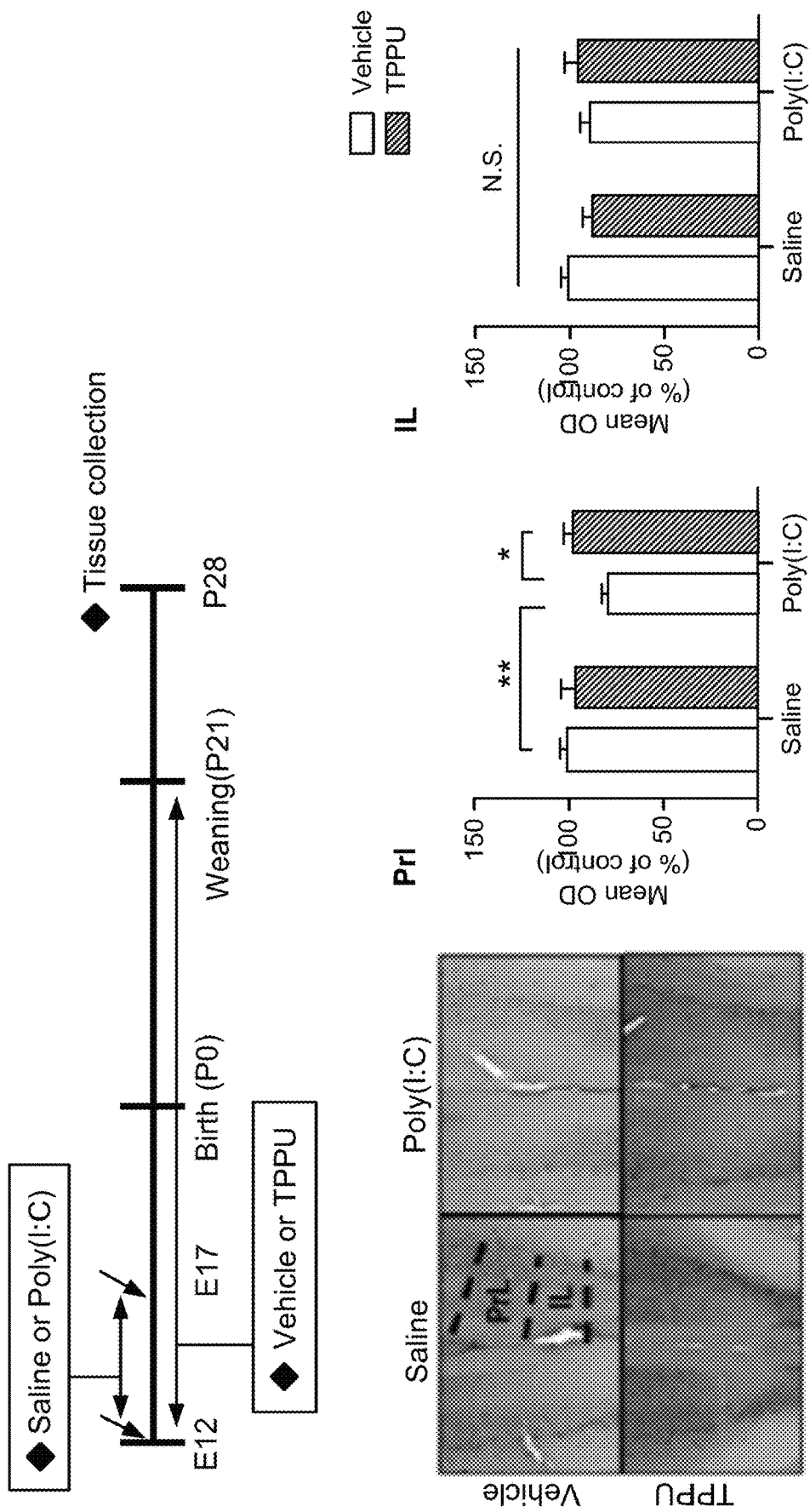

In the three-chamber social interaction test, TPPU in drinking water significantly improved social interaction deficits in juvenile offspring after MIA (FIG. 6D). Furthermore, TPPU in drinking water significantly attenuated reduction of PV-IR in the PrL in the mPFC of juvenile offspring after MIA (FIG. 6E).

Discussion

The present results demonstrate a key role of sEH in the pathogenesis of neurodevelopmental disorders in offspring after MIA. The major findings of the present study are as follows: First, expression of sEH protein in the PFC from juvenile offspring after MIA was higher than that of control group. Oxylipin analysis showed lower levels of EpFAs in the PFC from juvenile offspring after MIA, supporting higher levels of sEH in this region. Second, we found higher expression of EPHX2 mRNA in the neurospheres from iPSC of schizophrenia patients compared to healthy controls. In addition, we found higher expression of EPHX2 mRNA in the postmortem brain samples from ASD patients compared to control group. Third, TPPU in drinking water during the juvenile and adolescent stages of offspring after MIA prevented cognitive deficits and reduction of PV-IR and $GAD_{67}$-IR in the PrL of the mPFC at adulthood after MIA. Furthermore, TPPU in drinking water during the juvenile and adolescent stages of offspring after MIA significantly attenuated ER stress in the PFC from adult offspring after MIA. Finally, TPPU in drinking water in poly(I:C)-treated pregnant mice from pregnancy (E12) to weaning (P21) could prevent the onset of cognitive deficits and social interaction deficits, and reduction of PV-IR in the mPFC in juvenile offspring after MIA. Collectively, these findings suggest that sEH plays a key role in the pathogenesis of neurodevelopmental disorders such as schizophrenia and ASD, and that sEH inhibitors may prove to be promising prophylactic or therapeutic drugs for these disorders.

In this study, we found increased expression of sEH protein in the PFC of juvenile offspring after prenatal poly(I:C) exposure, although expression of sEH in other regions (striatum and hippocampus) remained the same. Thus, it seems that increases in the sEH in the PFC might play a role in the behavioral and biochemical abnormalities seen in juvenile offspring after MIA. Previously, we reported increased levels of sEH in the parietal cortex from schizophrenia patients compared to controls (22). In this study, we found higher levels of EPHX2 mRNA in the neurospheres from iPSC from schizophrenia patients and in the postmortem brain samples from ASD patients. These findings suggest that increased metabolism of EpFAs to the corresponding diols by increased sEH may play a role in the pathogenesis of schizophrenia and ASD, although further detailed studies on how prenatal poly(I:C) exposure induces abnormalities in the eicosanoid metabolism by sEH and behavioral abnormalities in juvenile and adulthood are needed.

Tissue levels of EpFAs were significantly lower in the PFC from juvenile offspring after MIA than those of control mice, supporting an increased activity of sEH in the PFC. The EpFAs such as 11,12-EpETrE, 8,9-EpETrE and 5,6-EpETrE are metabolized to its corresponding diol, dihydroxyeicosatrienoic acid (DiHETrE), by sEH (FIG. 1D). It is known that EETs such as EpETrE are important components of many intracellular signaling pathways in both cardiac and extracardiac tissues (45), and that EETs and some other EpFAs possess potent anti-inflammatory properties (46,47). Although the precise mechanisms underlying the relationship between EpETrEs and sEH in the PFC from juvenile offspring after MIA are currently unclear, it seems that increased metabolism of 10,12-EpETrE, 8,9-EpETrE and 5,6-EpETrE by increased levels of sEH in the PFC may be involved in behavioral abnormalities of offspring after MIA. By contrast, we found increased levels of EKODE in the hippocampus of juvenile offspring after MIA although levels of sEH were not altered. Although the reasons underlying this discrepancy are currently unknown, it seems that multiple pathways may contribute to formation and degradation of EKODE in the hippocampus. Further detailed study on the metabolism of EKODE in neurodevelopmental disorders is needed.

Previously, we reported cognitive deficits of juvenile offspring from poly(I:C)-treated mice (36-39). Since cognitive impairment is seen in adolescent and young adult with a high risk for psychosis (48,49), it seems that the juvenile offspring after MIA may be at the prodromal stage for psychosis (36-39). Furthermore, we found reduction of PV-IR in the mPFC at juvenile offspring after MIA, consistent with the previous study (37,39). It is well known that reduction of PV-IR in the PFC may contribute to the pathophysiology of schizophrenia (50). Furthermore, it is suggested that cognitive impairment may be due at least in part to lower expression of $GAD_{75}$ in the PFC from schizophrenia (41). Therefore, it is likely that reduction of PV-IR and $GAD_{67}$-IR in the PrL of mPFC may play a critical role in the cognitive deficits of offspring after MIA. Interestingly, we found that TPPU in drinking water during P28-P56 (similar to juvenile and adolescent stages in human) in offspring after neonatal poly(I:C) exposure could prevent cognitive deficits and reduction of PV- and $GAD_{67}$-IR at adulthood after MIA. Previously, we reported that AS2586114 (a sEH inhibitor) showed antipsychotic-like effects in phencyclidine-treated model of schizophrenia (51). Taken all together, it is likely that early intervention with sEH inhibitor (e.g., TPPU) during juvenile and adolescent stages might have prophylactic and therapeutic effects on abnormal behaviors in neurodevelopmental disorders, such as schizophrenia and ASD. Importantly, early intervention with sEH inhibitor (e.g., TPPU) in subjects with high-risk psychosis may prevent the transition to psychosis in young adulthood.

Pregnancy is a critical period of neurodevelopment during which pregnant females are also more vulnerable to stressful events. Epidemiological data demonstrated that maternal prenatal exposure to famine and its associated risk of the development of neurodevelopmental disorders in adult offspring are based on the Dutch famine of 1944-1945 or the Chinese famine of 1959-1960 (52-54). In this study, we found that TPPU in drinking water in poly(I:C)-treated pregnant mice from pregnancy (E12) to weaning (P21) could prevent the onset of cognitive and social interaction deficits in juvenile offspring after MIA. Given the role of neurodevelopmental stage in psychiatric disorders (55,56), supplementation with sEH inhibitor in pregnant mothers at ultra-high risk for psychosis may play an important role in preventing the onset of psychosis in offspring.

In conclusion, these findings suggest that increased sEH and subsequent decreased EpFAs might play a key role in the etiology of neurodevelopmental disorders in offspring after MIA. Therefore, sEH inhibitors appear to be new prophylactic or therapeutic drugs for MIA-related neurodevelopmental disorders such as schizophrenia and ASD.

REFERENCES

1. Brown A S, et al. (2004) Serologic evidence of prenatal influenza in the etiology of schizophrenia. *Arch Gen Psychiatry* 61:774-780.

2. Brown A S, Derkits E J (2010) Prenatal infection and schizophrenia: a review of epidemiologic and translational studies. *Am J Psychiatry* 167:261-280.
3. Estes M L, McAllister A K (2016) Maternal immune activation: Implication for neuropsychiatric disorders. *Science* 353:772-777.
4. Jiang H Y, et al. (2016) Maternal infection during pregnancy and risk of autism spectrum disorders: A systematic review and meta-analysis. *Brain Behav Immun* 58:165-172.
5. Careaga M, Murai T, Bauman M D (2017) Maternal immune activation and autism spectrum disorder: From rodents to nonhuman and human primates. *Biol Psychiatry* 81:391-401.
6. Zerbo O, Qian Y, Yoshida C, Fireman B H, Klein N P, Croen L A (2017) Association between influenza infection and vaccination during pregnancy and risk of autism spectrum disorder. *JAMA Pediatr* 171:e163609.
7. Brown A S, Meyer U (in press) Maternal immune activation and neuropsychiatric illness: A translational research perspective. *Am J Psychiatry* 2018 Sep. 17. doi: 10.1176/appi.ajp.2018.17121311.
8. Canetta S, et al. (2014) Elevated maternal C-reactive protein and increased risk of schizophrenia in a national birth cohort. *Am J Psychiatry* 171:960-968.
9. Brown A S, Sourander A, Hinkka-Yli-Salomäki S, McKeague I W, Sundvall J, Surcel H M (2014) Elevated maternal C-reactive protein and autism in a national birth cohort. *Mol Psychiatry* 19:259-264.
10. Zerbo O, et al. (2016) Maternal mid-pregnancy C-reactive protein and risk of autism spectrum disorders: the early markers for autism study. *Transl Psychiatry* 6:e783.
11. Kentner A C, et al. (in press) Maternal immune activation: reporting guidelines to improve the rigor, reproducibility, and transparency of the model. *Neuropsychopharmacology* 2018 Aug. 21. doi: 10.1038/s41386-018-0185-7.
12. Zuckerman L, Rehavi M, Nachman R, Weiner I (2003) Immune activation during pregnancy in rats leads to a post-pubertal emergence of disrupted latent inhibition, dopaminergic hyperfunction, and altered limbic morphology in the offspring: A novel neurodevelopmental model of schizophrenia. *Neuropsychopharmacology* 28:1778-1789.
13. Ozawa K, Hashimoto K, Kishimoto T, Shimizu E, Ishikawa H, Iyo M (2006) Immune activation during pregnancy in mice leads to dopaminergic hyperfunction and cognitive impairment in the offspring: A neurodevelopmental animal model of schizophrenia. *Biol Psychiatry* 59:546-554.
14. Patterson P H (2009) Immune involvement in schizophrenia and autism: Etiology, pathology and animal models. *Brain Res Rev* 204:313-321.
15. Meyer U (2014) Prenatal poly (I:C) exposure and other developmental immune activation models in rodent systems. *Biol Psychiatry* 75:307-315.
16. Gumusoglu S B, Stevens H E (in press) Maternal inflammation and neurodevelopmental programming: A review of preclinical outcomes and implications for translational psychiatry. *Biol Psychiatry* doi: 10.1016/j.biopsych.2018.08.008
17. Morisseau C, Hammock B D (2005) Epoxide hydrolases: mechanisms, inhibitor designs, and biological roles. *Annu Rev Pharmacol Toxicol* 45:311-333.
18. Imig J D, Hammock B D (2009) Soluble epoxide hydrolase as a therapeutic target for cardiovascular diseases. *Nat Rev Drug Discov* 8:794-805.
19. Morisseau C, Hammock B D (2013) Impact of soluble epoxide hydrolase and epoxyeicosanoids on human health. *Annu Rev Pharmacol Toxicol* 53:37-58.
20. Wagner K, Vito S, Inceoglu B, Hammock B D (2014) The role of long chain fatty acids and their epoxide metabolites in nociceptive signaling. *Prostaglandins Other Lipid Mediat* 113-115:2-12.
21. López-Vicario C, et al. (2015) Inhibition of soluble epoxide hydrolase modulates inflammation and autophagy in obese adipose tissue and liver: role for omega-3 epoxides. *Proc Natl Acad Sci USA* 112:536-541.
22. Ren Q, et al. (2016) Gene deficiency and pharmacological inhibition of soluble epoxide hydrolase confers resilience to repeated social defeat stress. *Proc Natl Acad Sci USA* 113:E1944-E1952.
23. Hashimoto K (2016) Soluble epoxide hydrolase: a new therapeutic target for depression. *Expert Opin Ther Targets* 20:1149-1151.
24. Wagner K M, McReynolds C B, Schmidt W K, Hammock B D (2017) Soluble epoxide hydrolase as a therapeutic target for pain, inflammatory and neurodegenerative diseases. *Pharmacol Ther* 180:62-76.
25. Swardfager W, et al. (2018) Metabolic/inflammatory/vascular comorbidity in psychiatric disorders; soluble epoxide hydrolase (sEH) as a possible new target. *Neurosci Biobehav Rev* 87:56-66.
26. Ren Q, et al. (2018) Soluble epoxide hydrolase plays a key role in the pathogenesis of Parkinson's disease. *Proc Natl Acad Sci USA* 115:E5815-E5823.
27. Wang W, et al. (2018) Lipidomic profiling reveals soluble epoxide hydrolase as a therapeutic target of obesity-induced colonic inflammation. *Proc Natl Acad Sci USA* 115:5283-5288.
28. Jonas R K, Montojo C A, Bearden C E (2014) The 22q11.2 deletion syndrome as a window into complex neuropsychiatric disorders over the lifespan. *Biol Psychiatry* 75:351-360.
29. Schneider M, et al. (2014) Psychiatric disorders from childhood to adulthood in 22q11.2 deletion syndrome: results from the International Consortium on Brain and Behavior in 22q11.2 Deletion Syndrome. *Am J Psychiatry* 171:627-639.
30. Rose T E, et al. (2010) 1-Aryl-3-(1-acylpiperidin-4-yl) urea inhibitors of human and murine soluble epoxide hydrolase: structure-activity relationships, pharmacokinetics, and reduction of inflammatory pain. *J Med Chem* 53(19):7067-7075.
31. Ostermann A I, et al. (2015) Oral treatment of rodents with soluble epoxide hydrolase inhibitor 1-trifluoromethoxyphenyl-3-(1-propionylpiperidin-4-yl)urea (TPPU): bioavailability, resulting drug levels and modulation of oxylipin pattern. *Prostaglandins Other Lipid Mediat* 121(Pt A):131-137.
32. Balan S, Toyoshima M, Yoshikawa T (2018) Contribution of induced pluripotent stem cell technologies to the understanding of cellular phenotypes in schizophrenia. *Neurobiol Dis* 2018 May 3. doi: 10.1016/j.nbd.2018.04.021.
33. Toyoshima M, et al. (2016) Analysis of induced pluripotent stem cells carrying 22q11.2 deletion. *Transl Psychiatry* 6:e934.
34. Balan S, et al. (2014) Exon resequencing of H3K9 methyltransferase complex genes, EHMT1, EHTM2 and WIZ, in Japanese autism subjects. *Mol Autism* 5:49.
35. Elvevåg B, Goldberg T E (2000) Cognitive impairment in schizophrenia is the core of the disorder. *Crit Rev Neurobiol* 14:1-21.

36. Fujita Y, Ishima T, Hashimoto K (2016) Supplementation with D-serine prevents the onset of cognitive deficits in adult offspring after maternal immune activation. *Sci Rep* 6:37261.

37. Han M, et al (2016) Intake of 7,8-dihydroxyflavone during juvenile and adolescent stages prevents onset of psychosis in adult offspring after maternal immune activation. *Sci Rep* 6:36087.

38. Han M, Zhang J C, Huang X F, Hashimoto K (2017) Intake of 7,8-dihydroxyflavone from pregnancy to weaning prevents cognitive deficits in adult offspring after maternal immune activation. *Eur Arch Psychiatry Clin Neurosci* 267:479-483.

39. Matsuura A, et al. (2018) Dietary glucoraphanin prevents the onset of psychosis in the adult offspring after maternal immune activation. *Sci Rep* 8:2158.

40. Guidotti A, et al. (2000) Decrease in reelin and glutamic acid decarboxylase67 ($GAD_{67}$) expression in schizophrenia and bipolar disorder: a postmortem brain study. *Arch Gen Psychiatry* 57:1061-1069.

41. Kimoto S, Bazmi H H, Lewis D A (2014) Lower expression of glutamic acid decarboxylase 67 in the prefrontal cortex in schizophrenia: contribution of altered regulation by Zif268. *Am J Psychiatry* 171:969-978.

42. Bettaieb A, et al. (2013) Soluble epoxide hydrolase deficiency or inhibition attenuates diet-induced endoplasmic reticulum stress in liver and adipose tissue. *J Biol Chem* 288:14189-14199.

43. Inceoglu B, et al. (2015) Endoplasmic reticulum stress in the peripheral nervous system is a significant driver of neuropathic pain. *Proc Natl Acad Sci USA* 112:9082-9087.

44. Inceoglu B, Bettaieb A, Haj F G, Gomes A V, Hammock B D (2017) Modulation of mitochondrial dysfunction and endoplasmic reticulum stress are key mechanisms for the wide-ranging actions of epoxy fatty acids and soluble epoxide hydrolase inhibitors. *Prostaglandins Other Lipid Mediat* 133:68-78.

45. Seubert J M, Zeldin D C, Nithipatikom K, Gross G J (2007) Role of epoxyeicosatrienoic acids in protecting the myocardium following ischemia/reperfusion injury. *Prostaglandins Other Lipid Mediat* 82:50-59.

46. Campbell W B (2000) New role for epoxyeicosatrienoic acids as anti-inflammatory mediators. *Trends Pharmacol Sci* 21:125-127.

47. Wagner K M, McReynolds C B, Schmidt W K, Hammock B D (2017) Soluble epoxide hydrolase as a therapeutic target for pain, inflammatory and neurodegenerative diseases. *Pharmacol Ther* 180:62-76.

48. Fusar-Poli P, et al. (2011) Cognitive functioning in prodromal psychosis: a meta-analysis. *Arch Gen Psychiatry* 69:562-571.

49. Gur R C, et al. (2014) Neurocognitive growth charting in psychosis spectrum youths. *JAMA Psychiatry* 71:366-374.

50. Lewis D A, Curley A A, Glausier J R, Volk D W (2012) Cortical parvalbumin interneurons and cognitive dysfunction in schizophrenia. *Trends Neurosci* 35:57-67.

51. Ma M, Ren Q, Fujita Y, Ishima T, Zhang J C, Hashimoto K (2013) Effects of AS2586114, a soluble epoxide hydrolase inhibitor, on hyperlocomotion and prepulse inhibition deficits in mice after administration of phencyclidine. *Pharmacol Biochem Behav* 110:98-103.

52. Susser E S, Lin S P (1992) Schizophrenia after prenatal exposure to the Dutch hunger winter of 1944-1945. *Arch Gen Psychiatry* 49:983-988.

53. St Clair D, Xu M, Wang P, Yu Y, Fang Y, Zhang F, Zheng X, Gu N, Feng G, Sham P, He L (2005) Rates of adult schizophrenia following prenatal exposure to the Chinese famine of 1959-1961. *JAMA* 294:557-562.

54. Susser E, St Clair D (2013) Prenatal famine and adult mental illness: interpreting concordant and discordant results from the Dutch and Chinese Famines. *Soc Sci Med* 97:325-330.

55. Fatemi S H, Folsom T D (2009) The neurodevelopmental hypothesis of schizophrenia, revisited. *Schizophr Bull* 35:528-548.

56. Hantsoo L, Kornfield S, Anguera A C, Epperson N (in press) Inflammation: A proposed intermediary between maternal stress and offspring neuropsychiatric risk. *Biol Psychiatry* 2018 Sep. 5. doi.org/10.1016/j.biopsych.2018.08.018.

57. Yang J, Schmelzer K, Georgi K, Hammock B D (2009) Quantitative profiling method for oxylipin metabolome by liquid chromatography electrospray ionization tandem mass spectrometry. *Anal Chem* 81:8085-8093.

58. Hashimoto K, Fujita Y, Shimizu E, Iyo M (2005) Phencyclidine-induced cognitive deficits in mice are improved by subsequent subchronic administration of clozapine, but not haloperidol. *Eur J Pharmacol* 519:114-117.

59. Shirai Y, et al. (2015) Dietary intake of sulforaphane-rich broccoli sprout extracts during juvenile and adolescence can prevent phencyclidine-induced cognitive deficits at adulthood. *PLoS One* 10:e0127244.

60. Yang C, Han M, Zhang J C, Ren Q, Hashimoto K (2016) Loss of parvalbumin-immunoreactivity in mouse brain regions after repeated intermittent administration of esketamine, but not R-ketamine. *Psychiatry Res* 239:281-283.

61. Takahashi K, et al. (2007) Induction of pluripotent stem cells from adult human fibroblasts by defined factors. *Cell* 131:861-872.

62. Imaizumi K, et al. (2015) Controlling the regional identity of hPSC-derived neurons to uncover neuronal subtype specificity of neurological disease phenotypes. *Stem Cell Reports* 5:1010-1022

63. Matsumoto T, et al. (2016) Functional neurons generated from T cell-derived induced pluripotent stem cells for neurological disease modeling. *Stem Cell Reports* 6:422-435.

Example 2

Maternal Glyphosate Exposure Causes Autism-Like Behaviors in Offspring Through Increased Expression of Soluble Epoxide Hydrolase The purpose of this study was to examine the role of sEH in the pathogenesis of ASD in offspring after maternal glyphosate exposure. First, we examined whether maternal glyphosate exposure causes ASD-like behavioral abnormalities in juvenile offspring. Second, we examined whether expression of sEH is altered in the brain regions of juvenile offspring after maternal glyphosate exposure. Furthermore, we performed oxylipin analysis of blood and brain regions from juvenile offspring. Moreover, we measured levels of N-methyl-D-aspartate receptor (NMDAR)-related amino acids in the blood and brain from juvenile offspring since NMDAR-related amino acids were altered in patients with ASD (32-36). Third, we performed 16S rRNA analysis and measurement of short-chain fatty acids of fecal samples in juvenile offspring after maternal glyphosate exposure since abnormal composition of gut microbiota is shown in patients with ASD (36-40). Finally, we examined whether treatment with TPPU (1-trifluoromethoxyphenyl-3-(1-propionylpiperidin-4-yl)urea)(41,42), a potent sEH inhibitor, into pregnant mice from pregnancy to weaning could prevent behavioral abnormalities in juvenile offspring after maternal glyphosate exposure.

Materials and Methods

Animals and animal care. Pregnant ddY mice (embryo at the 5th day (E5), 9-10 weeks old) were purchased from Japan SLC Inc. (Hamamatsu, Shizuoka, Japan). Pregnant mice in each clear polycarbonate cage (22.5×33.8×14.0 cm) one by one were housed under controlled temperatures and 12 hour light/dark cycles (lights on between 07:00-19:00 h), with ad libitum food (CE-2; CLEA Japan, Inc., Tokyo, Japan) and water. The protocol was approved by the Chiba University Institutional Animal Care and Use Committee. This study was carried out in strict accordance with the recommendations in the Guide for the Care and Use of Laboratory Animals of the National Institutes of Health, USA.

Treatment of glyphosate in drinking water into pregnant mice. Previous studies used drinking water containing 0.38% glyphosate (1% Roundup®) during pregnancy and lactation, equivalent to 50 mg/kg/day of glyphosate (1,2). This does correspond with 1/20 of the glyphosate no-observed-adverse-effect level, as described previously (3). Therefore, water or glyphosate [or 0.1, 0.25, 0.50, 0.75, 1.0% Roundup®, Nissan Chemical Corporation, Tokyo, Japan] were given to the pregnant mice from E5 to P21 (weaning). The male offspring were separated from their mothers at weaning (P21), and mice were caged each three-five in the groups in clear polycarbonate cage (22.5× 33.8×14.0 cm). Mice were housed under controlled temperatures and 12 hour light/dark cycles (lights on between 07:00-19:00 h), with ad libitum food and water.

Measurement of glyphosate in the blood. Water or 0.095% glyphosate was given to pregnant mice from E5 to P21, as described above. At weaning (P21), mothers and male offspring mice were deeply anesthetized with isoflurane and plasma was collected. The plasma samples were stored at −80° C. before assay. Measurement of glyphosate in the plasma was performed using LC/MS/MS at UC Davis.

The 40 μL of internal standard (2 μg/mL of glyphosate-2-$^{13}$C solution in methanol) and 40 μL of methanol were added to 20 μL of plasma. The spiked sample was vortexed for 5 minutes and then centrifuged at 16,100 g/min for another 5 minutes. The supernatants were transferred for the followed LC/MS/MS measurement, which uses Waters Acquity UPLC system (Waters, Milford, MA) interfaced with a QTRAP 6500+ mass spectrometer (Sciex, Redwood City, CA) using electrospray source. The separation was achieved on a Waters Acquity BEH C18 50×2.1 mm 1.7 μm column with mobile phases of water with 0.1% of formic acid as mobile phase A and acetonitrile with 0.1% of formic acid as mobile phase B. The gradient was shown in Table 10. All the parameters on the mass spectrometer were optimized with pure standards of glyphosate and glyphosate-2-[13]C (purchased from Millipore Sigma, Burlington MA) under positive MRM mode. The detailed parameters were given in Table 11.

TABLE 10

A gradient of liquid chromatography for the separation.

| Time | Flow Rate | % A | % B | Curve |
|---|---|---|---|---|
| Initial | 0.35 | 75 | 25 | Initial |
| 0.5 | 0.35 | 75 | 25 | 6 |
| 2 | 0.35 | 10 | 90 | 6 |
| 3 | 0.35 | 10 | 90 | 6 |
| 3.1 | 0.35 | 75 | 25 | 6 |
| 5 | 0.35 | 75 | 25 | 6 |

TABLE 11

The optimization of the mass transitions of mass spectrometer for glyphosate.

| Compounds | Q1 | Q3 | DP | CE | CXP |
|---|---|---|---|---|---|
| Glyphosate | 169.9 | 87.9 | 60 | 11 | 10 |
| Glyphosate_qualify | 169.9 | 60 | 60 | 21 | 8 |
| GHlyphosate-2-[13]C | 170.9 | 88.9 | 60 | 14 | 15 |
| Glyphosate-2-$^{13}$C quality | 170.9 | 61 | 60 | 28 | 9 |

Collection of blood and brain samples and oxylipin analysis. Water or 0.095% glyphosate was given to pregnant mice from E5 to P21, as described above. The male offspring were separated from their mothers at weaning (P21). At juvenile (P28) stage, mice were deeply anesthetized with isoflurane and plasma was collected. Subsequently, brains were removed from the skulls. For Western blot analysis, brain regions such as prefrontal cortex (PFC), hippocampus, and striatum, were dissected from brain on ice. The samples were stored at −80° C. before assay. For oxylipin analysis, plasma was collected after isoflurane anesthesia at juvenile (P28) stage. Subsequently, PFC, hippocampus, and striatum were dissected from brain on ice, and the samples were stored at −80° C. before assay. Measurement of eicosanoids in the plasma and brain regions was performed at UC Davis using the previous method (4).

Western blot analysis. Western blot analysis was performed as reported previously (5-7). Basically, the tissue samples were homogenized in Laemmli lysis buffer. 50 μg of protein were measured using the DC protein assay kit (Bio-Rad), and incubated for 5 min at 95° C., with an equal volume of 125 mM Tris-HCl, pH6.8, 20% glycerol, 0.1% bromophenol blue, 10% β-mercaptoethanol, 4% sodium dodecyl sulfate, and subjected to sodium dodecyl sulfate polyacrylamide gel electrophoresis, using 7.5% or AnyKD mini-gels (Mini-PROTEAN® TGX™ Precast Gel; Bio-Rad, CA, USA). Proteins were transferred onto polyvinylidenedifluoride (PVDF) membranes using a Trans Blot Mini Cell (Bio-Rad). For immunodetection, the blots were blocked with 2% BSA in TBST (TBS+0.1% Tween-20) for 1 h at room temperature (RT), and kept with primary sEH antibody (prepared at UC Davis) overnight at 4° C. The next day, blots were washed three times in TBST and incubated with horseradish peroxidase conjugated anti-rabbit or anti-mouse antibody 1 hour, at RT. After final three washes with TBST, bands were detected using enhanced chemiluminescence (ECL) prime Western Blotting Detection system (GE Healthcare Bioscience). Images were captured with a ChemDoc imaging system (Bio-Rad), and the immunoreactive bands were analysis by Image Lab software.

Gene expression analysis by quantitative real-time PCR. At juvenile (P28) stage, mice were sacrificed, and their brains were removed for measurement of gene expression of Ephx2 mRNA. Brain regions such as PFC, hippocampus, and striatum were dissected from brain on ice. A quantitative RT-PCR system (Step One Plus, Thermo Fisher Scientific, Yokohama, Japan) was used to measure mRNAs. The specific mRNA transcripts were quantified by TaqManGene Expression assays (Thermo Fisher Scientific, Yokohama, Japan). Expression levels of Ephx2 (Mm01313813_m1) was measured in brain tissue. Total RNA was extracted by use of an RNeasy Mini Kit (Qiagen, Hilden, Germany). The purity of total RNA was assessed by Biophotometer plus (Eppendorf, Hamburg, Germany). The RNA samples were used in the first strand cDNA synthesis with High Capacity cDNA Reverse Transcription Kit (#4368813 Thermo Fisher Scientific, Yokohama, Japan). All samples were tested in triplicate and average values were used for quantification. The average values were normalized to Vic-labeled Actb mRNA (Cat #4352341E: pre-developed TaqMan Assay Reagents, Thermo Fisher Scientific, Yokohama, Japan).

Treatment of TPPU. TPPU was dissolved in polyethylene glycol 400 (PEG 400: Tokyo Chemical Industry Co., Ltd, Tokyo, Japan). TPPU (3 mg/kg/day) or vehicle (5 ml/kg, PEG 400) was administered orally in the pregnant mice from E5 to P21. Behavioral tests of offspring were performed during juvenile stage (P28-P35) after maternal glyphosate exposure (FIG. 1A).

Behavioral analysis. Locomotion, the novel object recognition test (NORT), and prepulse inhibition (PPI) test were performed as reported previously (7-13).

Locomotor Activity: Both horizontal and rearing activity were monitored by an infrared ray passive sensor system (SCANET-SV10, Melquest Ltd., Toyama, Japan), and activity was integrated every minute. Individual mice were placed in activity chambers and allowed 1 hour of free exploration as spontaneous activity.

Novel Object Recognition Test (NORT): Mice were habituated for 10 minutes in the test box for 3 straight days. At 4th day, two objects (differing in shape and color but of similar size) were placed in the box 35.5 cm apart (symmetrically), and each animal was allowed to explore in the box for 5 minutes. The animals were considered to be exploring the object when the head of the animal was both facing and within 2.54 cm of the object or when any part of the body, except for the tail was touching the object. The time that mice spent exploring each object was recorded. After training, mice were immediately returned to their home cages, and the box and objects were cleaned with 75% ethanol, to avoid any possible instinctive odorant cues. Retention tests were carried out at one-day intervals, following the respective training. During the retention test, each mouse was reintroduced into their original test box, and one of the training objects was replaced by a novel object. The mice were then allowed to explore freely for 5 minutes, and the time spent exploring each object was recorded. Throughout the experiments, the objects were counter-balanced, in terms of their physical complexity and emotional neutrality. A preference index, that is, the ratio of time spent exploring either of the two objects (training session) or the novel object (retention test session) over the total time spent exploring both objects, was used.

PPI: The offspring mice were tested for their acoustic startle reactivity (ASR) in a startle chamber (SR-LAB; San Diego Instruments, San Diego, CA, USA) using the standard methods described previously (9,10). The test sessions were begun after an initial 10-min acclimation period in the chamber. The mice were subjected to one of six trials: (1) pulse alone, as a 40 ms broadband burst; a pulse (40 ms broadband burst) preceded by 100 ms with a 20 ms prepulse that was (2) 4 dB, (3) 8 dB, (4) 12 dB, or (5) 16 dB over background (65 dB); and (6) background only (no stimulus). The amount of prepulse inhibition (PPI) was expressed as the percentage decrease in the amplitude of the startle reactivity caused by presentation of the prepulse (% PPI). The PPI test lasted 20 min in total.

Three-chamber Social Interaction Test: The three-chamber social interaction test was performed to investigate sociability and preference for social novelty in mice, as reported previously (7). The apparatus consisted of a rectangular, three-chambered box and a lid with a video camera (BrainScience Idea, Co., Ltd, Osaka, Japan). Each chamber (20 cm×40 cm×20 cm) was divided by a clear plastic wall with a small square opening (5 cm×8 cm). First, each subject mouse was placed in the box and allowed to explore for 10 min to habituate the environment. During the session, an empty wire cage (10 cm in diameter, 17.5 cm in height, with vertical bars 0.3 cm apart) was located in the center of left and right chamber. Next, an unfamiliar ddY male mouse (stranger 1) that had no prior contact with the subject mouse was put into a wire cage that was placed into one of the side chambers. To assess sociability, the subject mouse was allowed to explore the box for an additional 10-min session. Finally, to evaluate social preference for a new stranger, a second stranger male mouse (stranger 2) was placed into the wire cage that had been empty during the first 10-min session (social novelty preference test). Thus, the subject mouse had a choice between the first, non-familiar mouse (stranger 1) and the novel unfamiliar mouse (stranger 2). The time spent in each chamber and the time spent around each cage was recorded on video.

Grooming test: The test was performed as previously described (14,15). Each mouse was put individually in a clean standard mouse cage and allowed to acclimate for 10 min. A video camera (C920r HD Pro, Japan) was set up two meters in front of the cage to record the mice behavior for the next 10 min, following the habituation time. After the experiment, the cumulative time spent in self-grooming was counted by an experimenter through watching these videos. A stopwatch was used for scoring cumulative time spent grooming during the 10 min test session.

PV-immunohistochemistry. Immunohistochemistry of PV was performed as reported previously (7,13,16,17). Mice were anesthetized with 5% isoflurane and sodium pentobarbital (50 mg/kg), and perfused transcardially with 10 mL of saline, followed by 30 mL of ice-cold 4% paraformaldehyde in 0.1M phosphate buffer (pH 7.4). Brains were removed from the skulls and post fixed overnight at 4° C. in the same fixative. For the immunohistochemical analysis, 50 μm-thick serial, coronal sections of brain tissue were cut in ice-cold 0.01M phosphate buffered saline (pH 7.4) using a vibrating blade microtome (VT1000s, Leica Microsystems, Tokyo, Japan). Mounted on gelatinized slides brain sections were washed by PBS for three times and then blocked in PBS containing 0.3% Triton X-100 (PBST) and 3% normal serum for 1 h at room temperature. The samples were then incubated for 24 h at 4° C. with mouse polyclonal anti-parvalbumin (PV) antibody (1:100, abcam, ab11427) in PBST with 1% normal serum. After that the sections were washed three times in PBS and then incubated for 2 h in room temperature with Alexa Fluor 488 Polyclonal Antibody (1:1000, Invitrogen, A11094). Then, sections were washed three times in PBS containing 0.1% Triton X-100 and cover slipped under VECTASHIELD (Vector Laboratories, Inc. Burlingame, CA, USA). The PV-immunofluorescent-positive cells in the inflalimbic (IL) and prelimbic (PrL) regions (0.05 mm$^2$) of mPFC was analyzed using a fluorescence microscope with a CCD camera (Olympus IX70, Tokyo, Japan) and the SCION IMAGE software package. Images of sections within mPFC region were captured using a CFI PLan APO Lambda 40× objective with a Keyence BZ-X710 microscope (Keyence Corporation, Osaka, Japan).

Measurement of amino acids. On P28, mice were deeply anesthetized with isoflurane and plasma was collected. Subsequently, prefrontal cortex (PFC), hippocampus and striatum were quickly dissected on ice from whole brain. The dissected tissues were weighed and stored at −80° C. until assayed. Levels of amino acids (glutamate, glutamine, glycine, L-serine, D-serine, GABA) were measured using high performance liquid chromatography system (Shimadzu Corporation, Kyoto, Japan), as reported previously (12,18,19).

16S rRNA analysis and measurement of short-chain fluty acids of fecal samples. On P28, we collected fresh fecal samples from each mouse at around 10:00 in order to avoid circadian effects on the microbiome. The fecal samples were put into a sterilized screw cap microtube immediately after defecation, and these samples were stored at −80° C. until use. DNA extraction from mouse feces and 16S rRNA analysis of fecal samples were performed by MyMetagenome Co, Ltd. (Tokyo, Japan), as reported previously (20,21).

Measurement of short-chain fatty acids—acetic acid, propionic acid, butyric acid, and valeric acid—in fecal samples was performed by the TechnoSuruga Laboratory, Co., Ltd. (Shizuoka, Japan).

Statistical analysis. Analysis of the data was performed using GraphPad Prism (La Jolla, CA). Comparisons between two groups were performed using Student t-test. The PPI data were analyzed using multivariable analysis of variance (MANOVA). Comparisons among four groups were performed using the repeated measure two-way analysis of variance (ANOVA) or two-way ANOVA, followed by Fisher's LSD test. The P-values of less than 0.05 were considered statistically significant.

Results

Figures 7A, 7B, 7C:
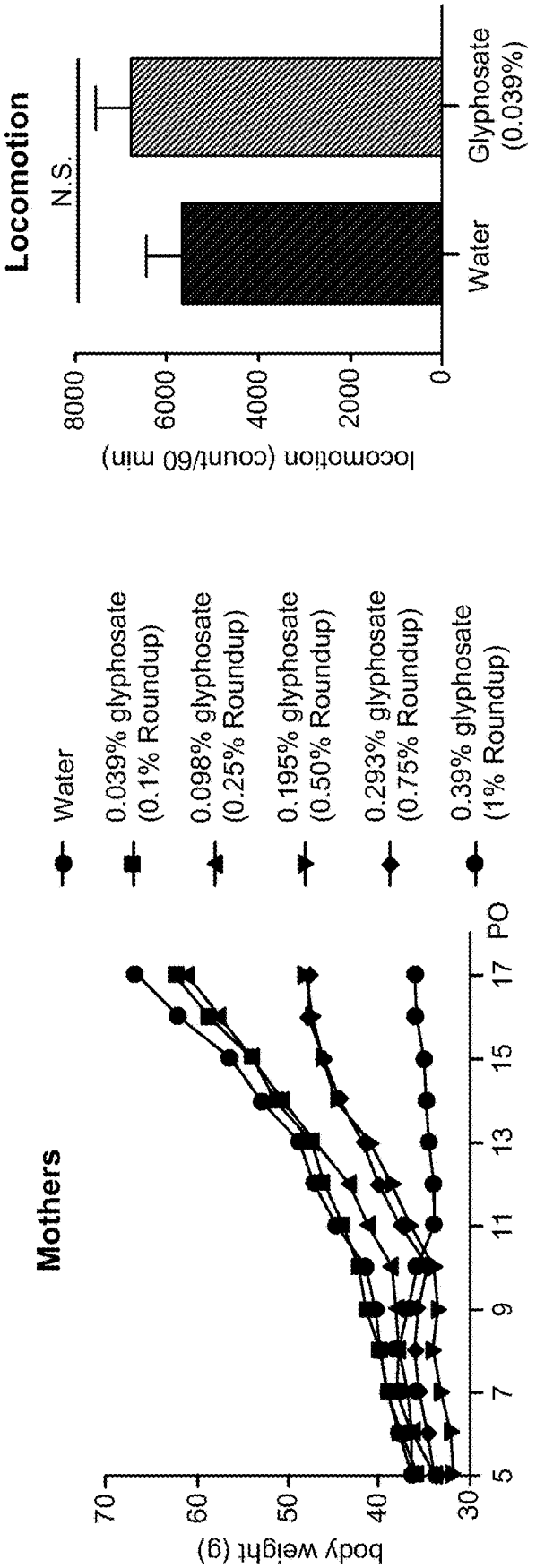

General and behavioral data of mother and juvenile offspring after maternal glyphosate exposure. First, we examined whether maternal glyphosate exposure could affect the general and behavioral outcomes in offspring (FIG. 7A). Water or glyphosate [0.038% (or 0.1% Roundup™)-0.38% (or 1.0% Roundup®)] were given to pregnant mice from E5 to P21 (weaning). The mortality of pregnant mice of highest concentration (0.38%) was 100% although the mortality of lower concentrations (0.038% and 0.095%) was 0% (Table 12). Body weight of pregnant mice was increased gradually after maternal glyphosate (0.038%-0.285%) exposure, whereas body weight of pregnant mice treated with high concentration (0.38%) was not increased (FIG. 7B). Although mortality of offspring in the 0.038% glyphosate group was 0%, juvenile offspring after maternal 0.038% glyphosate exposure did not show any behavioral abnormality such as locomotion, social interaction deficits in three chamber test and depression-like phenotype in the forced swimming test (FIGS. 7C-7E, and Table 12). In contrast, we found social interaction deficits in juvenile offspring after maternal 0.095% glyphosate exposure. Therefore, we used 0.095% glyphosate in the subsequent experiments. This concentration corresponded with 1/80 of the glyphosate no-observed-adverse-effect level, as reported previously (43).

TABLE 12

General and behavioral data of mother and juvenile offspring after maternal glyphosate exposure

| Concentration | Number of mothers used | Alive number of mothers on P0 | Maternal mortality | Number of offspring born | Alive number of offspring on P21 | Offspring mortality | Behavioral abnormality |
| --- | --- | --- | --- | --- | --- | --- | --- |
| 0.38% glyphosate (1% Roundup ®) | 4 | 0 | 100% | 0 | 0 | — | — |
| 0.285% glyphosate (0.75% Roundup ®) | 4 | 3 | 25% | 32 | 4 | 87.5% | — |
| 0.19% glyphosate (0.50% Roundup ®) | 5 | 4 | 20% | 43 | 2 | 95.3% | — |
| 0.095% glyphosate (0.25% Roundup ®) | 3 | 3 | 0% | 30 | 24 | 20% | observed |
| 0.038% glyphosate (0.1% Roundup ®) | 3 | 3 | 0% | 33 | 33 | 0% | Not observed |

Figure 8E:
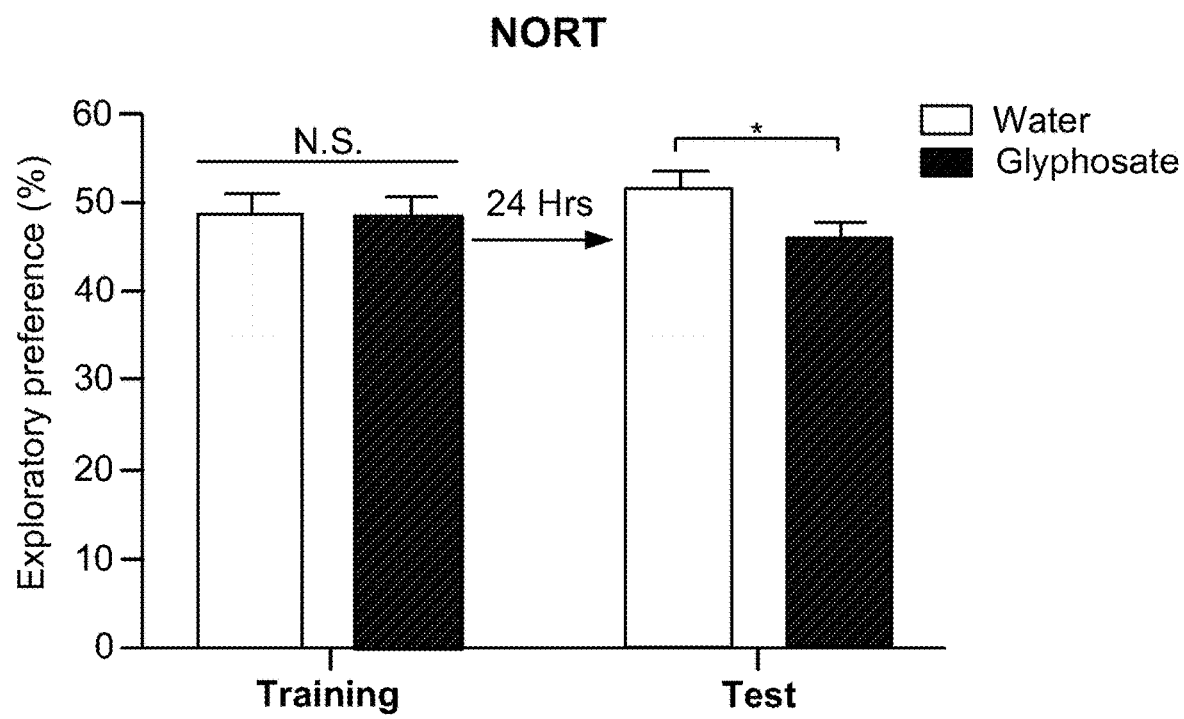
Figure 8F:
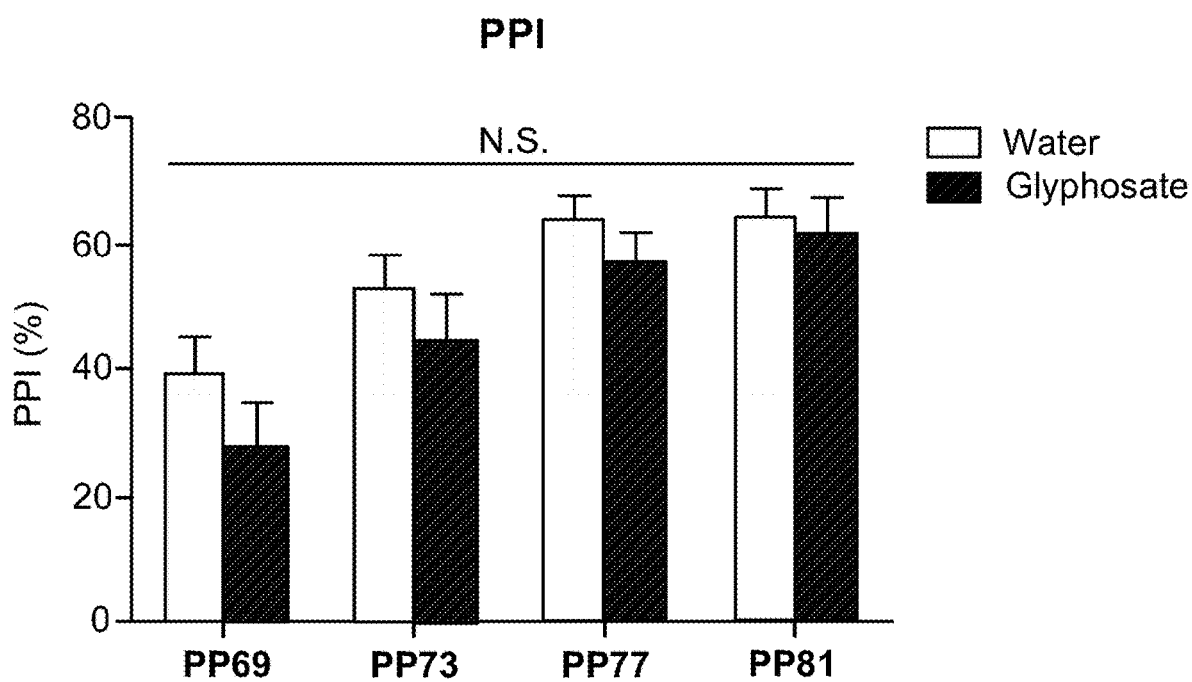
Figure 8G:
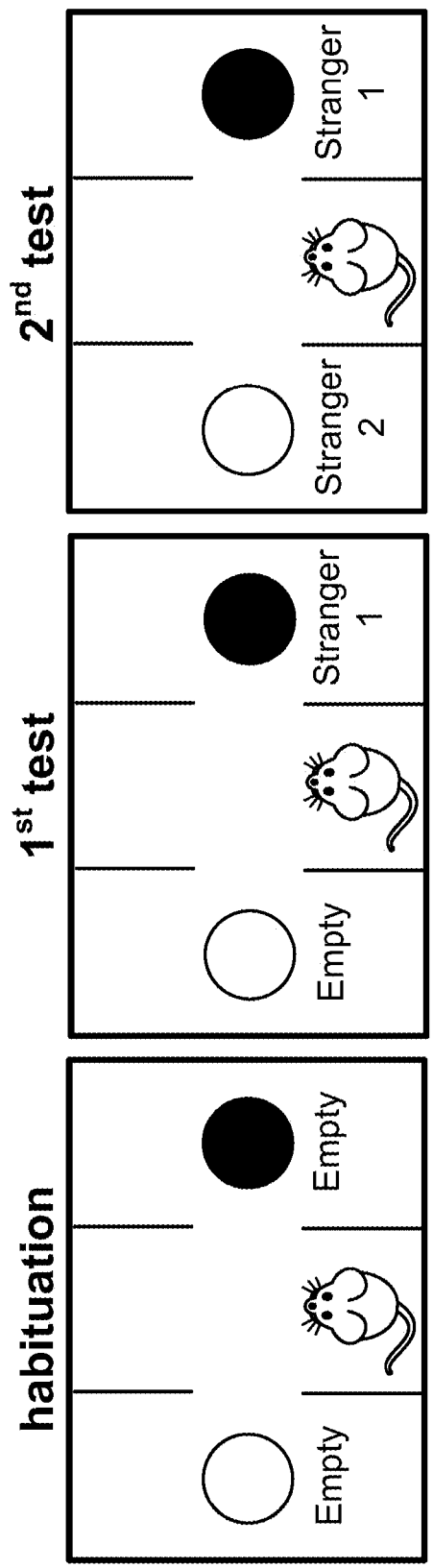
Figure 8G:
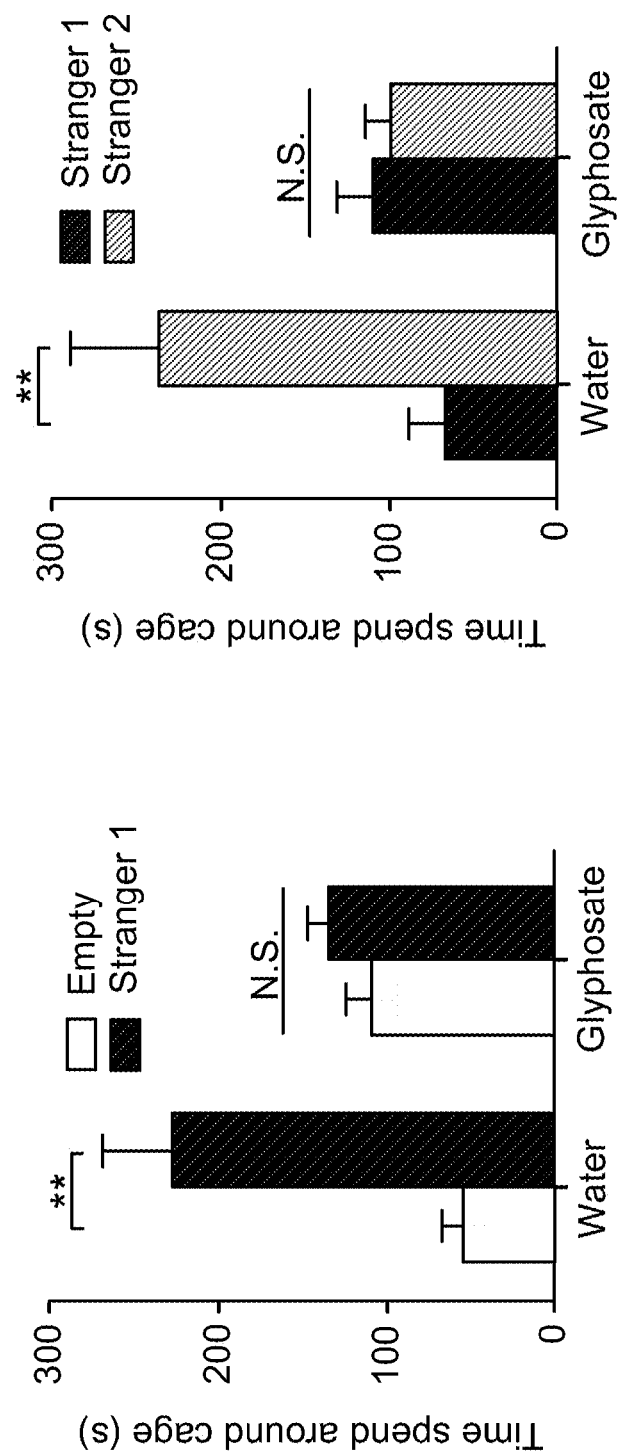

Body weight of glyphosate exposure mothers was significantly lower than that of water exposure mothers at E17 (FIGS. 8A and 8B). On P21 (weaning), we could detect blood levels of glyphosate in the mothers treated with 0.095% glyphosate and their offspring although glyphosate was not detected in the water treated group (FIGS. 8A and 8C). Locomotion, and prepulse inhibition (PPI) were not different between two groups (FIGS. 8D and 8F). In the novel object recognition test (NORT), offspring after maternal glyphosate exposure showed cognitive deficits (FIG. 8E). In the three-chamber test, juvenile offspring after maternal glyphosate exposure showed social interaction deficits compared to water treated group (FIG. 8G). The data suggest that maternal glyphosate exposure causes ASD-like cognitive deficits and social interaction deficits in juvenile offspring.

Increased expression of sEH in the brain of juvenile offspring after maternal glyphosate exposure. We measured the expression of sEH in the brain since increased expression of sEH in the PFC plays a role in the ASD-like behaviors after MIA (30). Protein levels of sEH in the PFC and striatum, but not hippocampus, from mothers treated with glyphosate were significantly higher than those of water-treated mice (FIG. 8H). Protein levels of sEH in the PFC, hippocampus, and striatum from juvenile offspring (P28) after maternal glyphosate exposure were significantly higher than those of water-treated mice (FIG. 8I). Furthermore, gene expressions of sEH (or Ephx2) mRNA in the PFC, hippocampus, and striatum from juvenile offspring (P28) after maternal glyphosate exposure were significantly higher than those of water-treated mice (FIG. 8J).

Figure 8K:
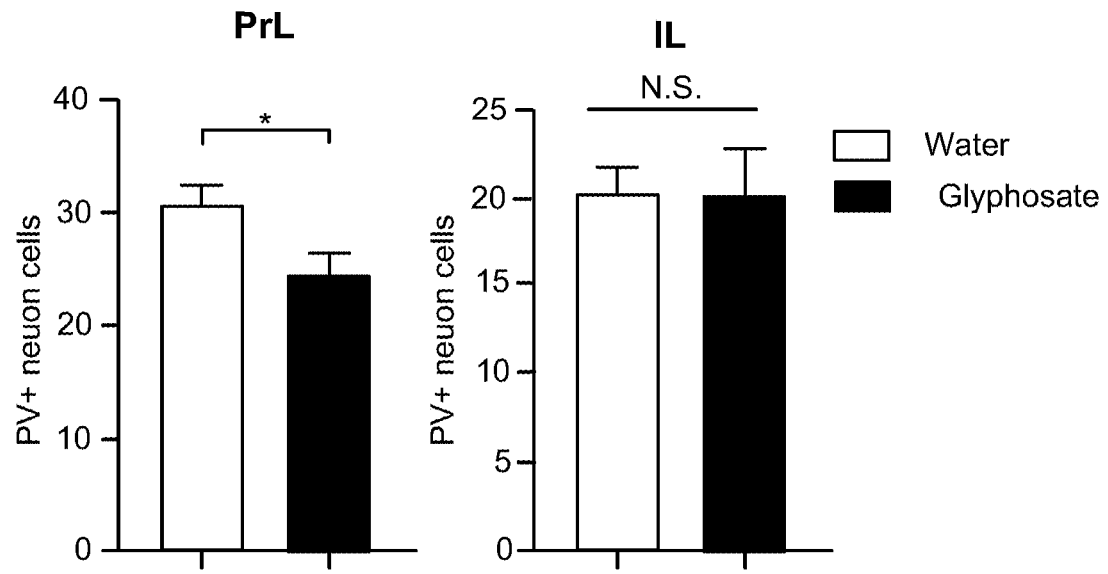
Figure 8K:
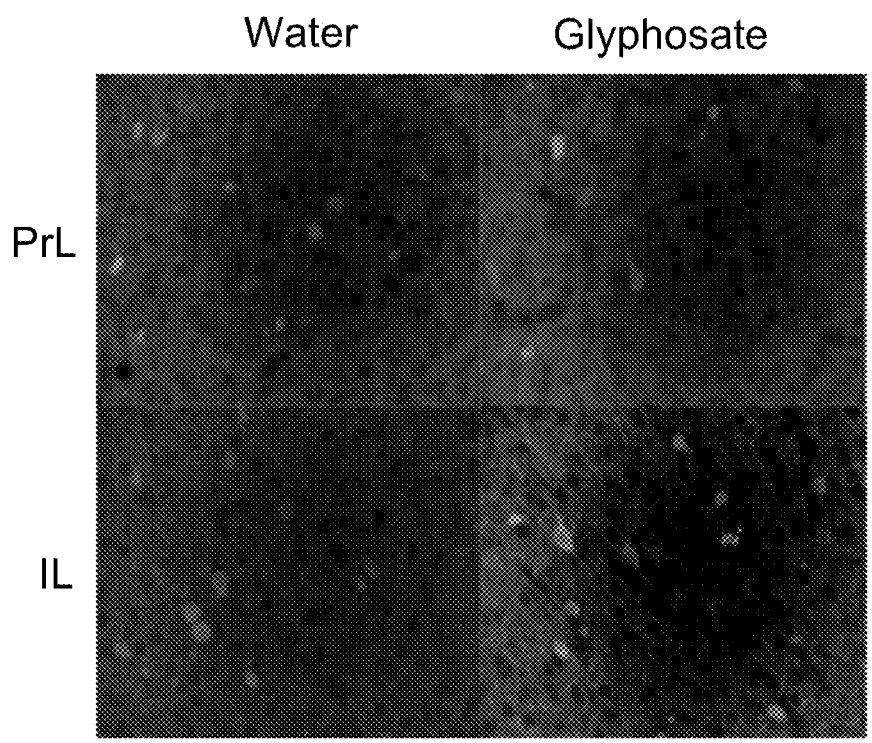
Figure 8K:
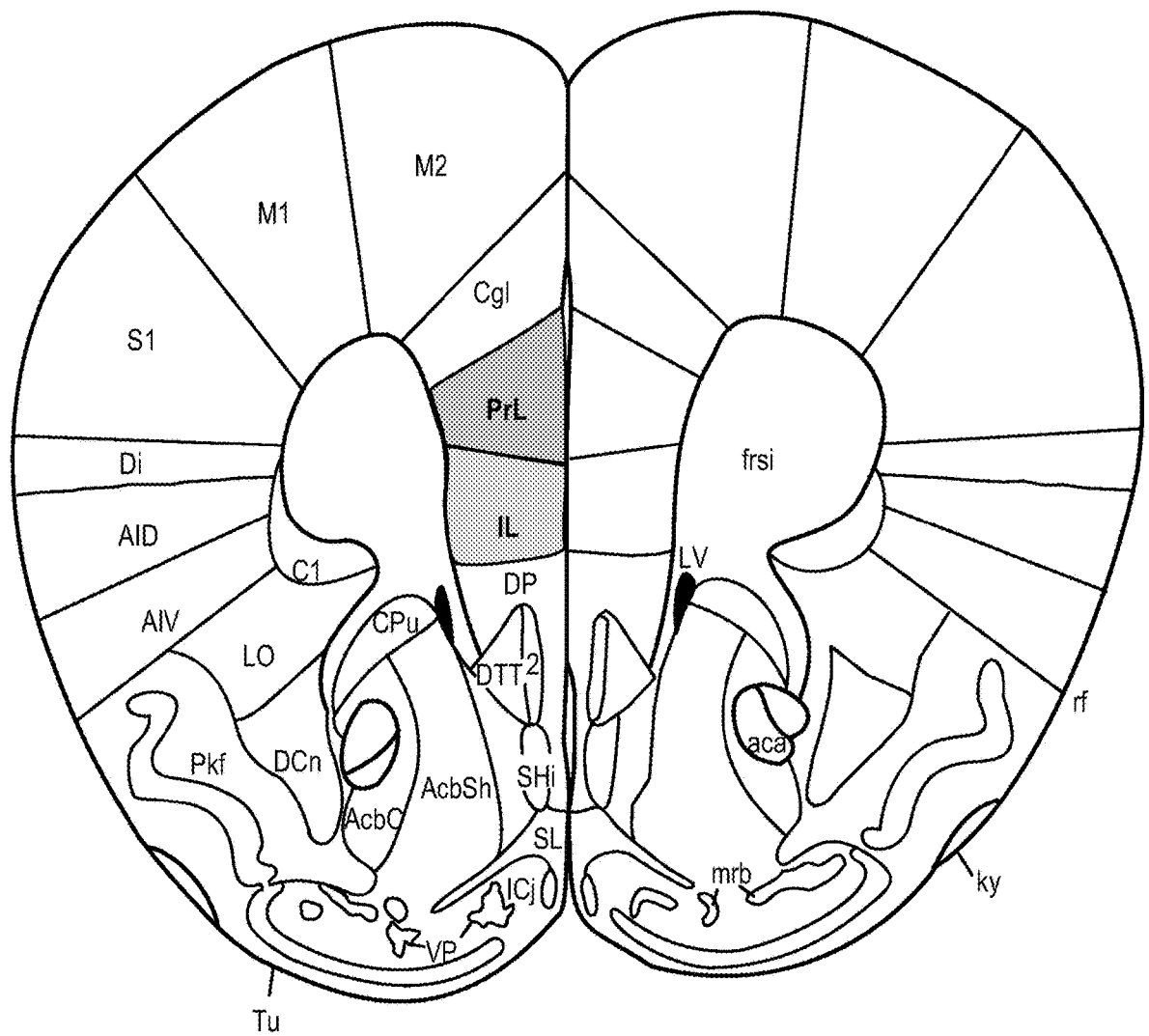

Next, we performed parvalbumin (PV)-immunohistochemistry in the brain from juvenile mice (FIG. 8K). PV-immunoreactivity in the prelimbic (PrL), not IL (infralimbic), of medial PFC in the offspring of maternal glyphosate exposure was significantly lower than that of water treated group (FIG. 8K).

Oxylipin analysis of blood, and brain regions. Using oxylipin analysis, we measured the levels of eicosanoid metabolites in the blood, PFC, hippocampus, and striatum from juvenile offspring (P28) after maternal glyphosate exposure (FIG. 9, Table 13-Table 17). Blood levels of many epoxides were significantly lower in juvenile offspring after maternal glyphosate exposure (Table 13). We found higher levels of 8(9)-EpETrE [8,9-epoxy-5Z,11Z,14Z-eicosatrienoic acid] compared to other EpFAs in the mouse brain. Levels of 8(9)-EpETrE in the PFC, hippocampus, and striatum were significantly lower in juvenile offspring (P28) after maternal glyphosate exposure (FIG. 9 and Table 14-Table 17). Lower levels of 8(9)-EpETrE in the brain regions from juvenile offspring after maternal glyphosate exposure support the increased expression of sEH in these regions. In contrast, tissue levels of other EpFAs in the PFC, hippocampus, and striatum from juvenile offspring after maternal glyphosate exposure were significantly higher than those of control mice (Table 14-Table 17).

TABLE 13

Oxylipin analysis in plasma

| Compounds | Control (nmol/ml) | Glyphosate (nmol/ml) | P value |
|---|---|---|---|
| 6-keto-PGF1a | 0.408 ± 0.047 | 0.252 ± 0.043 | 0.025 |
| TXB2 | 0.776 ± 0.120 | 0.548 ± 0.069 | 0.116 |
| 9,12,13-TriHOME | 17.372 ± 2.022 | 12.758 ± 1.096 | 0.060 |

TABLE 13-continued

Oxylipin analysis in plasma

| Compounds | Control (nmol/ml) | Glyphosate (nmol/ml) | P value |
|---|---|---|---|
| 9,10,13-TriHOME | 7.900 ± 0.981 | 5.220 ± 0.403 | 0.021 |
| PGF2a | 0.705 ± 0.055 | 0.462 ± 0.048 | 0.004 |
| PGE2 | 0.725 ± 0.013 | 0.704 ± 0.010 | 0.219 |
| PGD2 | 0.193 ± 0.012 | 0.138 ± 0.010 | 0.002 |
| 11,12-,15-TriHETrE | 0.724 ± 0.131 | 0.300 ± 0.072 | 0.011 |
| 19,20-DiHDPE | 10.277 ± 0.591 | 6.507 ± 0.444 | 0.000 |
| 14,15-DiHETrE | 0.686 ± 0.055 | 0.575 ± 0.051 | 0.156 |
| LTB3 | 2.586 ± 0.110 | 2.540 ± 0.525 | 0.942 |
| 16,17-DiHDPE | 2.591 ± 0.196 | 1.955 ± 0.201 | 0.036 |
| 11,12-DiHETrE | 0.414 ± 0.034 | 0.394 ± 0.045 | 0.726 |
| 13,14-DIHDPE | 0.731 ± 0.036 | 0.530 ± 0.056 | 0.007 |
| EKODE | 23.079 ± 11.409 | 12.405 ± 2.140 | 0.370 |
| 5,6-DiHETrE | 0.588 ± 0.031 | 0.417 ± 0.047 | 0.007 |
| 8-HEPE | 7.786 ± 0.622 | 7.652 ± 0.970 | 0.909 |
| 12-HEPE | 163.602 ± 36.795 | 92.380 ± 15.026 | 0.090 |
| 5-HEPE | 11.079 ± 1.083 | 8.117 ± 1.251 | 0.090 |
| 4,5-DiHDPE | 1.967 ± 0.134 | 1.527 ± 0.112 | 0.022 |
| 13-HODE | 108.971 ± 15.254 | 66.733 ± 9.200 | 0.029 |
| 9-HODE | 27.135 ± 3.659 | 17.293 ± 2.482 | 0.039 |
| 15(16)-EpODE | 27.169 ± 3.147 | 14.493 ± 1.929 | 0.004 |
| 15-HETE | 2.590 ± 0.326 | 1.985 ± 0.228 | 0.146 |
| 17(18)-EpETE | 9.343 ± 1.042 | 4.845 ± 0.480 | 0.002 |
| 17-HDoHE | 3948.481 ± 1343.355 | 1386.287 ± 316.090 | 0.080 |
| 11-HETE | 2.434 ± 0.172 | 1.949 ± 0.131 | 0.038 |
| 15-oxo-ETE | 0.966 ± 0.150 | 0.746 ± 0.105 | 0.244 |
| 14(15)-EpETE | 5.921 ± 0.937 | 2.316 ± 0.258 | 0.003 |
| 8-HETE | 8.502 ± 0.959 | 7.349 ± 0.718 | 0.349 |
| 12-HETE | 134.957 ± 20.785 | 90.069 ± 11.494 | 0.075 |
| 11(12)-EpETE | 7.002 ± 1.143 | 2.579 ± 0.284 | 0.002 |
| 8(9)-EpETE | 4.572 ± 0.577 | 0.863 ± 0.138 | 0.000 |
| 9-HETE | 0.087 ± 0.014 | 0.056 ± 0.012 | 0.120 |
| 15(S)-HETrE | 1.229 ± 0.163 | 0.743 ± 0.167 | 0.052 |
| 12-oxo-ETE | 831.657 ± 164.846 | 500.173 ± 99.031 | 0.102 |
| 5-HETE | 3.641 ± 0.230 | 2.137 ± 0.335 | 0.002 |
| 19(20)-EpDPE | 49.406 ± 6.516 | 19.092 ± 1.307 | 0.000 |
| 12(13)-EpOME | 94.456 ± 12.455 | 38.512 ± 4.378 | 0.001 |
| 14(15)-EpETrE | 8.183 ± 1.404 | 4.038 ± 0.637 | 0.019 |
| 9(10)-EpOME | 63.958 ± 12.021 | 28.326 ± 4.243 | 0.016 |
| 16(17)-EpDPE | 19.080 ± 3.183 | 7.978 ± 0.799 | 0.005 |
| 13(14)-EpDPE | 18.937 ± 3.242 | 8.177 ± 0.873 | 0.007 |
| 5-oxo-ETE | 29.432 ± 4.666 | 20.987 ± 2.839 | 0.151 |
| 10(11)-EpDPE | 29.647 ± 4.960 | 13.285 ± 1.234 | 0.007 |
| 11(12)-EpETrE | 12.482 ± 2.192 | 6.360 ± 1.002 | 0.026 |
| 7(8)-EpDPE | 402.209 ± 66.364 | 195.343 ± 16.718 | 0.010 |
| 8(9)-EpETrE | 33.331 ± 7.604 | 13.892 ± 2.938 | 0.042 |
| 8(9)-EpETrE alt | 6.203 ± 0.918 | 3.325 ± 0.409 | 0.013 |
| 5(6)-EpETrE | 41.145 ± 6.192 | 24.279 ± 3.524 | 0.035 |

The value (nmol/mL blood) are the mean ± SEM (n = 8 or 10).
The bold is statistically significant.
The bolded rows indicate that compounds decrease in glyphosate group compared with control.

TABLE 14

Oxylipin analysis in PFC

| Compounds | Control (pmol/g) | Glyphosate (pmol/g) | P value |
|---|---|---|---|
| 6-keto-PGF1a | 71.859 ± 10.966 | 88.691 ± 7.208 | 0.216 |
| TXB2 | 137.151 ± 16.944 | 246.160 ± 16.777 | 0.000 |
| 9,12,13-TriHOME | 40.375 ± 8.257 | 52.749 ± 6.979 | 0.267 |
| 9,10,13-TriHOME | 22.337 ± 4.483 | 31.772 ± 4.440 | 0.152 |
| PGF2a | 244.053 ± 34.499 | 431.431 ± 34.510 | 0.001 |
| PGE2 | 90.158 ± 13.679 | 137.389 ± 14.051 | 0.027 |
| PGD2 | 322.348 ± 26.200 | 439.532 ± 37.011 | 0.019 |
| 11,12-,15-TriHETrE | 14.229 ± 1.496 | 27.925 ± 2.262 | 0.000 |
| 19,20-DiHDPE | 7.162 ± 0.421 | 7.491 ± 0.703 | 0.693 |
| 14,15-DIHETrE | 1.256 ± 0.120 | 2.498 ± 0.243 | 0.000 |
| LTB3 | 45.708 ± 18.777 | 53.423 ± 26.072 | 0.816 |

TABLE 14-continued

Oxylipin analysis in PFC

| Compounds | Control (pmol/g) | Glyphosate (pmol/g) | P value |
|---|---|---|---|
| 16,17-DiHDPE | 0.707 ± 0.082 | 1.154 ± 0.110 | 0.004 |
| 11,12-DiHETrE | 0.863 ± 0.055 | 1.383 ± 0.124 | 0.001 |
| 13,14-DIHDPE | 0.431 ± 0.037 | 0.851 ± 0.076 | 0.000 |
| EKODE | 9.547 ± 0.671 | 12.663 ± 1.143 | 0.030 |
| 5,6-DiHETrE | 0.404 ± 0.039 | 0.699 ± 0.113 | 0.024 |
| 8-HEPE | 1.054 ± 0.155 | 0.959 ± 0.080 | 0.592 |
| 12-HEPE | 3.702 ± 1.166 | 6.850 ± 1.105 | 0.066 |
| 5-HEPE | 1.554 ± 0.180 | 1.760 ± 0.234 | 0.494 |
| 4,5-DiHDPE | 0.957 ± 0.210 | 1.083 ± 0.242 | 0.700 |
| 13-HODE | 40.531 ± 2.810 | 45.239 ± 3.261 | 0.288 |
| 9-HODE | 25.933 ± 2.089 | 32.184 ± 2.752 | 0.087 |
| 15(16)-EpODE | 1.095 ± 0.204 | 0.500 ± 0.121 | 0.022 |
| 15-HETE | 197.804 ± 29.559 | 313.016 ± 24.240 | 0.007 |
| 17(18)-EpETE | 0.588 ± 0.139 | 3.729 ± 1.017 | 0.007 |
| 17-HDoHE | 3452.039 ± 903.839 | 6200.527 ± 739.211 | 0.030 |
| 11-HETE | 188.165 ± 23.250 | 275.604 ± 19.707 | 0.010 |
| 15-oxo-ETE | 6.740 ± 0.540 | 10.104 ± 1.289 | 0.027 |
| 14(15)-EpETE | 0.590 ± 0.140 | 1.633 ± 0.487 | 0.054 |
| 8-HETE | 5.970 ± 1.038 | 7.904 ± 0.840 | 0.165 |
| 12-HETE | 125.575 ± 61.553 | 448.365 ± 69.003 | 0.003 |
| 11(12)-EpETE | 0.665 ± 0.211 | 2.775 ± 0.733 | 0.048 |
| 8(9)-EpETE | 1.752 ± 0.434 | 1.992 ± 0.638 | 0.760 |
| 9-HETE | 0.893 ± 0.173 | 1.826 ± 0.587 | 0.145 |
| 15(S)-HETrE | 5.611 ± 0.977 | 11.900 ± 1.029 | 0.000 |
| 12-oxo-ETE | 1331.981 ± 114.969 | 2140.116 ± 142.081 | 0.000 |
| 5-HETE | 13.471 ± 1.447 | 18.560 ± 1.797 | 0.041 |
| 19(20)-EpDPE | 89.030 ± 26.621 | 353.450 ± 99.156 | 0.019 |
| 12(13)-EpOME | 14.229 ± 3.214 | 67.240 ± 21.629 | 0.026 |
| 14(15)-EpETrE | 369.147 ± 105.708 | 1037.632 ± 291.994 | 0.045 |
| 9(10)-EpOME | 11.898 ± 2.490 | 57.775 ± 18.915 | 0.027 |
| 16(17)-EpDPE | 49.169 ± 14.279 | 195.454 ± 58.684 | 0.026 |
| 13(14)-EpDPE | 44.704 ± 12.681 | 190.175 ± 59.161 | 0.027 |
| 5-oxo-ETE | 144.718 ± 35.486 | 142.497 ± 16.459 | 0.955 |
| 10(11)-EpDPE | 61.132 ± 17.665 | 270.138 ± 86.641 | 0.030 |
| 11(12)-EpETrE | 364.169 ± 88.308 | 1128.684 ± 354.042 | 0.051 |
| 7(8)-EpDPE | 790.350 ± 192.868 | 3640.707 ± 1175.101 | 0.028 |
| 8(9)-EpETrE | 269969.7 ± 78049.8 | 12713.4 ± 6124.0 | 0.010 |
| 8(9)-EpETrE alt | 126.545 ± 30.496 | 447.323 ± 148.765 | 0.049 |
| 5(6)-EpETrE | 1312.892 ± 297.163 | 3862.881 ± 1353.639 | 0.082 |

The value (pmol/g tissue) are the mean ± SEM (n = 8 or 10).
The bold is statistically significant.
The bolded rows indicate that compounds that were increased or decreased in glyphosate group compared with control.

TABLE 15

Oxylipin analysis in the hippocampus

| Compounds | Control (pmol/ml) | Glyphosate (pmol/ml) | P value |
|---|---|---|---|
| 6-keto-PGF1a | 210.973 ± 17.307 | 113.103 ± 15.509 | 0.001 |
| TXB2 | 175.011 ± 15.917 | 198.203 ± 24.835 | 0.442 |
| 9,12,13-TriHOME | 46.966 ± 7.670 | 51.599 ± 10.194 | 0.721 |
| 9,10,13-TriHOME | 27.122 ± 4.287 | 29.123 ± 5.450 | 0.776 |
| PGF2a | 463.947 ± 37.827 | 314.752 ± 30.178 | 0.006 |
| PGE2 | 91.922 ± 10.680 | 68.947 ± 7.203 | 0.091 |
| PGD2 | 439.270 ± 24.157 | 349.020 ± 34.288 | 0.045 |
| 11,12-,15-TriHETrE | 26.992 ± 2.050 | 20.278 ± 1.789 | 0.024 |
| 19,20-DiHDPE | 7.827 ± 0.484 | 5.359 ± 0.322 | 0.000 |
| 14,15-DiHETrE | 1.375 ± 0.208 | 1.183 ± 0.095 | 0.412 |
| LTB3 | 81.636 ± 17.998 | 13.669 ± n.d. | n.d. |
| 16,17-DiHDPE | 0.753 ± 0.064 | 0.675 ± 0.093 | 0.500 |
| 11,12-DiHETrE | 1.120 ± 0.106 | 0.914 ± 0.053 | 0.099 |
| 13,14-DiHDPE | 0.493 ± 0.044 | 0.516 ± 0.089 | 0.823 |
| EKODE | 12.888 ± 1.489 | 11.362 ± 1.014 | 0.408 |
| 5,6-DiHETrE | 0.561 ± 0.047 | 0.470 ± 0.051 | 0.205 |
| 8-HEPE | 1.151 ± 0.086 | 1.415 ± 0.182 | 0.205 |
| 12-HEPE | 15.321 ± 3.628 | 9.094 ± 3.984 | 0.263 |
| 5-HEPE | 1.900 ± 0.242 | 2.917 ± 0.708 | 0.191 |
| 4,5-DiHDPE | 1.510 ± 0.192 | 1.572 ± 0.704 | 0.933 |
| 13-HODE | 59.332 ± 3.170 | 54.648 ± 8.929 | 0.627 |
| 9-HODE | 35.987 ± 1.888 | 31.282 ± 6.681 | 0.506 |
| 15(16)-EPODE | 0.726 ± 0.163 | 2.750 ± 0.907 | 0.033 |
| 15-HETE | 313.210 ± 26.117 | 263.402 ± 29.963 | 0.226 |
| 17(18)-EpETE | 4.252 ± 3.461 | 1.592 ± 0.499 | 0.457 |
| 17-HDoHE | 5370.298 ± 389.810 | 5997.276 ± 762.508 | 0.474 |
| 11-HETE | 296.258 ± 22.047 | 261.315 ± 27.149 | 0.331 |
| 15-oxo-ETE | 9.112 ± 0.576 | 8.232 ± 0.652 | 0.325 |
| 14(15)-EpETE | 2.515 ± 2.018 | 0.712 ± 0.184 | 0.385 |
| 8-HETE | 10.308 ± 0.983 | 5.383 ± 0.796 | 0.001 |
| 12-HETE | 304.652 ± 79.838 | 131.250 ± 40.185 | 0.068 |
| 11(12)-EpETE | 0.470 ± 0.147 | 1.254 ± 0.537 | 0.159 |
| 8(9)-EpETE | 0.912 ± 0.145 | 3.435 ± 0.784 | 0.008 |
| 9-HETE | 1.007 ± 0.194 | 2.073 ± 0.532 | 0.076 |
| 15(S)-HETrE | 9.162 ± 1.121 | 7.994 ± 1.430 | 0.528 |
| 12-oxo-ETE | 1524.203 ± 95.043 | 1245.436 ± 206.406 | 0.221 |
| 5-HETE | 19.187 ± 0.993 | 16.705 ± 0.992 | 0.094 |
| 19(20)-EpDPE | 42.255 ± 7.441 | 55.856 ± 8.656 | 0.251 |
| 12(13)-EpOME | 8.394 ± 1.398 | 11.355 ± 1.474 | 0.164 |
| 14(15)-EpETrE | 213.663 ± 39.064 | 241.703 ± 26.592 | 0.561 |
| 9(10)-EpOME | 7.129 ± 1.163 | 9.131 ± 1.032 | 0.216 |
| 16(17)-EpDPE | 22.265 ± 4.447 | 29.112 ± 4.286 | 0.284 |
| 13(14)-EpDPE | 19.371 ± 4.044 | 27.748 ± 3.955 | 0.158 |
| 5-oxo-ETE | 271.915 ± 35.187 | 94.461 ± 9.488 | 0.000 |

TABLE 15-continued

Oxylipin analysis in the hippocampus

| Compounds | Control (pmol/ml) | Glyphosate (pmol/ml) | P value |
|---|---|---|---|
| 10(11)-EpDPE | 24.579 ± 4.314 | 40.179 ± 5.185 | 0.034 |
| 11(12)-EpETrE | 190.566 ± 34.419 | 254.371 ± 33.701 | 0.204 |
| 7(8)-EpDPE | 335.530 ± 58.928 | 460.824 ± 81.977 | 0.232 |
| 8(9)-EpETrE | 58603.1 ± 18813.7 | 971.2 ± 484.7 | 0.012 |
| 8(9)-EpETrE alt | 64.121 ± 11.869 | 89.694 ± 12.609 | 0.159 |
| 5(6)-EpETrE | 731.031 ± 123.125 | 917.184 ± 134.826 | 0.323 |

The value (pmol/g tissue) are the mean ± SEM (n = 8 or 10).
The bold is statistically significant
The bolded rows indicate that compounds that were increased or decreased in glyphosate group compared with control.

TABLE 16

Oxylipin analysis in the striatum

| Compounds | Control (pmol/g) | Glyphosate (pmol/g) | P value |
|---|---|---|---|
| 6-keto-PGF1a | 80.263 ± 6.685 | 70.151 ± 4.942 | 0.240 |
| TXB2 | 143.486 ± 9.763 | 219.314 ± 15.121 | 0.001 |
| 9,12,13-TriHOME | 43.712 ± 6.665 | 59.110 ± 9.487 | 0.201 |
| 9,10,13-TriHOME | 25.621 ± 3.779 | 35.219 ± 5.532 | 0.169 |
| PGF2a | 327.993 ± 20.071 | 367.138 ± 24.248 | 0.230 |
| PGE2 | 62.314 ± 6.350 | 61.254 ± 3.057 | 0.882 |
| PGD2 | 335.832 ± 20.834 | 404.389 ± 30.557 | 0.080 |
| 11,12-,15-TriHETrE | 19.365 ± 1.301 | 28.513 ± 2.432 | 0.004 |
| 19,20-DiHDPE | 8.381 ± 0.316 | 8.734 ± 0.672 | 0.640 |
| 14,15-DiHETrE | 1.607 ± 0.058 | 2.399 ± 0.255 | 0.007 |
| LTB3 | 66.165 ± 17.957 | 74.130 ± 28.033 | 0.807 |
| 16,17-DIHDPE | 0.943 ± 0.039 | 1.427 ± 0.114 | 0.001 |
| 11,12-DIHETrE | 1.230 ± 0.075 | 1.461 ± 0.114 | 0.108 |
| 13,14-DiHDPE | 0.691 ± 0.043 | 0.849 ± 0.088 | 0.125 |
| EKODE | 15.864 ± 2.271 | 14.223 ± 1.256 | 0.535 |
| 5,6-DiHETrE | 0.628 ± 0.069 | 0.655 ± 0.058 | 0.766 |
| 8-HEPE | 1.323 ± 0.159 | 1.198 ± 0.106 | 0.519 |
| 12-HEPE | 11.726 ± 2.476 | 16.777 ± 3.707 | 0.272 |
| 5-HEPE | 2.635 ± 0.337 | 1.966 ± 0.253 | 0.130 |
| 4,5-DiHDPE | 1.376 ± 0.224 | 1.331 ± 0.320 | 0.910 |
| 13-HODE | 57.138 ± 6.208 | 61.551 ± 3.988 | 0.557 |
| 9-HODE | 36.146 ± 2.792 | 42.211 ± 2.648 | 0.132 |
| 15(16)-EpODE | 0.811 ± 0.270 | 0.837 ± 0.335 | 0.954 |
| 15-HETE | 254.134 ± 17.641 | 312.592 ± 16.237 | 0.025 |
| 17(18)-EpETE | 1.025 ± 0.244 | 7.282 ± 2.840 | 0.042 |
| 17-HDoHE | 6589.296 ± 752.871 | 7832.089 ± 1004.299 | 0.335 |
| 11-HETE | 221.438 ± 13.362 | 263.508 ± 14.043 | 0.044 |
| 15-oxo-ETE | 6.911 ± 0.402 | 15.203 ± 3.961 | 0.052 |
| 14(15)-EpETE | 0.760 ± 0.203 | 2.368 ± 0.640 | 0.023 |
| 8-HETE | 6.054 ± 1.093 | 7.063 ± 1.134 | 0.530 |
| 12-HETE | 254.764 ± 57.123 | 402.213 ± 68.023 | 0.114 |
| 11(12)-EpETE | 1.203 ± 0.270 | 2.950 ± 0.707 | 0.030 |
| 8(9)-EpETE | 1.662 ± 0.234 | 2.863 ± 1.693 | 0.491 |
| 9-HETE | 1.098 ± 0.293 | 2.001 ± 0.403 | 0.086 |
| 15(S)-HETrE | 7.618 ± 0.587 | 13.863 ± 0.898 | 0.000 |
| 12-oxo-ETE | 966.895 ± 140.198 | 2383.322 ± 205.470 | 0.000 |
| 5-HETE | 15.975 ± 1.179 | 21.009 ± 1.874 | 0.035 |
| 19(20)-EpDPE | 58.240 ± 11.472 | 373.365 ± 128.458 | 0.025 |
| 12(13)-EpOME | 11.880 ± 1.980 | 75.548 ± 26.478 | 0.028 |
| 14(15)-EpETrE | 206.025 ± 37.616 | 991.031 ± 327.438 | 0.028 |
| 9(10)-EpOME | 10.352 ± 2.057 | 64.909 ± 24.089 | 0.037 |
| 16(17)-EpDPE | 30.359 ± 6.931 | 186.178 ± 73.985 | 0.050 |
| 13(14)-EpDPE | 27.801 ± 5.702 | 196.586 ± 72.402 | 0.032 |
| 5-oxo-ETE | 256.279 ± 31.908 | 177.806 ± 23.342 | 0.063 |
| 10(11)-EpDPE | 39.670 ± 9.816 | 283.118 ± 111.688 | 0.044 |
| 11(12)-EpETrE | 208.934 ± 39.997 | 1056.655 ± 383.807 | 0.041 |
| 7(8)-EpDPE | 528.009 ± 139.936 | 3684.482 ± 1464.079 | 0.046 |
| 8(9)-EpETrE | 127384.1 ± 43766.3 | 7513.6 ± 2879.9 | 0.019 |
| 8(9)-EpETrE alt | 75.180 ± 15.974 | 256.271 ± 63.811 | 0.010 |
| 5(6)-EpETrE | 821.143 ± 187.923 | 2286.424 ± 589.971 | 0.024 |

The value (pmol/g tissue) are the mean ± SEM (n = 8 or 10).
The bold is statistically significant
The bolded rows indicate that compounds that increased or decreased in glyphosate group compared with control.

TABLE 17

Levels of NMDAR-related amino acids in the plasma, PFC, hippocampus, and striatum of offspring

| | Glutamate | Glutamine | Glycine | L-Serine | D-Serine | GABA |
|---|---|---|---|---|---|---|
| | | | Plasma (nmol/ml) | | | |
| Control | 60.047 ± 5.976 | 508.014 ± 13.285 | 333.402 ± 13.215 | 148.271 ± 6.711 | 3.841 ± 0.293 | N.D. |
| Glyphosate | 38.003 ± 1.974** | 496.268 ± 15.748 | 354.185 ± 9.806 | 144.824 ± 4.622 | 7.522 ± 0.578*** | N.D. |
| | | | PFC (nmol/mg tissue) | | | |
| Control | 11.827 ± 0.293 | 5.486 ± 0.194 | 0.804 ± 0.033 | 0.712 ± 0.032 | 0.345 ± 0.017 | 2.243 ± 0.048 |
| Glyphosate | 10.392 ± 0.377** | 5.053 ± 0.243 | 0.705 ± 0.023* | 0.622 ± 0.016* | 0.313 ± 0.010 | 2.060 ± 0.058* |
| | | | Hippocampus (nmol/mg tissue) | | | |
| Control | 11.477 ± 0.295 | 4.979 ± 0.147 | 0.982 ± 0.143 | 0.764 ± 0.041 | 0.277 ± 0.011 | 2.736 ± 0.306 |
| Glyphosate | 9.350 ± 0.282*** | 4.765 ± 0.137 | 0.725 ± 0.030 | 0.662 ± 0.037 | 0.259 ± 0.017 | 2.469 ± 0.097 |

TABLE 17-continued

Levels of NMDAR-related amino acids in the plasma, PFC, hippocampus, and striatum of offspring

|  | Glutamate | Glutamine | Glycine | L-Serine | D-Serine | GABA |
|---|---|---|---|---|---|---|
| Striatum (nmol/mg tissue) | | | | | | |
| Control | 8.712 ± 0.348 | 5.756 ± 0.302 | 0.757 ± 0.041 | 0.771 ± 0.056 | 0.309 ± 0.022 | 2.925 ± 0.177 |
| Glyphosate | 7.745 ± 0.141* | 5.735 ± 0.319 | 0.755 ± 0.039 | 0.715 ± 0.032 | 0.281 ± 0.010 | 3.076 ± 0.151 |

Data are expressed as the mean ± SEM (n = 9, Glyphosate: n = 10).
The bold is statistically significant.
*P < 0.05, **P < 0.001 compared to control group (Student's t test).
N.D.: Not determined.

Measurement of amino acids in the blood and brain. Next, we measured levels of NMDAR-related amino acids (i.e., glutamate, glutamine, glycine, D-serine, L-serine, GABA) in the plasma and brains of juvenile offspring (P28) after maternal glyphosate exposure. Maternal glyphosate exposure caused significant reductions of glutamate in the plasma and brain regions. In addition, maternal glyphosate exposure caused significant reductions of other amino acids (i.e., glycine, L-serine, GABA) in the PFC. The data suggest abnormalities in NMDAR-related neurotransmission in the PFC of juvenile offspring after maternal glyphosate exposure.

16S rRNA analysis and measurement of short-chain fluty acids of fecal samples of juvenile offspring after maternal glyphosate exposure. We performed 16S rRNA analysis of fecal samples of offspring (P28). Maternal glyphosate exposure caused abnormal composition of gut microbiota in juvenile offspring (FIG. 10). At the species level, the relative abundance of *Eubacterium plexicaudatum*, *Lachnospiraceae bacterium* 538, and *Clostridium tertium* was significantly lower in the juvenile offspring after maternal glyphosate exposure compared to water-treated group (FIG. 10). In contrast, the relative abundance of *Clostridium* sp. Clone-1, *Enterorhabdus muris*, *Clostridium* sp. Clone-46, and *Butyricimonas virosa* was significantly higher in juvenile offspring after maternal glyphosate exposure compared to water-treated group (FIG. 10). Furthermore, levels of acetic acid in the fecal samples of the offspring were significantly increased after maternal glyphosate exposure (FIG. 10). Other short chain fatty acids including propionic acid, butyric acid, and valeric acid were not different. The data suggest that maternal glyphosate exposure causes abnormal composition of gut microbiota in juvenile offspring.

Figure 11A:
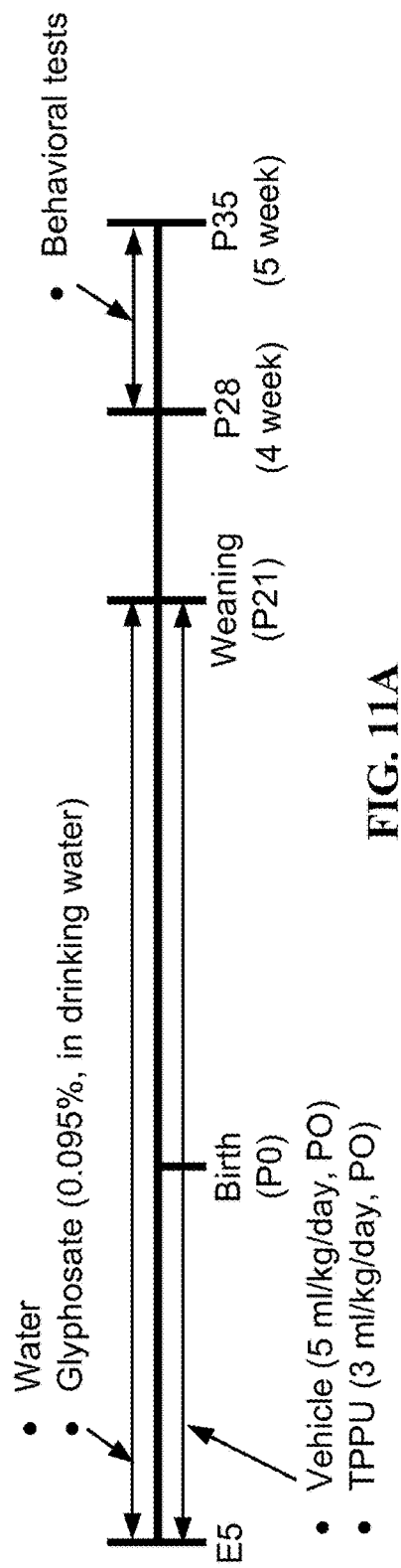
Figure 11C:
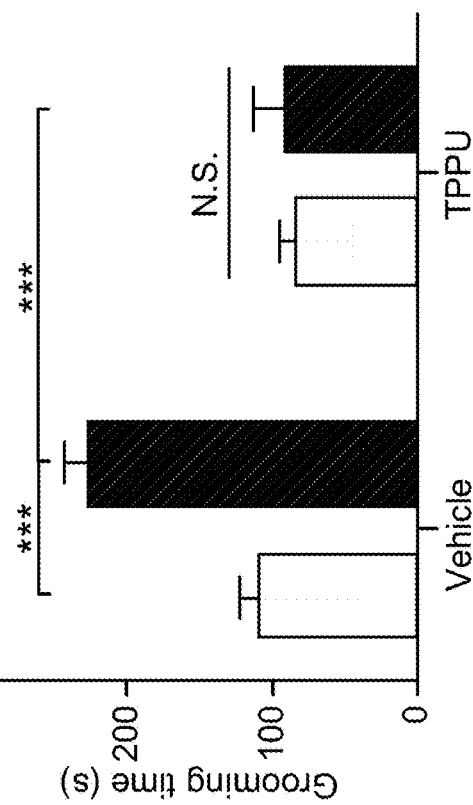
Figure 11B:
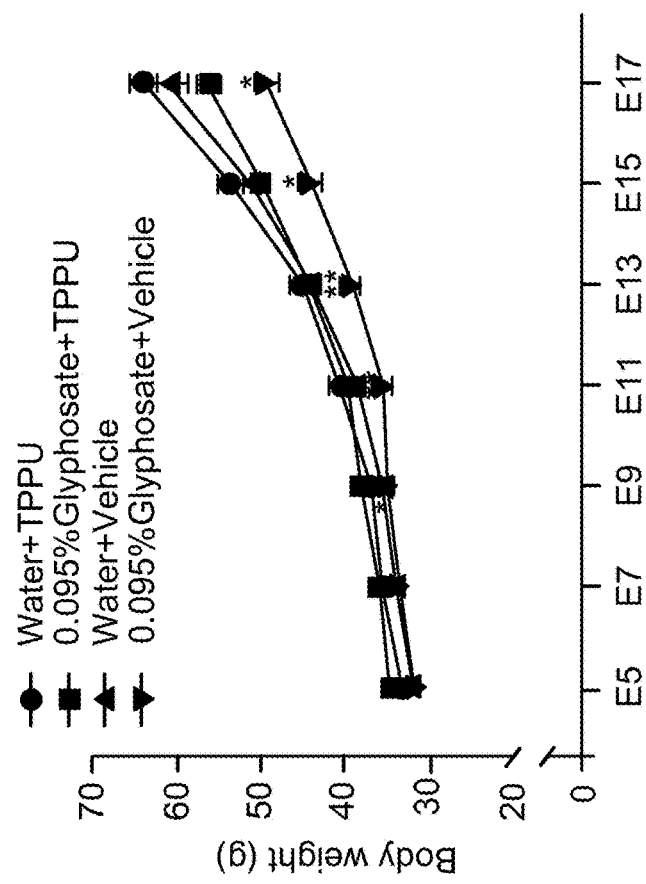
Figure 11D:
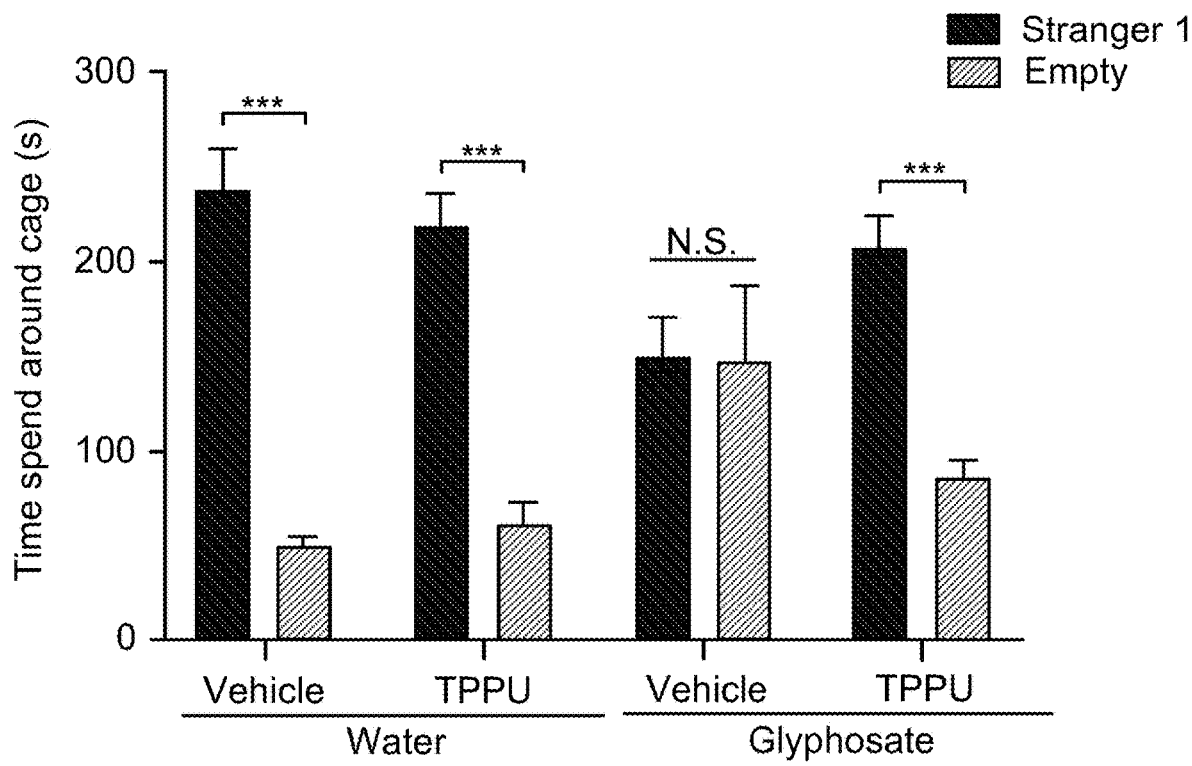
Figure 11D:
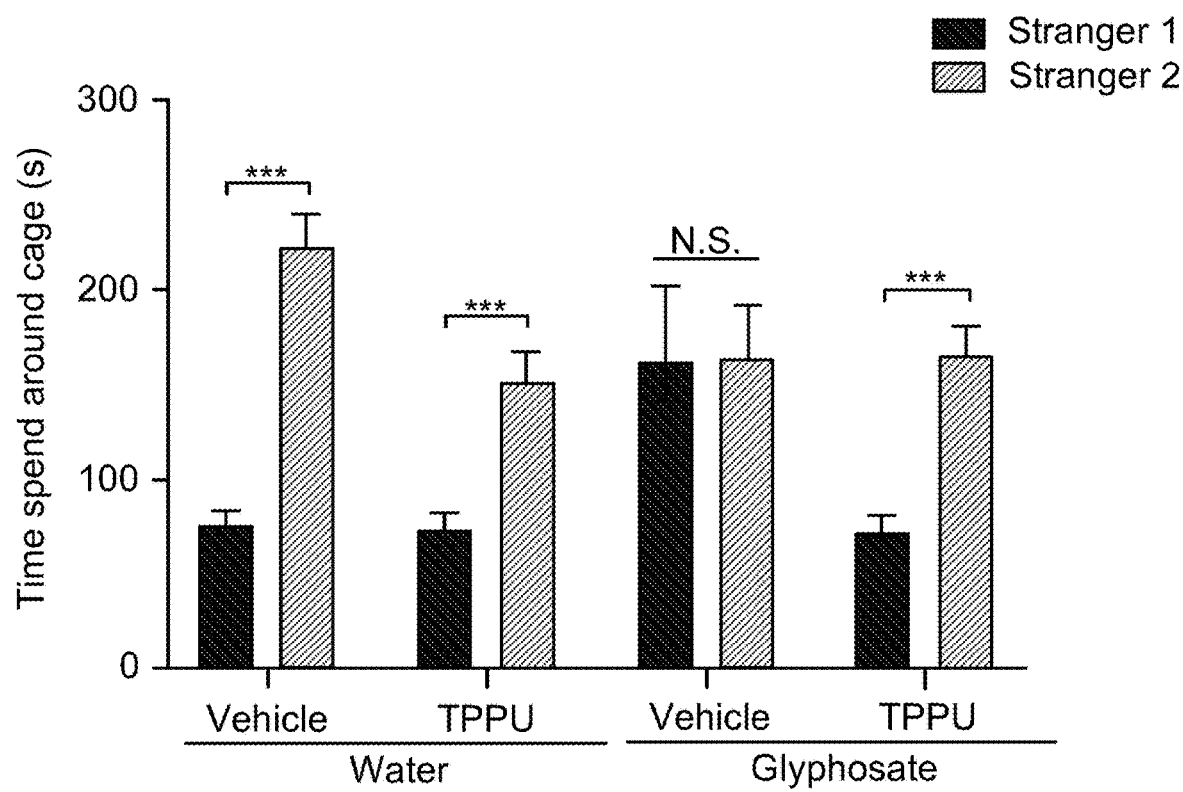

Effects of TPPU on ASD-like behaviors in juvenile offspring of maternal glyphosate exposure. Water or glyphosate was given to pregnant mice from E5 to P21. In addition, the pregnant mice were administrated orally with vehicle (5 ml/kg/day) or TPPU (3 mg/kg/day) from E5 to P21. Behavioral tests such as grooming test and three-chamber social interaction test were performed from P28 to P35 (FIG. 11A). Body weight was significantly increased in TPPU-treated glyphosate exposure mothers compared to vehicle-treated glyphosate exposure mothers (FIG. 11B). Treatment with TPPU significantly ameliorated the increased grooming time of juvenile offspring after maternal glyphosate exposure (FIG. 11C). In the three-chamber social interaction test, treatment with TPPU significantly improved social interaction deficits in juvenile offspring after maternal glyphosate exposure (FIG. 11D).

Discussion

The present results demonstrate a key role of sEH in the onset of ASD-like behaviors in juvenile offspring after maternal glyphosate exposure. The major findings of the present study are as follows: First, exposure of 0.095% glyphosate during pregnancy and lactation caused ASD-like behaviors in juvenile offspring. Second, expression of sEH protein in the PFC, hippocampus, and striatum from juvenile offspring after maternal glyphosate exposure was higher than that of control group. Oxylipin analysis showed a marked reduction of 8(9)-EpETrE in the plasma, PFC, hippocampus, and striatum from juvenile offspring after maternal glyphosate exposure, supporting higher levels of sEH in these brain regions. Third, maternal glyphosate exposure caused reduced PV-immunoreactivity in the prelimbic of medial PFC in the offspring compared to water treated group. Furthermore, maternal glyphosate exposure caused significant alterations of NMDAR-related amino acids in the blood and brain of offspring. Fourth, maternal glyphosate exposure caused significant abnormal composition of gut microbiota and increased levels of acetic acid and isobutyric acid in the fecal samples from juvenile offspring. Finally, the repeated treatment with TPPU in glyphosate-treated pregnant mice from pregnancy (E5) to weaning (P21) could prevent the onset of ASD-like behaviors (i.e., increased grooming time and social interaction deficits) in juvenile offspring after maternal glyphosate exposure. Collectively, these findings suggest that sEH plays a key role in the development of ASD-like behavioral abnormalities in offspring after maternal glyphosate exposure, and that sEH inhibitors may prove to be promising prophylactic or therapeutic drugs for ASD.

In this study, we found increased expression of sEH protein in the PFC of juvenile offspring after maternal glyphosate exposure, consistent with our report using MIA (30). Thus, it seems that increases in the sEH in the PFC and other regions (hippocampus and striatum) might play a role in the behavioral and biochemical abnormalities seen in juvenile offspring after maternal glyphosate exposure. Previously, we reported higher levels of EPHX2 mRNA in the postmortem brain samples from ASD patients (30). These findings suggest that increased metabolism of EpFAs to the corresponding diols by increased sEH may play a role in the pathogenesis of ASD, although further detailed studies on how maternal glyphosate exposure induces abnormalities in the eicosanoid metabolism by sEH and behavioral abnormalities in offspring are needed.

In this study, we found decreased levels of many EpFAs including 8(9)-EpETrE in the blood of juvenile offspring after maternal glyphosate exposure compared to water treated group. Interestingly, tissue levels of 8(9)-EpETrE, most abundant EpFA in the brain, were significantly lower in the PFC, hippocampus, and striatum from juvenile offspring after maternal glyphosate exposure than those of control mice, supporting an increased activity of sEH in these brain regions. The data of 8(9)-EpETrE are consistent with our previous report using MIA model of ASD (30). Although the precise mechanisms underlying the relationship between 8(9)-EpETrE and sEH in the brain from juvenile offspring after maternal glyphosate exposure are currently unclear, it seems that low level of 8(9)-EpETrE by increased levels of sEH in the brain may be involved in behavioral abnormalities of offspring after maternal glyphosate exposure. By contrast, other EpFAs were significantly higher in the brain regions of juvenile offspring after maternal glyphosate exposure than those of water treated group although tissue levels of sEH in the brain regions were decreased after maternal glyphosate exposure. Although the reasons underlying this discrepancy are currently unknown, it seems that multiple pathways may contribute to formation and degradation of EpFAs in the brain regions.

It is recognized that mechanisms of action of glyphosate is to disrupt the shikimate pathway which is absent from human cells. However, human gut microbiomes contain the shikimate pathway which plays a key role in the synthesis of aromatic amino acids in both plants and microbiomes (11, 44-46). Therefore, it is suggested that exposure to glyphosate can affect gut microbiota in the humans (6,47). In this study, we found abnormal composition of gut microbiota such as *Clostridium* in juvenile offspring after maternal glyphosate exposure. A recent review pointed an interaction between *Clostridium* bacteria and ASD (48). In addition, we found higher levels of acetic acid in fecal samples of juvenile offspring after maternal glyphosate exposure. It is reported that fecal levels of acetic acid in children with ASD were higher than those on controls (49). It seems that increased intestinal permeability by acetic acid might play a role in fecal production of acetic acid since acetic acid plays a role in gut epithelial barrier function (49). Given the crucial role of gut microbiota in ASD pathogenesis (39,50, 51), abnormal composition of gut microbiota may be, in part, involved in the ASD-like behaviors in offspring after maternal glyphosate exposure. At present, specific bacteria which can cause ASD were not yet identified. Therefore, further study on the role of gut microbiota on glyphosate-induced ASD is needed.

In this study, we found that maternal exposure to 0.095% glyphosate causes ASD-like behaviors and abnormal composition of gut microbiota in juvenile offspring. Although it is unknown whether the concentration of 0.095% glyphosate is corresponded with the concentration of glyphosate in human pregnancy, it seems that maternal glyphosate exposure could have detrimental side effects in offspring. A cohort study on measurement of blood (or urine) levels of glyphosate in pregnant mothers who have their offspring with or without ASD is of great interest. Although the current animal data do not necessarily translate to humans, further study connecting animal data with the findings from epidemiological studies is needed to identify the detailed mechanisms of action of glyphosate exposure for ASD pathogenesis.

In conclusion, this study suggests that maternal glyphosate exposure might play a key role in the etiology of ASD-like behaviors in offspring through increased activity of sEH in the brain. Therefore, sEH inhibitors appear to be new prophylactic or therapeutic drugs for maternal glyphosate exposure-related developmental disorders such as ASD.

REFERENCES

1. Lai M C, Lombardo M V, Baron-Cohen S (2014) Autism. *Lancet* 383:896-910.
2. Lord C, Elsabbagh M, Baird Veenstra-Vanderweele J (2018) Autism spectrum disorder. *Lancet* 392:508-520.
3. Hansen S N, Schendel D E, Parner E T (2015) Explaining the increase in the prevalence of autism spectrum disorders: the proportion attributable to changes in reporting practices. *JAMA Pediatr* 169:56-62.
4. Baio J, et al. (2018) Prevalence of autism spectrum disorder among children aged 8 years—autism and developmental disabilities monitoring network, 11 sites, United States, 2014. *MMWR Surveill Summ* 67: 1-23.
5. Hallmayer J, et al. (2011) Genetic heritability and shared environmental factors among twin pairs with autism. *Arch Gen Psychiatry* 68:1095-1102.
6. Sealey L A, et al. (2016) Environmental factors in the development of autism spectrum disorders. *Environ Int* 88:288-298.
7. Sagiv S K, et al. (2018) Prenatal organophosphate pesticide exposure and traits related to autism spectrum disorders in a population living in proximity to agriculture. *Environ Health Perspect* 126:047012.
8. Kim J Y, et al. (2019) Environmental risk factors and biomarkers for autism spectrum disorder: an umbrella review of the evidence. *Lancet Psychiatry* 6:590-600.
9. Bradberry S M, Proudfoot A T, Vale J A (2004) Glyphosate poisoning. *Toxicol Rev* 23:159-167.
10. Kier L D, Kirkland D J (2013) Review of genotoxicity studies of glyphosate and glyphosate-based formulations. *Crit Rev Toxicol* 43:283-315.
11. Samsel A, Seneff S (2013) Glyphosate, pathways to modern diseases II: Celiac sprue and gluten intolerance. *Interdiscip Toxicol* 6:159-184.
12. Swanson N L, Leu A, Abrahamson J, Wallet B (2014) Genetically engineered crops, glyphosate and the deterioration of health in the United States of America. *J Organic Systems* 9: 2014.
13. Samsel A, Seneff S (2015) Glyphosate, pathways to modern diseases III: Manganese, neurological diseases, and associated pathologies. *Surg Neurol Int* 6:45.
14. von Ehrenstein O S, et al. (2019) Prenatal and infant exposure to ambient pesticides and autism spectrum disorder in children: population based case-control study. *BMJ* 364:1962.
15. Estes M L, McAllister A K (2016) Maternal immune activation: Implication for neuropsychiatric disorders. *Science* 353:772-777.
16. Jiang H Y, et al. (2016) Maternal infection during pregnancy and risk of autism spectrum disorders: A systematic review and meta-analysis. *Brain Behav Immun* 58:165-172.
17. Careaga M, Murai T, Bauman M D (2017) Maternal immune activation and autism spectrum disorder: From rodents to nonhuman and human primates. *Biol Psychiatry* 81:391-401.
18. Zerbo O, Qian Y, Yoshida C, Fireman B H, Klein N P, Croen L A (2017) Association between influenza infection and vaccination during pregnancy and risk of autism spectrum disorder. *JAMA Pediatr* 171:e163609.
19. Hashimoto K (2019) Recent advances in the early intervention in schizophrenia: future direction from preclinical findings. *Curr Psychiatry Rep* 21:75.
20. Brown A S, Meyer U (2018) Maternal immune activation and neuropsychiatric illness: A translational research perspective. *Am J Psychiatry* 175:1073-1083.
21. Morisseau C, Hammock B D (2005) Epoxide hydrolases: mechanisms, inhibitor designs, and biological roles. *Annu Rev Pharmacol Toxicol* 45:311-333.

22. Imig J D, Hammock B D (2009) Soluble epoxide hydrolase as a therapeutic target for cardiovascular diseases. *Nat Rev Drug Discov* 8:794-805.
23. Morisseau C, Hammock B D (2013) Impact of soluble epoxide hydrolase and epoxyeicosanoids on human health. *Annu Rev Pharmacol Toxicol* 53:37-58.
24. Hashimoto K (2019) Role of soluble epoxide hydrolase in metabolism of PUFAs in psychiatric and neurological disorders. *Front Pharmacol* 10:36.
25. Ren Q, et al. (2016) Gene deficiency and pharmacological inhibition of soluble epoxide hydrolase confers resilience to repeated social defeat stress. *Proc Natl Acad Sci USA* 113:E1944-E1952.
26. Hashimoto K (2016) Soluble epoxide hydrolase: a new therapeutic target for depression. *Expert Opin Ther Targets* 20:1149-1151.
27. Wagner K M, McReynolds C B, Schmidt W K, Hammock B D (2017) Soluble epoxide hydrolase as a therapeutic target for pain, inflammatory and neurodegenerative diseases. *Pharmacol Ther* 180:62-76.
28. Swardfager W, et al. (2018) Metabolic/inflammatory/vascular comorbidity in psychiatric disorders; soluble epoxide hydrolase (sEH) as a possible new target. *Neurosci Biobehav Rev* 87:56-66.
29. Ren Q, et al. (2018) Soluble epoxide hydrolase plays a key role in the pathogenesis of Parkinson's disease. *Proc Natl Acad Sci USA* 115:E5815-E5823.
30. Ma M, et al. (2019) Key role of soluble epoxide hydrolase in the neurodevelopmental disorders of offspring after maternal immune activation. *Proc Natl Acad Sci USA* 116:7083-7088.
31. Hashimoto K (2019) Understanding the link between maternal infections and neurodevelopmental disorders in offspring: The role of abnormalities in metabolism of polyunsaturated fatty acids. *Brain Behav Immun* 81:4-5.
32. Atone J, Wagner K, Hashimoto K, Hammock B D (in press) Prostaglandins and other lipid mediators cytochrome P450 derived epoxidized fatty acids as a therapeutic tool against neuroinflammatory diseases. *Prostaglandins Other Lipid Mediat* 2019 November 4:106385. doi: 10.1016/j.prostaglandins.2019.106385.
33. Shinohe A, et al. (2006) Increased serum levels of glutamate in adult patients with autism. *Prog Neuropsychopharmacol Biol Psychiatry* 30:1472-1477.
34. Shimmura C, et al. (2011) Alteration of plasma glutamate and glutamine levels in children with high-functioning autism. *PLoS One* 6:e25340.
35. Zheng Z, Zhu T, Qu Y, Mu D (2016) Blood glutamate levels in autism spectrum disorder: a systematic review and meta-analysis. *PLoS One* 11:e0158688.
36. Wang M, et al. (2019) Alterations in gut glutamate metabolism associated with changes in gut microbiota composition in children with autism spectrum disorder. *mSystems* 4:e00321-18.
37. Tomova A, et al. (2015) Gastrointestinal microbiota in children with autism in Slovakia. *Physiol Behav* 138:179-187.
38. Vuong H E, Hsiao E Y (2017) Emerging roles for the gut microbiome in autism spectrum disorder. *Biol Psychiatry* 81:411-423.
39. Liu F, et al. (2019) Altered composition and function of intestinal microbiota in autism spectrum disorders: a systematic review. *Transl Psychiatry* 9:43.
40. Xu M, Xu X, Li J, Li F (2019) Association between gut microbiota and autism spectrum disorder: a systematic review and meta-analysis. *Front Psychiatry* 10:473.
41. Rose T E, et al. (2010) 1-Aryl-3-(1-acylpiperidin-4-yl) urea inhibitors of human and murine soluble epoxide hydrolase: structure-activity relationships, pharmacokinetics, and reduction of inflammatory pain. *J Med Chem* 53:7067-7075.
42. Ostermann A I, et al. (2015) Oral treatment of rodents with soluble epoxide hydrolase inhibitor 1-trifluoromethoxyphenyl-3-(1-propionylpiperidin-4-yl)urea (TPPU): bioavailability, resulting drug levels and modulation of oxylipin pattern. *Prostaglandins Other Lipid Mediat* 121(Pt A):131-137.
43. Williams G M, Kroes R, Munro I C (2000) Safety evaluation and risk assessment of the herbicide Roundup and its active ingredient, glyphosate, for humans. *Regul Toxicol Pharmacol* 31:117-165.
44. Hellmann K M, Weaver L M (1999). The shikimate pathway. *Annu Rev Plant Physiol Plant Mol Biol* 50:473-503.
45. Maeda H, Dudareva N (2012) The shikimate pathway and aromatic amino acid biosynthesis in plants. Annu Rev Plant Biol 63:73-105.
46. Samsel A, Seneff S (2013) Glyphosate's suppression of cytochrome P450 enzymes and amino acid biosynthesis by the gut microbiome: pathways to modern diseases. *Entropy* 15:1416-1463.
47. Rueda-Ruzafa L, Cruz F, Roman P, Cardona D (2019) Gut microbiota and neurological effects of glyphosate. *Neurotoxicology* 75:1-8.
48. Argou-Cardozo I, Zeidán-Chuliá F (2018) *Clostridium* bacteria and autism spectrum conditions: a systematic review and hypothetical contribution of environmental glyphosate levels. *Med Sci (Basel)* 6:E29.
49. Wang L, et al. (2012) Elevated fecal short chain fatty acid and ammonia concentrations in children with autism spectrum disorder. *Dig Dis Sci* 57:2096-2102.
50. Cryan J F, et al. (2019) The micribiota-gut-brain axis. *Physiol Rev* 99:1877-2013.
51. Sherwin E, Bordenstein S R, Quinn J L, Dinan T G, Cryan J F (2019) Microbiota and the social brain. *Science* 366:eaar2016.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method of reducing, ameliorating, and/or mitigating, autism spectrum disorder (ASD) related to prenatal maternal immune activation in an individual in need thereof consisting of administering to said individual an agent that increases the level of epoxy-fatty acids (EpFAs),
wherein said individual experienced maternal immune activation one or more times during gestation, and
the agent that increases the level of epoxy-fatty acids is compound of Formula (II)

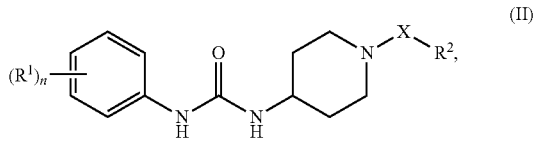

or a pharmaceutically acceptable salt thereof, wherein
X is C(O) or S(O)$_2$;
each $R^1$ is independently H, halogen, $C_{1-6}$ alkyl, $C_{1-6}$ alkoxy, $C_{1-6}$ haloalkyl, $C_{1-6}$ haloalkoxy, —O—aryl, heterocycloalkyl having 5-6 ring members and at least 1 N heteroatom, —OH, —NO$_2$, or —C(O)OR$^3$, wherein at least 1 $R^1$ is other than H;
$R^2$ is $C_{1-6}$ alkyl, $C_{1-6}$ haloalkyl, cycloalkyl having 3-6 members, or $C_{1-6}$ alkyl-heterocycloalkyl having from 5-6 ring members and at least 2 N heteroatoms as ring members;
$R^3$ is H or $C_{1-6}$ alkyl; and
subscript n is 1, 2, 3, 4, or 5.

2. The method of claim 1, wherein said individual is a child, a juvenile, or an adult.

3. The method of claim 1, wherein said prenatal maternal immune activation was caused by a viral or bacterial infection, maternal malnourishment, drug use, alcohol abuse, or exposure to a toxin during gestation.

4. The method of claim 3, wherein said toxin is a pesticide or an herbicide.

5. The method of claim 4, wherein said pesticide or herbicide is selected from the group consisting of glyphosate, malathion, pentachloronitrobenzene, parathion, tetrachlorvinphos, propoxur, toxaphene, and metiram.

6. The method of claim 1, wherein the epoxy-fatty acids are selected from the group consisting of cis-epoxyeicosantrienoic acids ("EETs"), epoxyeicosatetraenoic acids ("EEQs"), and epoxydocosapentaenoic acids ("EDPs"), and mixtures thereof.

7. The method of claim 1, wherein the epoxy-fatty acids are selected from the group consisting of cis-epoxyeicosantrienoic acids ("EETs"), epoxides of linoleic acid, epoxides of eicosapentaenoic acid ("EPA"), epoxides of docosahexaenoic acid ("DHA"), epoxides of cis-7,10,13,16,19-docosapentaenoic acid, and mixtures thereof.

8. The method of claim 1, wherein the agent that increases the level of epoxy-fatty acids is an inhibitor of soluble epoxide hydrolase ("sEH").

9. The method of claim 8, wherein the inhibitor of SEH is selected from the group consisting of:
1-(1-methylsulfonyl-piperidin-4-yl)-3-(4-trifluoromethoxy-phenyl)-urea (TUPS; compound 1709);
1-trifluoromethoxyphenyl-3-(1-propionylpiperidin-4-yl) urea (TPPU; compound 1770);
1-(1-ethylsulfonyl-piperidin-4-yl)-3-(4-trifluoromethoxyphenyl)-urea (TUPSE; compound 2213); and
1-(1-(cyclopropanecarbonyl) piperidin-4-yl)-3-(4-(trifluoromethoxy)phenyl)urea (CPTU; compound 2214).

10. The method of claim 1, wherein prior to administration of the agent that increases the level of epoxy-fatty acids, the individual has been diagnosed as having autism spectrum disorder.

11. A method of reducing, ameliorating, and/or mitigating, autism spectrum disorder in an individual consisting of administering to said individual an agent that increases the level of epoxy-fatty acids,
wherein the agent that increases level of epoxy-fatty acids is a compound of Formula (II)

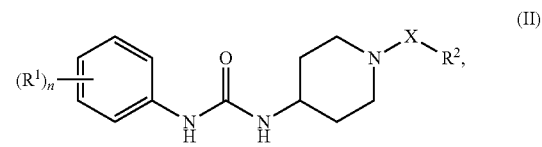

or a pharmaceutically acceptable salt thereof, wherein
X is C(O) or S(O)$_2$;
each $R^1$ is independently H, halogen, $C_{1-6}$ alkyl, $C_{1-6}$ alkoxy, $C_{1-6}$ haloalkyl, $C_{1-6}$ haloalkoxy, —O—aryl, heterocycloalkyl having 5-6 ring members and at least 1 N heteroatom, —OH, —NO$_2$, or —C(O)OR$^3$, wherein at least 1 $R^1$ is other than H;
$R^2$ is $C_{1-6}$ alkyl, $C_{1-6}$ haloalkyl, cycloalkyl having 3-6 ring members, or —$C_{1-6}$ alkyl-heterocycloalkyl having from 5-6 ring members and at least 2 N heteroatoms as ring members;
$R^3$ is H or $C_{1-6}$ alkyl; and
subscript n is 1, 2, 3, 4, or 5.

12. The method of claim 11, wherein prior to administration of the agent that increases the level of epoxy-fatty acids, said individual has been diagnosed as having experienced maternal immune activation during gestation.

13. The method of claim 11, wherein prior to administration of the agent that increases the level of epoxy-fatty acids, said individual has been diagnosed as having experienced exposure to a toxin during gestation.

* * * * *

SEQUENCE LISTING

<160> NUMBER OF SEQ ID NOS: 38

<210> SEQ ID NO 1
<211> LENGTH: 555

<212> TYPE: PRT
<213> ORGANISM: Homo sapiens

<400> SEQUENCE: 1

Met Thr Leu Arg Ala Ala Val Phe Asp Leu Asp Gly Val Leu Ala Leu
1               5                   10                  15

Pro Ala Val Phe Gly Val Leu Gly Arg Thr Glu Glu Ala Leu Ala Leu
            20                  25                  30

Pro Arg Gly Leu Leu Asn Asp Ala Phe Gln Lys Gly Gly Pro Glu Gly
        35                  40                  45

Ala Thr Thr Arg Leu Met Lys Gly Glu Ile Thr Leu Ser Gln Trp Ile
    50                  55                  60

Pro Leu Met Glu Glu Asn Cys Arg Lys Cys Ser Glu Thr Ala Lys Val
65                  70                  75                  80

Cys Leu Pro Lys Asn Phe Ser Ile Lys Glu Ile Phe Asp Lys Ala Ile
                85                  90                  95

Ser Ala Arg Lys Ile Asn Arg Pro Met Leu Gln Ala Ala Leu Met Leu
            100                 105                 110

Arg Lys Lys Gly Phe Thr Thr Ala Ile Leu Thr Asn Thr Trp Leu Asp
        115                 120                 125

Asp Arg Ala Glu Arg Asp Gly Leu Ala Gln Leu Met Cys Glu Leu Lys
    130                 135                 140

Met His Phe Asp Phe Leu Ile Glu Ser Cys Gln Val Gly Met Val Lys
145                 150                 155                 160

Pro Glu Pro Gln Ile Tyr Lys Phe Leu Leu Asp Thr Leu Lys Ala Ser
                165                 170                 175

Pro Ser Glu Val Val Phe Leu Asp Asp Ile Gly Ala Asn Leu Lys Pro
            180                 185                 190

Ala Arg Asp Leu Gly Met Val Thr Ile Leu Val Gln Asp Thr Asp Thr
        195                 200                 205

Ala Leu Lys Glu Leu Glu Lys Val Thr Gly Ile Gln Leu Leu Asn Thr
    210                 215                 220

Pro Ala Pro Leu Pro Thr Ser Cys Asn Pro Ser Asp Met Ser His Gly
225                 230                 235                 240

Tyr Val Thr Val Lys Pro Arg Val Arg Leu His Phe Val Glu Leu Gly
                245                 250                 255

Ser Gly Pro Ala Val Cys Leu Cys His Gly Phe Pro Glu Ser Trp Tyr
            260                 265                 270

Ser Trp Arg Tyr Gln Ile Pro Ala Leu Ala Gln Ala Gly Tyr Arg Val
        275                 280                 285

Leu Ala Met Asp Met Lys Gly Tyr Gly Glu Ser Ser Ala Pro Pro Glu
    290                 295                 300

Ile Glu Glu Tyr Cys Met Glu Val Leu Cys Lys Glu Met Val Thr Phe
305                 310                 315                 320

Leu Asp Lys Leu Gly Leu Ser Gln Ala Val Phe Ile Gly His Asp Trp
                325                 330                 335

Gly Gly Met Leu Val Trp Tyr Met Ala Leu Phe Tyr Pro Glu Arg Val
            340                 345                 350

Arg Ala Val Ala Ser Leu Asn Thr Pro Phe Ile Pro Ala Asn Pro Asn
        355                 360                 365

Met Ser Pro Leu Glu Ser Ile Lys Ala Asn Pro Val Phe Asp Tyr Gln
    370                 375                 380

Leu Tyr Phe Gln Glu Pro Gly Val Ala Glu Ala Glu Leu Glu Gln Asn
385                 390                 395                 400

Leu Ser Arg Thr Phe Lys Ser Leu Phe Arg Ala Ser Asp Glu Ser Val
                405                 410                 415

Leu Ser Met His Lys Val Cys Glu Ala Gly Gly Leu Phe Val Asn Ser
            420                 425                 430

Pro Glu Glu Pro Ser Leu Ser Arg Met Val Thr Glu Glu Ile Gln
        435                 440                 445

Phe Tyr Val Gln Gln Phe Lys Lys Ser Gly Phe Arg Gly Pro Leu Asn
    450                 455                 460

Trp Tyr Arg Asn Met Glu Arg Asn Trp Lys Trp Ala Cys Lys Ser Leu
465                 470                 475                 480

Gly Arg Lys Ile Leu Ile Pro Ala Leu Met Val Thr Ala Glu Lys Asp
                485                 490                 495

Phe Val Leu Val Pro Gln Met Ser Gln His Met Glu Asp Trp Ile Pro
                500                 505                 510

His Leu Lys Arg Gly His Ile Glu Asp Cys Gly His Trp Thr Gln Met
            515                 520                 525

Asp Lys Pro Thr Glu Val Asn Gln Ile Leu Ile Lys Trp Leu Asp Ser
        530                 535                 540

Asp Ala Arg Asn Pro Pro Val Val Ser Lys Met
545                 550                 555

<210> SEQ ID NO 2
<211> LENGTH: 2290
<212> TYPE: DNA
<213> ORGANISM: Homo sapiens

<400> SEQUENCE: 2
gtgcccctcc ccctgcctct ttcccggcca gagtccagcc ttaacccggg cagagggcgg    60
agtcccgtta aggggggtgtg gggaggaggc ggggccaggg caggggcggg gcagagccgg   120
gccaagctgg gcgggtcatg cgccctggcc ttcgcgcatc tcccaggtta gctgcgtgtc   180
cgggtgctag gctgcagacc cgccgccatg acgctgcgcg cggccgtctt cgaccttgac   240
ggggtgctgg cgctgccagc ggtgttcggc gtcctcggcc gcacggagga ggccctggcg   300
ctgcccagag gacttctgaa tgatgctttc agaaaggggg accagagggt gccactacc    360 cggcttatga aggagagat cacactttcc cagtggatac cactcatgga agaaaactgc   420
aggaagtgct ccgagaccgc taaagtctgc ctccccaaga atttctccat aaaagaaatc   480
tttgacaagg cgatttcagc cagaaagatc aaccgcccca tgctccaggc agctctcatg   540
ctcaggaaga aaggattcac tactgccatc ctcaccaaca cctggctgga cgaccgtgct   600
gagagagatg gcctggccca gctgatgtgt gagctgaaga tgcactttga cttcctgata   660
gagtcgtgtc agtggggaat ggtcaaacct gaacctcaga tctacaagtt tctgctggac   720
accctgaagg ccagccccag tgaggtcgtt ttttggatg acatcggggc taatctgaag   780
ccagcccgtg acttgggaat ggtcaccatc ctggtccagg acactgacac ggccctgaaa   840
gaactggaga aagtgaccgg aatccagctt ctcaataccc cggcccctct gccgacctct   900
tgcaatccaa gtgacatgag ccatgggtac gtgacagtaa agcccagggt ccgtctgcat   960
tttgtggagc tgggctccgg ccctgctgtg tgcctctgcc atggatttcc cgagagttgg  1020
tattcttgga ggtaccagat ccctgctctg gcccaggcag gttaccgggt cctagctatg  1080
gacatgaaag gctatggaga gtcatctgct cctcccgaaa tagaagaata ttgcatggaa  1140
gtgttatgta aggagatggt aaccttcctg gataaactgg gcctctctca gcagtgttc  1200

-continued

```
attggccatg actggggtgg catgctggtg tggtacatgg ctctcttcta ccccgagaga    1260
gtgagggcgg tggccagttt gaatactccc ttcataccag caaatcccaa catgtccect     1320 ttggagagta tcaaagccaa cccagtattt gattaccagc tctacttcca agaaccagga    1380
gtggctgagg ctgaactgga acagaacctg agtcggactt tcaaaagcct cttcagagca    1440
agcgatgaga gtgttttatc catgcataaa gtctgtgaag cgggaggact ttttgtaaat    1500
agcccagaag agcccagcct cagcaggatg gtcactgagg aggaaatcca gttctatgtg    1560
cagcagttca agaagtctgg tttcagaggt cctctaaact ggtaccgaaa catggaaagg    1620
aactggaagt gggcttgcaa aagcttggga cggaagatcc tgattccggc cctgatggtc    1680
acggcggaga aggacttcgt gctcgttcct cagatgtccc agcacatgga ggactggatt    1740
ccccacctga aaggggaca cattgaggac tgtgggcact ggacacagat ggacaagcca     1800
accgaggtga atcagatcct cattaagtgg ctggattctg atgcccggaa cccaccggtg    1860
gtctcaaaga tgtagaacgc agcgtgtgcc cacgctcagc aggtgtgcca tccttccacc    1920 tgctgggca ccattcttag tatacagagg tggccttaca cacatcttgc atggatggca     1980
gcattgttct gaagggtttt gcagaaaaaa aagattttct ttacataaag tgaatcaaat    2040
ttgacattat tttagatccc agagaaatca ggtgtgatta gttctccagg catgaatgca    2100
tcgtcccttt atctgtaaga acccttagtg tcctgtaggg ggacagaatg gggtggccag    2160
gtggtgattt ctcttttgacc aatgcatagt ttggcagaaa aatcagccgt tcatttagaa    2220
gaatcttagc agagattggg atgccttact caataaagct aagatgacta tgctgaaaaa    2280
aaaaaaaaaa                                                                 2290
```

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cagtgttcat tggccatgac tgg                                                  23

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 4
guguucauug gccaugacut t                                                    21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 5
agucauggcc aaugaacact t                                              21

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gaaaggctat ggagagtcat ctg                                            23

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 7
aaggcuaugg agagucauct t                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 8
gaugacucuc cauagccuut t                                              21

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
aaaggctatg gagagtcatc tgc                                            23

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 10
aggcuaugga gagucaucut t                                              21
```

```
<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 11
agaugacucu ccauagccut t                                              21

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
caagcagtgt tcattggcca tga                                            23

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 13
agcaguguuc auuggccaut t                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 14
auggccaaug aacacugcut t                                              21

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
cagcacatgg aggactggat tcc                                            23

<210> SEQ ID NO 16
<211> LENGTH: 21
<212> TYPE: DNA
<213> ORGANISM: Artificial Sequence
<220> FEATURE:
```

-continued

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 16
gcacauggag gacuggauut t                                             21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 17
aauccagucc uccaugugct t                                             21

<210> SEQ ID NO 18
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18 ttcaagaga                                                            9

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
cagtgttcat tggccatgac tgg                                           23

<210> SEQ ID NO 20
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gatccccgtg ttcattggcc atgactttca agagaagtca tggccaatga acactttt     59

<210> SEQ ID NO 21
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
agctaaaaag tgttcattgg ccatgacttc tcttgaaagt catggccaat gaacacggg    59
```

```
<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gaaaggctat ggagagtcat ctg                                            23

<210> SEQ ID NO 23
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gatccccaag gctatggaga gtcatcttca agagagatga ctctccatag ccttttttt    59

<210> SEQ ID NO 24
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
agctaaaaaa aggctatgga gagtcatctc tcttgaagat gactctccat agccttggg    59

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
aaaggctatg gagagtcatc tgc                                            23

<210> SEQ ID NO 26
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gatccccagg ctatggagag tcatctttca agagaagatg actctccata gccttttt     59

<210> SEQ ID NO 27
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
agctaaaaaa ggctatggag agtcatcatc tcttgaaaga tgactctcca tagcctggg    59

<210> SEQ ID NO 28
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
caagcagtgt tcattggcca tga                                              23

<210> SEQ ID NO 29
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gatccccagc agtgttcatt ggccatttca agagaatggc caatgaacac tgcttttt       59

<210> SEQ ID NO 30
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
agctaaaaaa gcagtgttca ttggccattc tcttgaaatg gccaatgaac actgctggg      59

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
cagcacatgg aggactggat tcc                                              23

<210> SEQ ID NO 32
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gatccccgca catggaggac tggattttca agagaaatcc agtcctccat gtgcttttt      59

<210> SEQ ID NO 33
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
agctaaaaag cacatggagg actggatttc tcttgaaaat ccagtcctcc atgtgcggg      59

<210> SEQ ID NO 34
<211> LENGTH: 20
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
uguccagugc ccacaguccu                                                    20

<210> SEQ ID NO 35
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
uucccaccug acacgacucu                                                    20

<210> SEQ ID NO 36
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
guucagccuc agccacuccu                                                    20

<210> SEQ ID NO 37
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
aguccucccg cuucacaga                                                     19

<210> SEQ ID NO 38
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
gcccacuucc aguuccuuuc c                                                  21
```